United States Patent
Naidu et al.

(10) Patent No.: US 9,527,842 B2
(45) Date of Patent: Dec. 27, 2016

(54) INHIBITORS OF HUMAN IMMUNODEFICIENCY VIRUS REPLICATION

(71) Applicant: VIIV HEALTHCARE UK (NO.5) LIMITED, Brentford, Middlesex (GB)

(72) Inventors: B. Narasimhulu Naidu, Durham, CT (US); Manoj Patel, Berlin, CT (US); Timothy P. Connolly, Portland, CT (US)

(73) Assignee: VIIV HEALTHCARE UK (NO.5) LIMITED, Brentford, Middlesex (GB)

( * ) Notice: Subject to any disclaimer, the term of this patent is extended or adjusted under 35 U.S.C. 154(b) by 0 days.

(21) Appl. No.: 14/773,223

(22) PCT Filed: Mar. 13, 2014

(86) PCT No.: PCT/US2014/025525
§ 371 (c)(1),
(2) Date: Sep. 4, 2015

(87) PCT Pub. No.: WO2014/159959
PCT Pub. Date: Oct. 2, 2014

(65) Prior Publication Data
US 2016/0024077 A1  Jan. 28, 2016

Related U.S. Application Data

(60) Provisional application No. 61/781,764, filed on Mar. 14, 2013.

(51) Int. Cl.

| | | |
|---|---|---|
| C07D 471/04 | (2006.01) |
| C07D 519/00 | (2006.01) |
| A61K 31/437 | (2006.01) |
| A61K 31/444 | (2006.01) |
| A61K 31/4545 | (2006.01) |
| A61K 45/06 | (2006.01) |
| C07D 498/22 | (2006.01) |
| C07D 513/22 | (2006.01) |
| A61K 31/538 | (2006.01) |

(52) U.S. Cl.
CPC .......... *C07D 471/04* (2013.01); *A61K 31/437* (2013.01); *A61K 31/444* (2013.01); *A61K 31/4545* (2013.01); *A61K 31/538* (2013.01); *A61K 45/06* (2013.01); *C07D 498/22* (2013.01); *C07D 513/22* (2013.01); *C07D 519/00* (2013.01)

(58) Field of Classification Search
None
See application file for complete search history.

(56) References Cited

FOREIGN PATENT DOCUMENTS

| WO | WO 2012/065963 A2 | 5/2012 |
| WO | WO 2013/025584 A1 | 2/2013 |

*Primary Examiner* — Samantha Shterengarts
(74) *Attorney, Agent, or Firm* — Robert H. Brink; R. Steve Thomas; Edward R. Gimmi

(57) ABSTRACT

The disclosure generally relates to compounds of formula (I), including compositions and methods for treating human immunodeficiency virus (HIV) infection. The disclosure provides novel inhibitors of HIV, pharmaceutical compositions containing such compounds, and methods for using these compounds in the treatment of HIV infection.

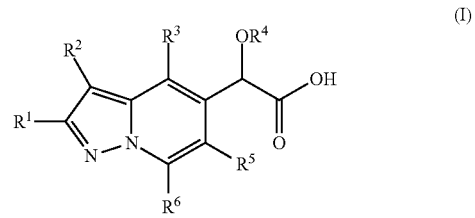

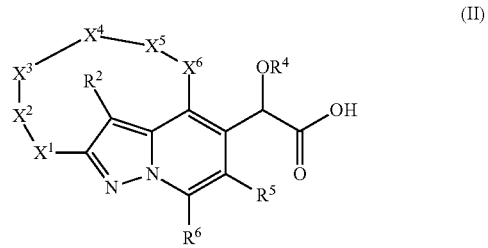

15 Claims, No Drawings

INHIBITORS OF HUMAN IMMUNODEFICIENCY VIRUS REPLICATION

CROSS-REFERENCE TO RELATED APPLICATIONS

This application claims priority to U.S. Provisional Patent Application 61/781,764, filed Mar. 14, 2013, hereby incorporated by reference in its entirety.

BACKGROUND OF THE INVENTION

The disclosure generally relates to compounds, compositions, and methods for the treatment of human immunodeficiency virus (HIV) infection. The disclosure provides novel inhibitors of HIV, pharmaceutical compositions containing such compounds, and methods for using these compounds in the treatment of HIV infection.

Human immunodeficiency virus (HIV) has been identified as the etiological agent responsible for acquired immune deficiency syndrome (AIDS), a fatal disease characterized by destruction of the immune system and the inability to fight off life threatening opportunistic infections. Recent statistics indicate that as many as 33.3 million people worldwide are infected with the virus (UNAIDS Report on the Global AIDS Epidemic 2010). In addition to the large number of individuals already infected, the virus continues to spread. Estimates from 1998 point to close to 6 million new infections in that year alone. In the same year there were approximately 2.5 million deaths associated with HIV and AIDS.

There are currently a number of antiviral drugs available to combat the infection. These drugs can be divided into classes based on the viral protein they target or their mode of action. In particular, saquinavir, indinavir, ritonavir, nelfinavir atazanavir darunavir, amprenavir, fosamprenavir, lopinavir and tipranavir are competitive inhibitors of the aspartyl protease expressed by HIV. Zidovudine, didanosine, stavudine, lamivudine, zalcitabine, emtricitibine, tenofovir and abacavir are nucleos(t)ide reverse transcriptase inhibitors that behave as substrate mimics to halt viral cDNA synthesis. The non-nucleoside reverse transcriptase inhibitors nevirapine, delavirdine, efavirenz and etravirine inhibit the synthesis of viral cDNA via a non-competitive (or uncompetitive) mechanism. Enfuvirtide and maraviroc inhibit the entry of the virus into the host cell. An HIV integrase inhibitor, raltegravir (MK-0518, Isentress®), has also been approved for use in treatment experienced patients, and it is clear that this class of inhibitors is very effective as part of a combination regimen containing HIV inhibitors of different classes.

Used alone, these drugs are effective in reducing viral replication: However, the effect is only temporary as the virus readily develops resistance to all known agents used as monotherapy. On the other hand, combination therapy has proven very effective at both reducing virus and suppressing the emergence of resistance in a number of patients. In the US, where combination therapy is widely available, the number of HIV-related deaths has dramatically declined (Palella, F. J.; Delany, K. M.; Moorman, A. C.; Loveless, M. O.; Furher, J.; Satten, G. A.; Aschman, D. J.; Holmberg, S. D. *N. Engl. J. Med.* 1998, 338, 853-860).

Unfortunately, not all patients are responsive and a large number fail this therapy. In fact, initial studies suggest that approximately 30-50% of patients ultimately fail at least one drug in the suppressive combination. Treatment failure in most cases is caused by the emergence of viral resistance. Viral resistance in turn is caused by the replication rate of HIV-1 during the course of infection combined with the relatively high viral mutation rate associated with the viral polymerase and the lack of adherence of HIV-infected individuals in taking their prescribed medications. Clearly, there is a need for new antiviral agents, preferably with activity against viruses already resistant to currently approved drugs. Other important factors include improved safety and a more convenient dosing regimen than many of the currently approved drugs.

Compounds which inhibit HIV replication have been disclosed. See WO2007131350, WO2009062285, WO2009062288, WO2009062289, WO2009062308, WO2010130034, WO2010130842, WO2011015641, WO2011076765, WO2012003497, WO2012003498, WO2012033735, WO2012065963 and WO2012066442

The invention provides technical advantages, for example, the compounds are novel and are useful in the treatment of HIV. Additionally, the compounds provide advantages for pharmaceutical uses, for example, with regard to one or more of their mechanism of action, binding, inhibition efficacy, target selectivity, solubility, safety profiles, or bioavailability.

DESCRIPTION OF THE INVENTION

The invention encompasses compounds of Formula I, including pharmaceutically acceptable salts, their pharmaceutical compositions, and their use in inhibiting HIV integrase and treating those infected with HIV or AIDS.

One aspect of the invention is a compound of Formula I

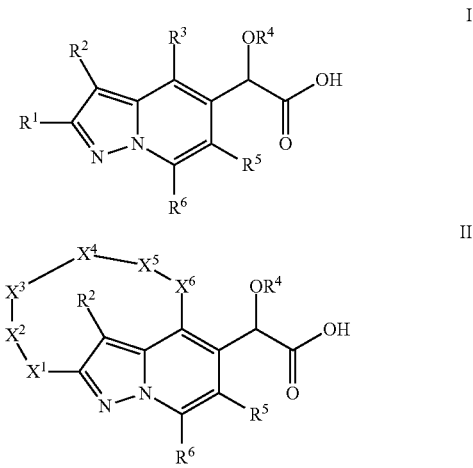

$R^1$ is —CON($R^7$)($R^8$);

or $R^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, indolyl, benzofuranyl, benzothiophenyl, benzimidazolyl, or phenyl, and is substituted with 0-3 substituents selected from cyano, halo, alkyl, haloalkyl, alkenyl, alkoxy, alkenoxy, $Ar^1$, ($Ar^1$)alkyl, and ($Ar^1$)O;

$R^2$ is hydrogen or alkyl;

$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

or R³ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

R⁴ is alkyl or haloalkyl;
R⁵ is alkyl;
R⁶ is hydrogen or alkyl;
R⁷ is Ar¹ or (Ar¹)alkyl;
R⁸ is hydrogen or alkyl;
Ar¹ is phenyl or pyridinyl and is substituted with 0-3 substituents selected from halo, cyano, alkyl, haloalkyl, alkoxy, haloalkoxy, and alkenyloxy;
X¹ is —CONH—;
or X¹ is pyrrolyl, furanyl, thienyl, pyrazolyl, isoxazolyl, isothiazolyl, imidazolyl, oxazolyl, thiazolyl, triazolyl, oxadiazolyl, thiadiazolyl, benzimidazolyl, or phenyl;
X² is phenyl or benzyl and is substituted with 0-3 substituents selected from cyano, halo, alkyl, haloalkyl, alkoxy, and haloalkoxy;
X³ is O or absent;
X⁴ is alkylene or alkenylene;
X⁵ is O or absent; and
X⁶ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
or a pharmaceutically acceptable salt thereof.

Another aspect of the inventions is a compound of formula I where:

R¹ is —CON(R⁷)(R⁸);
or R¹ is pyrrolyl, furanyl, thienyl, pyrazolyl, isoxazolyl, isothiazolyl, imidazolyl, oxazolyl, thiazolyl, triazolyl, oxadiazolyl, thiadiazolyl, indolyl, benzofuranyl, benzothiophenyl, benzimidazolyl, or phenyl, and is substituted with 0-3 substituents selected from halo, alkyl, haloalkyl, alkenyl, Ar¹, (Ar¹)alkyl, and (Ar¹)O;
R² is hydrogen or alkyl;
R³ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
or R³ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
R⁴ is alkyl or haloalkyl;
R⁵ is alkyl;
R⁶ is hydrogen or alkyl;
R⁷ is Ar¹ or (Ar¹)alkyl;
R⁸ is hydrogen or alkyl;
Ar¹ is phenyl or pyridinyl and is substituted with 0-3 substituents selected from halo, cyano, alkyl, haloalkyl, alkoxy, haloalkoxy, and alkenyloxy;
X¹ is pyrrolyl, furanyl, thienyl, pyrazolyl, isoxazolyl, isothiazolyl, imidazolyl, oxazolyl, thiazolyl, triazolyl, oxadiazolyl, thiadiazolyl, benzimidazolyl, or phenyl;
X² is benzyl wherein the benzyl can be substituted with 0-3 substituents selected from halo, alkyl, haloalkyl, alkoxy, and haloalkoxy;
X³ is O or absent; X⁴ is alkylene or alkenylene;
X⁵ is O or absent; and
X⁶ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;
or a pharmaceutically acceptable salt thereof.

Another aspect of the invention is a compound of Formula I.

Another aspect of the invention is a compound of Formula I where
R¹ is —CON(R⁷)(R⁸);
or R¹ is pyrrolyl, furanyl, thienyl, pyrazolyl, isoxazolyl, isothiazolyl, imidazolyl, oxazolyl, thiazolyl, triazolyl, oxadiazolyl, thiadiazolyl, indolyl, benzofuranyl, benzothiophenyl, benzimidazolyl, or phenyl, and is substituted with 0-3 substituents selected from halo, alkyl, haloalkyl, alkenyl, Ar¹, (Ar¹)alkyl, and (Ar¹)O;
R² is hydrogen;
R³ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
or R³ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;
R⁴ is alkyl;
R⁵ is alkyl;
R⁶ is hydrogen;
R⁷ is (Ar¹)alkyl;
R⁸ is hydrogen; and
Ar¹ is phenyl or pyridinyl and is substituted with 0-3 substituents selected from halo, cyano, alkyl, haloalkyl, alkoxy, haloalkoxy, and alkenyloxy;
or a pharmaceutically acceptable salt thereof.

Another aspect of the invention is a compound of Formula I where R¹ is —CON(R⁷)(R⁸).

Another aspect of the invention is a compound of Formula I where R¹ is pyrrolyl, furanyl, thienyl, pyrazolyl, isoxazolyl, isothiazolyl, imidazolyl, oxazolyl, thiazolyl, triazolyl, oxadiazolyl, thiadiazolyl, indolyl, benzofuranyl, benzothiophenyl, benzimidazolyl, or phenyl, and is substituted with 0-3 substituents selected from halo, alkyl, haloalkyl, alkenyl, Ar¹, (Ar¹)alkyl, and (Ar¹)O.

Another aspect of the invention is a compound of Formula I where R³ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of Formula I where R³ is piperidinyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of Formula I where R³ is piperidinyl substituted with 0-3 halo or alkyl substituents.

Another aspect of the invention is a compound of Formula I where R³ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of Formula I where $R^3$ is chromanyl substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl.

Another aspect of the invention is a compound of Formula I where $R^3$ is chromanyl substituted with 0-3 halo or alkyl substituents.

Another aspect of the invention is a compound of Formula II.

Another aspect of the invention is a compound of Formula II where $X^1$ is —CONH—.

Another aspect of the invention is a compound of Formula II where $X^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, benzimidazolyl, or phenyl.

Another aspect of the invention is a compound of Formula II where $X^2$ is phenyl substituted with 0-3 substituents selected from cyano, halo, alkyl, haloalkyl, alkoxy, and haloalkoxy.

Another aspect of the invention is a compound of Formula II where $X^2$ is benzyl substituted with 0-3 substituents selected from cyano, halo, alkyl, haloalkyl, alkoxy, and haloalkoxy.

Another aspect of the invention is a compound of Formula II where $X^6$ is piperidinyl substituted with 0-3 halo or alkyl substituents.

For a compound of Formula I, the scope of any instance of a variable substituent, including $R^1$, $R^2$, $R^3$, $R^4$, $R^5$, $R^6$, $R^7$, $R^8$, $Ar^1$, $X^1$, $X^2$, $X^3$, $X^4$, $X^5$, and $X^6$, can be used independently with the scope of any other instance of a variable substituent. As such, the invention includes combinations of the different aspects.

Unless specified otherwise, these terms have the following meanings "Alkyl" means a straight or branched alkyl group composed of 1 to 6 carbons. "Alkenyl" means a straight or branched alkyl group composed of 2 to 6 carbons with at least one double bond. "Alkylene" means a straight or branched divalent alkyl group composed of 1 to 6 carbons. "Alkenylene" means a straight or branched divalent alkene group composed of 2 to 6 carbons with at least one double bond. "Cycloalkyl" means a monocyclic ring system composed of 3 to 7 carbons. "Hydroxyalkyl," "alkoxy" and other terms with a substituted alkyl moiety include straight and branched isomers composed of 1 to 6 carbon atoms for the alkyl moiety. "Halo" includes fluoro, chloro, bromo, and iodo. "Halo" includes all halogenated isomers from monohalo substituted to perhalo substituted in substituents defined with halo, for example, "Haloalkyl" and "haloalkoxy", "halophenyl", "halophenoxy." "Aryl" includes carbocyclic and heterocyclic aromatic substituents. Substituents which are illustrated by chemical drawing to bond at variable positions on a multiple ring system (for example a bicyclic ring system) are intended to bond to the ring where they are drawn to append. Parenthetic and multiparenthetic terms are intended to clarify bonding relationships to those skilled in the art. For example, a term such as ((R)alkyl) means an alkyl substituent further substituted with the substituent R.

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

Some of the compounds of the invention exist in stereoisomeric forms. The invention includes all stereoisomeric forms of the compounds including enantiomers and diastereromers. Methods of making and separating stereoisomers are known in the art. The invention includes all tautomeric forms of the compounds. The invention includes atropisomers and rotational isomers.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Biological Methods

Inhibition of HIV Replication.

A recombinant NL-Rluc virus was constructed in which a section of the nef gene from NL4-3 was replaced with the *Renilla Luciferase* gene. The NL-RLuc virus was prepared by co-transfection of two plasmids, pNLRLuc and pVS-Venv. The pNLRLuc contains the NL-Rluc DNA cloned into pUC18 at the PvuII site, while the pVSVenv contains the gene for VSV G protein linked to an LTR promoter. Transfections were performed at a 1:3 ratio of pNLRLuc to pVSVenv in 293T cells using the LipofectAMINE PLUS kit from Invitrogen (Carlsbad, Calif.) according to the manufacturer, and the pseudotype virus generated was titered in MT-2 cells. For susceptibility analyses, the titrated virus was used to infect MT-2 cells in the presence of compound, and after 5 days of incubation, cells were processed and quantitated for virus growth by the amount of expressed luciferase. This provides a simple and easy method for quantitating the extent of virus growth and consequently, the antiviral activity of test compounds. Luciferase was quantitated using the Dual Luciferase kit from Promega (Madison, Wis.).

Susceptibility of viruses to compounds was determined by incubation in the presence of serial dilutions of the compound. The 50% effective concentration ($EC_{50}$) was calculated by using the exponential form of the median effect equation where $(Fa)=1/[1+(ED_{50}/drug\ conc.)^m]$ (Johnson V A, Byington R T. Infectivity Assay. In *Techniques in HIV Research*. ed. Aldovini A, Walker B D. 71-76. New York: Stockton Press. 1990). The anti-viral activity of compounds was evaluated under three serum conditions, 10% FBS, 15 mg/ml human serum albumin/10% FBS or 40% human serum/5% FBS, and the results from at least 2 experiments were used to calculate the $EC_{50}$ values. Results are shown in Table 1

TABLE 1

| Example | $EC_{50}$ µM |
|---|---|
| 1 | 0.003 |
| 2 | 0.063 |
| 3 | 0.017 |
| 4 | 0.018 |
| 5 | 0.005 |
| 25 | 0.037 |
| 26 | 0.006 |
| 27 | 0.004 |
| 28 | 0.138 |
| 29 | 0.040 |
| 30 | 0.084 |
| 31 | 0.258 |
| 32 | 0.178 |
| 33 | 0.116 |
| 34 | 0.014 |
| 35 | 0.607 |
| 36 | 0.050 |
| 37 | 0.029 |
| 38 | 0.030 |
| 39 | 0.038 |
| 40 | 2.348 |
| 41 | 0.728 |
| 42 | 0.007 |

Pharmaceutical Composition and Methods of Use

The compounds of this invention inhibit HIV replication. Accordingly, another aspect of the invention is a method for treating HIV infection in a human patient comprising administering a therapeutically effective amount of a compound of Formula I, or a pharmaceutically acceptable salt thereof, with a pharmaceutically acceptable carrier.

Another aspect of the invention is the use of a compound of formula I in the manufacture of a medicament for the treatment of AIDS or HIV infection.

Another aspect of the invention is a method for treating HIV infection in a human patient comprising the administration of a therapeutically effective amount of a compound of Formula I, or a pharmaceutically acceptable salt thereof, with a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

Another aspect of the invention is a method wherein the agent is a nucleoside HIV reverse transcriptase inhibitor.

Another aspect of the invention is a method wherein the nucleoside HIV reverse transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is a method wherein the agent is a non-nucleoside HIV reverse transcriptase inhibitor.

Another aspect of the invention is a method wherein the non-nucleoside HIV reverse transcriptase inhibitor is selected from the group consisting of delavirdine, efavirenz, and nevirapine, or a pharmaceutically acceptable thereof.

Another aspect of the invention is a method wherein the agent is an HIV protease inhibitor.

Another aspect of the invention is a method wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is a method wherein the agent is an HIV fusion inhibitor.

Another aspect of the invention is a method wherein the HIV fusion inhibitor is enfuvirtide or T-1249, or a pharmaceutically acceptable salt thereof.

Another aspect of the invention is a method wherein the agent is an HIV attachment inhibitor.

Another aspect of the invention is a method wherein the agent is a CCR5 inhibitor.

Another aspect of the invention is a method wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100, or a pharmaceutically acceptable salt thereof. Another aspect of the invention is a method wherein the agent is an HIV budding or maturation inhibitor.

Another aspect of the invention is a method wherein the budding or maturation inhibitor is PA-457, or a pharmaceutically acceptable salt thereof.

Another aspect of the invention is a method wherein the agent is an HIV integrase inhibitor.

Another aspect of the invention is a pharmaceutical composition comprising a therapeutically effective amount of a compound of Formula I, or a pharmaceutically acceptable salt thereof, with at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

Another aspect of the invention is the composition wherein the agent is a nucleoside HIV reverse transcriptase inhibitor.

Another aspect of the invention is the composition wherein the nucleoside HIV transcriptase inhibitor is selected from the group consisting of abacavir, didanosine, emtricitabine, lamivudine, stavudine, tenofovir, zalcitabine, and zidovudine, or a pharmaceutically acceptable salt thereof.

Another aspect of the invention is the composition wherein the agent is a non-nucleoside HIV reverse transcriptase inhibitor.

Another aspect of the invention is the composition wherein the non-nucleoside HIV reverse transcriptase inhibitor is selected from the group consisting of delavirdine, efavirenz, and nevirapine, or a pharmaceutically acceptable salt thereof.

Another aspect of the invention is the composition wherein the agent is an HIV protease inhibitor.

Another aspect of the invention is the composition wherein the HIV protease inhibitor is selected from the group consisting of amprenavir, atazanavir, indinavir, lopinavir, nelfinavir, ritonavir, saquinavir and fosamprenavir, or a pharmaceutically acceptable salt thereof.

Another aspect of the invention is the composition wherein the agent is an HIV fusion inhibitor.

Another aspect of the invention is the composition method wherein the HIV fusion inhibitor is enfuvirtide or T-1249, or a pharmaceutically acceptable salt thereof.

Another aspect of the invention is the composition wherein the agent is an HIV attachment inhibitor.

Another aspect of the invention is the composition wherein the agent is a CCR5 inhibitor.

Another aspect of the invention is the composition wherein the CCR5 inhibitor is selected from the group consisting of Sch-C, Sch-D, TAK-220, PRO-140, and UK-427,857, or a pharmaceutically acceptable salt thereof.

Another aspect of the invention is a method wherein the agent is a CXCR4 inhibitor.

Another aspect of the invention is a method wherein the CXCR4 inhibitor is AMD-3100 or a pharmaceutically acceptable salt thereof.

Another aspect of the invention is the composition wherein the agent is an HIV budding or maturation inhibitor.

Another aspect of the invention is the composition wherein the budding or maturation inhibitor is PA-457, or a pharmaceutically acceptable salt thereof.

Another aspect of the invention is the composition wherein the agent is an HIV integrase inhibitor.

"Combination," "coadministration," "concurrent" and similar terms referring to the administration of a compound of Formula I with at least one anti-HIV agent mean that the components are part of a combination antiretroviral therapy or highly active antiretroviral therapy (HAART) as understood by practitioners in the field of AIDS and HIV infection.

"Therapeutically effective" means the amount of agent required to provide a meaningful patient benefit as understood by practitioners in the field of AIDS and HIV infection. In general, the goals of treatment are suppression of viral load, restoration and preservation of immunologic function, improved quality of life, and reduction of HIV-related morbidity and mortality.

"Patient" means a person infected with the HIV virus and suitable for therapy as understood by practitioners in the field of AIDS and HIV infection.

"Treatment," "therapy," "regimen," "HIV infection," "ARC," "AIDS" and related terms are used as understood by practitioners in the field of AIDS and HIV infection.

The compounds of this invention are generally given as pharmaceutical compositions comprised of a therapeutically effective amount of a compound of Formula I or its pharmaceutically acceptable salt and a pharmaceutically acceptable carrier and may contain conventional excipients. A therapeutically effective amount is that which is needed to provide a meaningful patient benefit. Pharmaceutically acceptable carriers are those conventionally known carriers having acceptable safety profiles. Compositions encompass all common solid and liquid forms including capsules, tablets, lozenges, and powders as well as liquid suspensions, syrups, elixers, and solutions. Compositions are made using common formulation techniques, and conventional excipients (such as binding and wetting agents) and vehicles (such as water and alcohols) are generally used for compositions. See, for example, *Remington's Pharmaceutical Sciences*, 17th edition, Mack Publishing Company, Easton, Pa. (1985).

Solid compositions are normally formulated in dosage units and compositions providing from about 1 to 1000 mg of the active ingredient per dose are preferred. Some examples of dosages are 1 mg, 10 mg, 100 mg, 250 mg, 500 mg, and 1000 mg. Generally, other antiretroviral agents will be present in a unit range similar to agents of that class used clinically. Typically, this is 0.25-1000 mg/unit.

Liquid compositions are usually in dosage unit ranges. Generally, the liquid composition will be in a unit dosage range of 1-100 mg/mL. Some examples of dosages are 1 mg/mL, 10 mg/mL, 25 mg/mL, 50 mg/mL, and 100 mg/mL. Generally, other antiretroviral agents will be present in a unit range similar to agents of that class used clinically. Typically, this is 1-100 mg/mL.

The invention encompasses all conventional modes of administration; oral and parenteral methods are preferred. Generally, the dosing regimen will be similar to other antiretroviral agents used clinically. Typically, the daily dose will be 1-100 mg/kg body weight daily. Generally, more compound is required orally and less parenterally. The specific dosing regime, however, will be determined by a physician using sound medical judgement.

The invention also encompasses methods where the compound is given in combination therapy. That is, the compound can be used in conjunction with, but separately from, other agents useful in treating AIDS and HIV infection. Some of these agents include HIV attachment inhibitors, CCR5 inhibitors, CXCR4 inhibitors, HIV cell fusion inhibitors, HIV integrase inhibitors, HIV nucleoside reverse transcriptase inhibitors, HIV non-nucleoside reverse transcriptase inhibitors, HIV protease inhibitors, budding and maturation inhibitors, immunomodulators, and anti-infectives. In these combination methods, the compound of Formula I will generally be given in a daily dose of 1-100 mg/kg body weight daily in conjunction with other agents. The other agents generally will be given in the amounts used therapeutically. The specific dosing regime, however, will be determined by a physician using sound medical judgement.

Synthetic Methods

The compounds of this invention can be made by various methods known in the art including those of the following schemes and in the specific embodiments section. The structure numbering and variable numbering shown in the synthetic schemes are distinct from, and should not be confused with, the structure or variable numbering in the claims or the rest of the specification. The variables in the schemes are meant only to illustrate how to make some of the compounds of this invention. The disclosure is not limited to the foregoing illustrative examples and the examples should be considered in all respects as illustrative and not restrictive, reference being made to the appended claims, rather than to the foregoing examples, and all changes which come within the meaning and range of equivalency of the claims are therefore intended to be embraced.

Abbreviations used in the schemes and examples generally follow conventions used in the art. Chemical abbreviations used in the specification and examples are defined as follows: "KHMDS" for potassium bis(trimethylsilyl)amide; "DMF" for N,N-dimethylformamide; "HATU" for O-(t-Azabenzotriazol-1-yl)-N,N,N',N'-tetramethyluronium hexafluorophosphate, "MeOH" for methanol; "Ar" for aryl; "TFA" for trifluoroacetic acid, "DMSO" for dimethylsulfoxide; "h" for hours; "rt" for room temperature or retention time (context will dictate); "min" for minutes; "EtOAc" for ethyl acetate; "THF" for tetrahydrofuran; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; and "DIEA" for diisopropylethylamine.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" for milliliter or milliliters, "A" for microliter or microliters, "N" for normal, "M" for molar, "mmol" for millimole or millimoles, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Some compounds of this invention can be synthesized from an appropriately substituted heterocycle I-1 according to Scheme I, Compound I-1, I-II and I-3 are commercially available or synthesized by reactions well known in the art. Intermediates I-4 can be prepared by procedure well known in the art or as set forth in the examples below using compound I-1, I-2 and compound I-3. Intermediates I-4 are convenietly transformed to intermediates I-6 via intermediates I-5 using conditions well-known to those skilled in the art. Intermediates I-6 are converted to ketoester intermediates I-8 by a well-known conditions, including but not limited to using sulfonium salt I-7. Intermediates I-8 are reduced to chiral intermediates I-9 using well-known conditions in the presence of catalytic chiral Lewis acid. Intermediates I-9 are converted to the intermediates I-10 by well-known conditions, including but not limited to tertiary-butyl acetate and perchloric acid. Intermediates I-10 are conveniently transformed to intermediates I-11 using conditions well-known in the art, including but not limited to the Suzuki coupling between intermediates I-10 and R$_2$—B(OR)$_2$. The boronate or boronic acid coupling reagents are commercially available or are prepared by reactions well-known to those skilled in the art (PCT Appln. WO20090662285). The diester intermediates I-11 are regioselectively converted to monocaboxylic acid intermediates I-12 by methods well-known in the art. Intermediates I-12 are conveniently converted to intermediates I-13 by conditions well-known to those skilled in the art, including but not limited to HATU. The intermediates I-13 were transformed to final compounds 1-14 by conditions well known in the literature.

Scheme I.

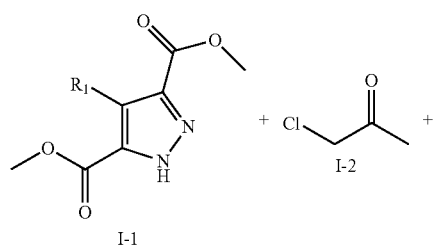

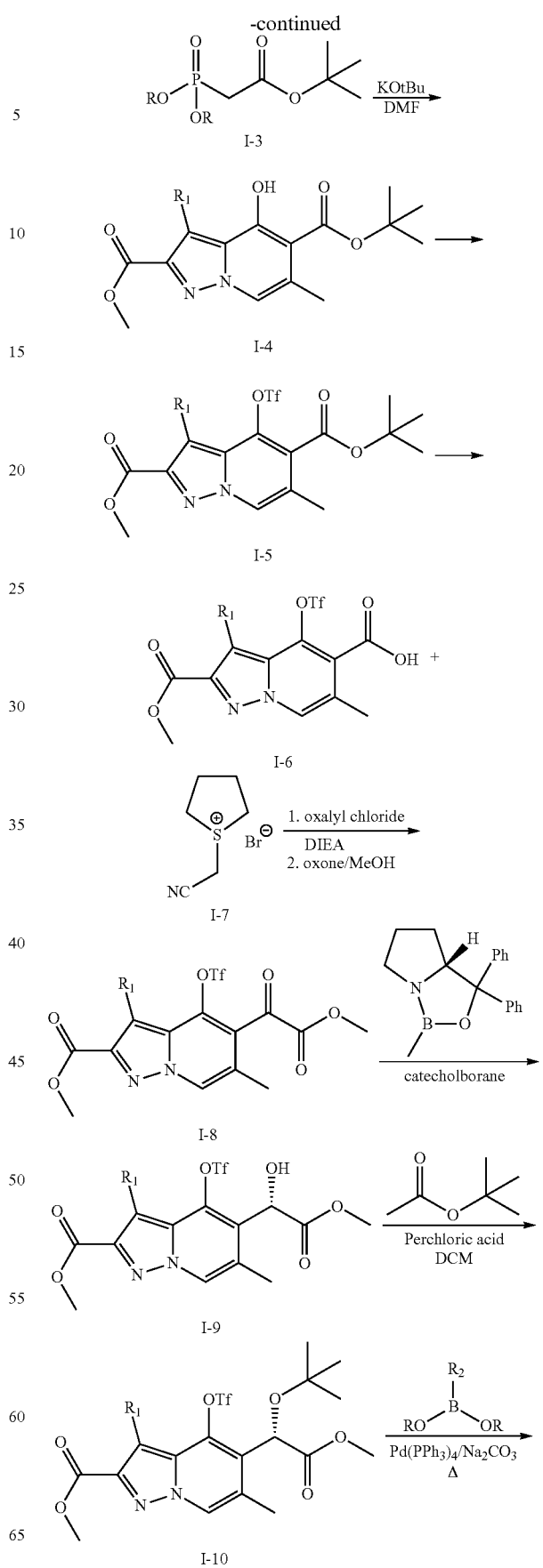

-continued
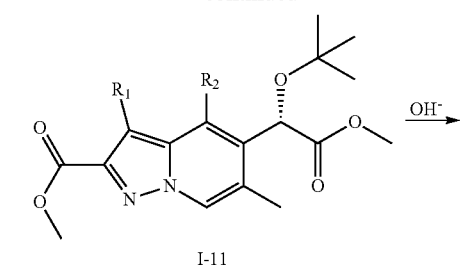
I-11
OH⁻ →
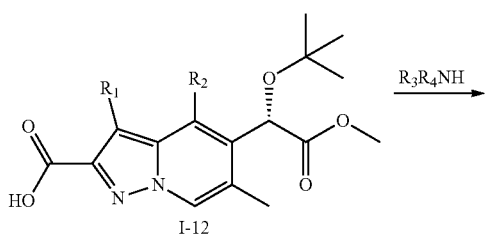
I-12
R₃R₄NH →
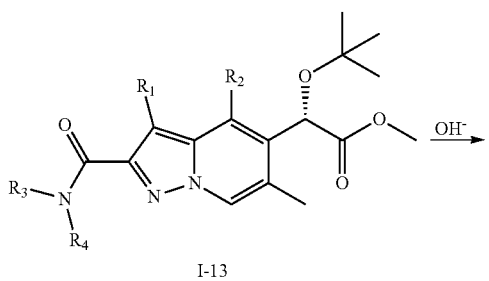
I-13
OH⁻ →
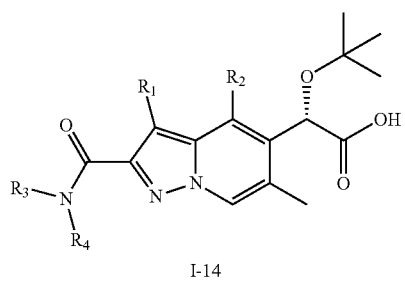
I-14
Some compounds of this invention can be prepared by the methods outlined in the Scheme II.
Scheme II
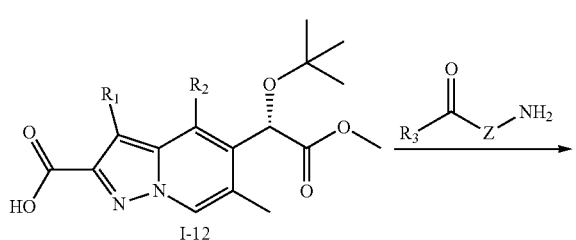
I-12
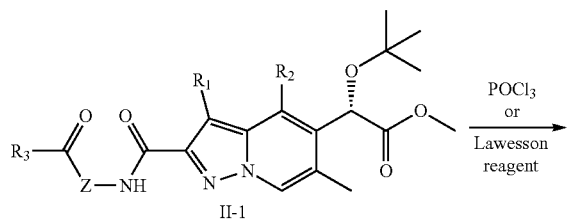
II-1
POCl₃ or Lawesson reagent →
-continued
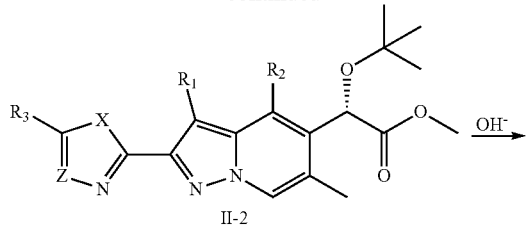
II-2
OH⁻ →
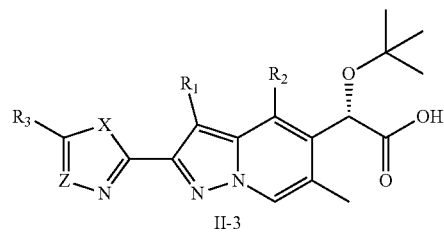
II-3
Some compounds of this invention can be prepared by the methods outlined in the Scheme III.
Scheme III
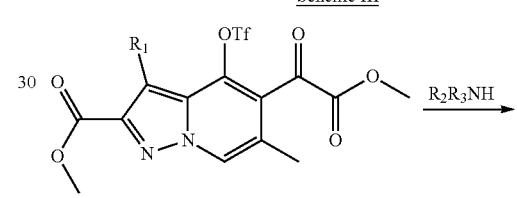
I-8
R₂R₃NH →
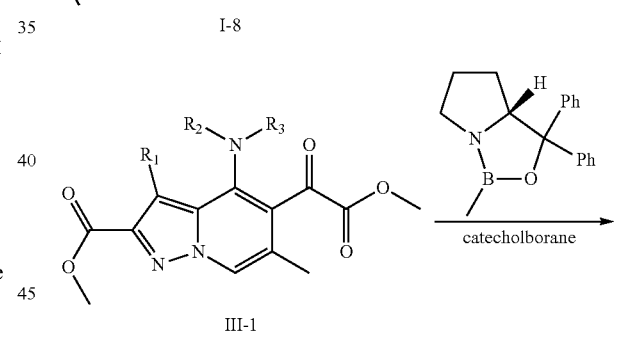
III-1
catecholborane →
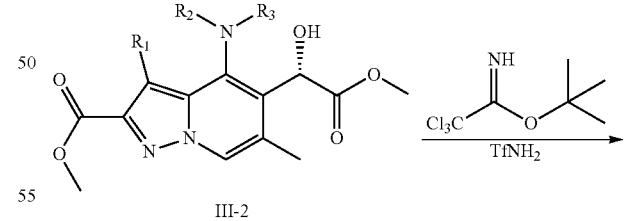
III-2
TfNH₂ →
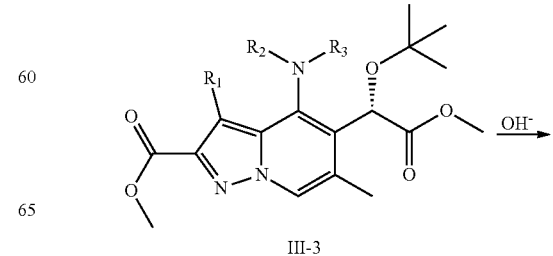
III-3
OH⁻ →

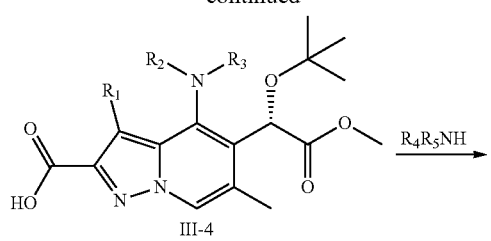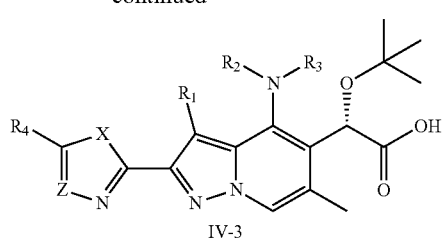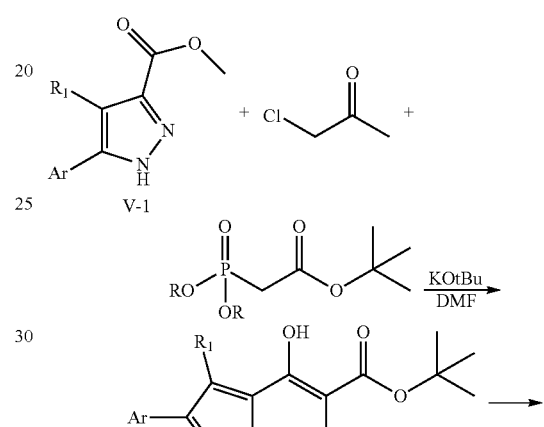
Some compounds of this invention can be prepared by the methods outlined in the Scheme V.
Scheme V
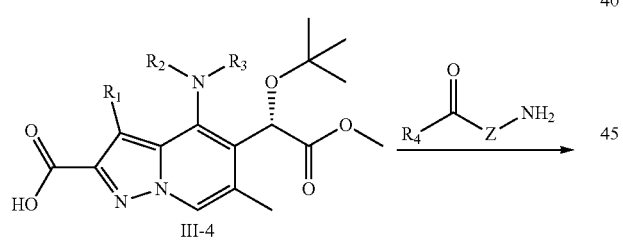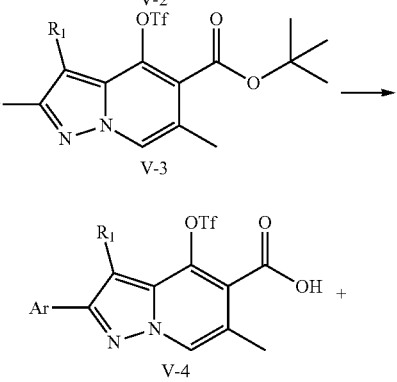
Some compounds of this invention can be prepared by the methods outlined in the Scheme IV.
Scheme IV
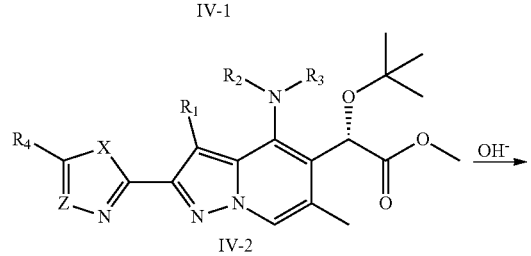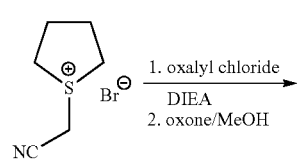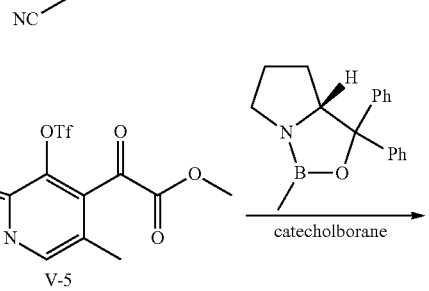

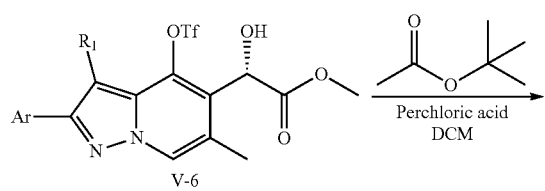
V-6
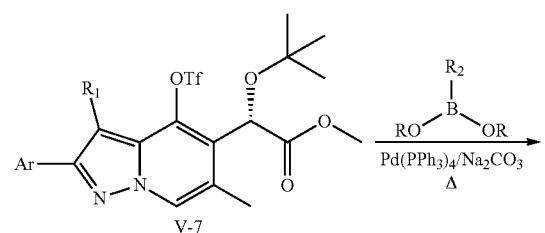
V-7
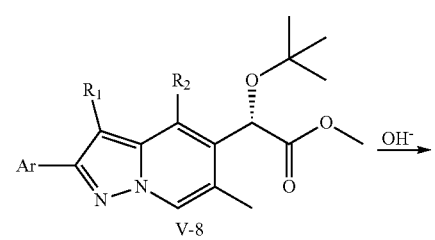
V-8
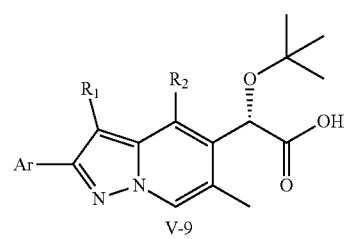
V-9
Some compounds of this invention can be prepared by the methods outlined in the Scheme VI.
Scheme VI
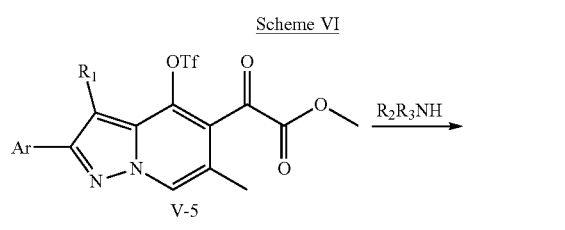
V-5
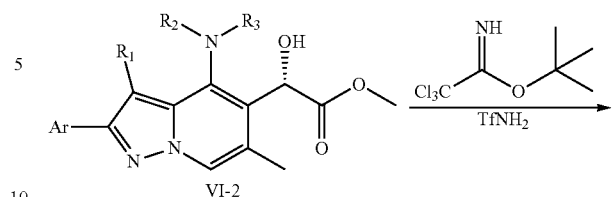
VI-2
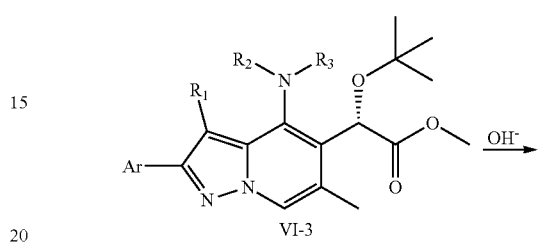
VI-3
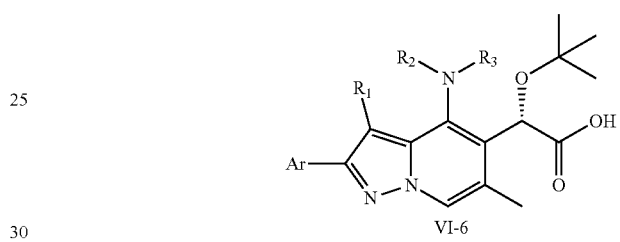
VI-6
Some compounds of this invention can be prepared by the methods outlined in the Scheme VII.
Scheme VII
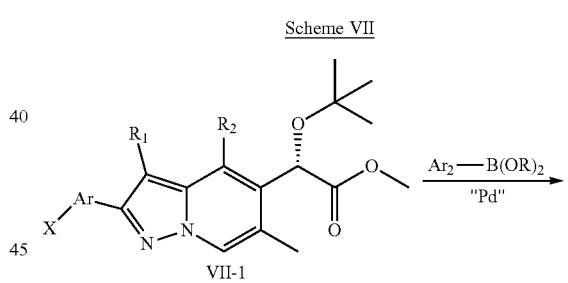
VII-1
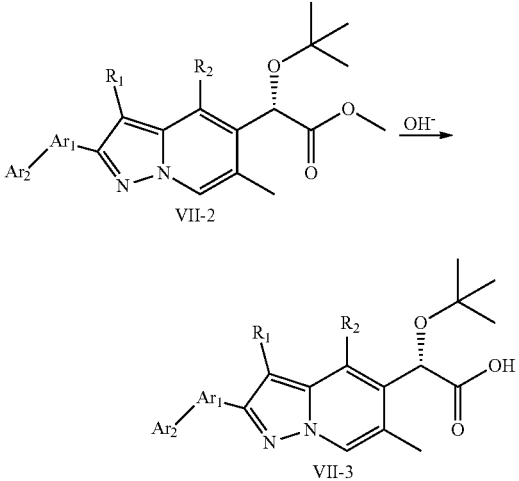
VII-2
VII-3

Some compounds of this invention can be prepared by the methods outlined in the Scheme VIII.

Scheme VIII

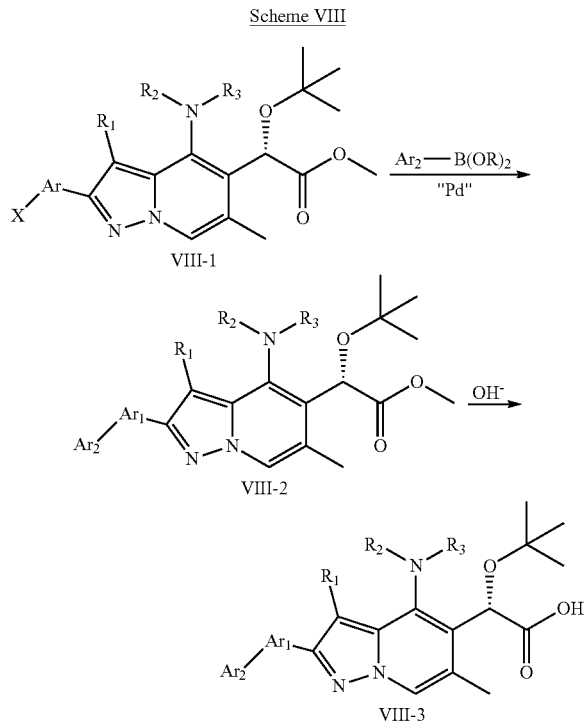

Some compounds of this invention can be prepared by the methods outlined in the Scheme IX.

Scheme IX

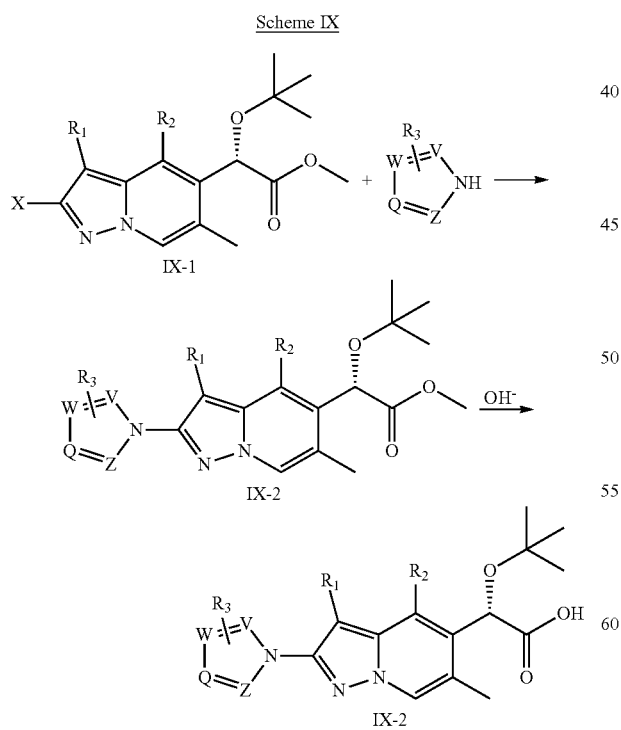

Some compounds of this invention can be prepared by the methods outlined in the Scheme X.

Scheme X

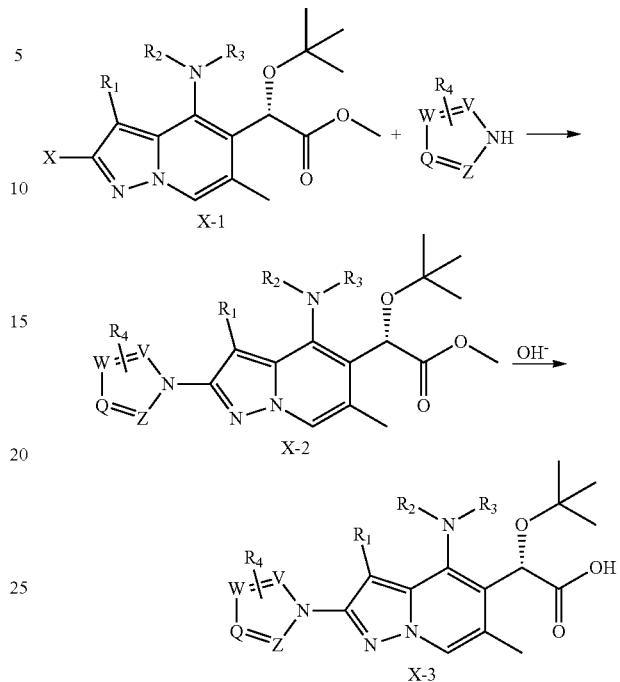

Some compounds of this invention can be prepared by the methods outlined in the Scheme XI.

Scheme XI

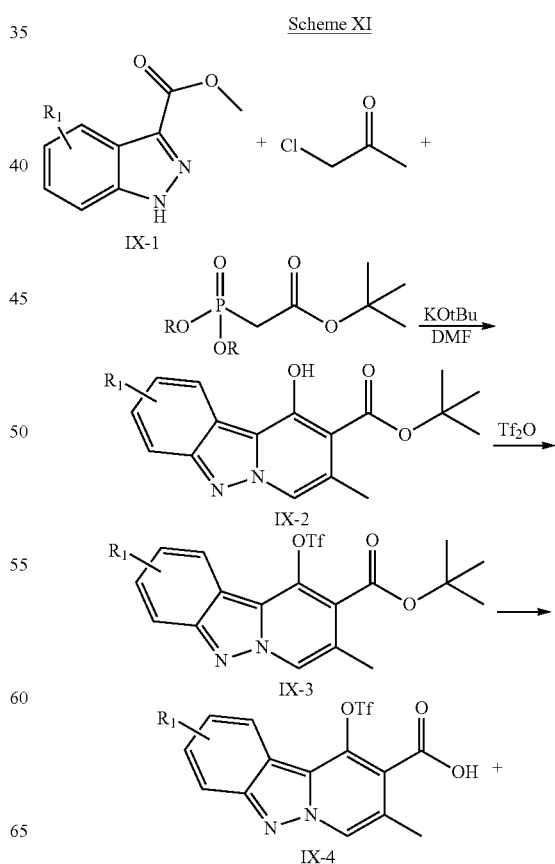

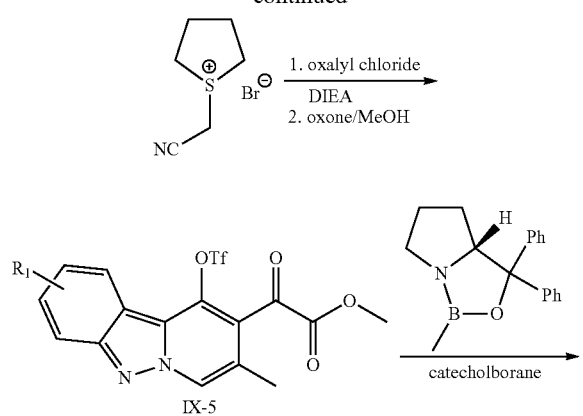
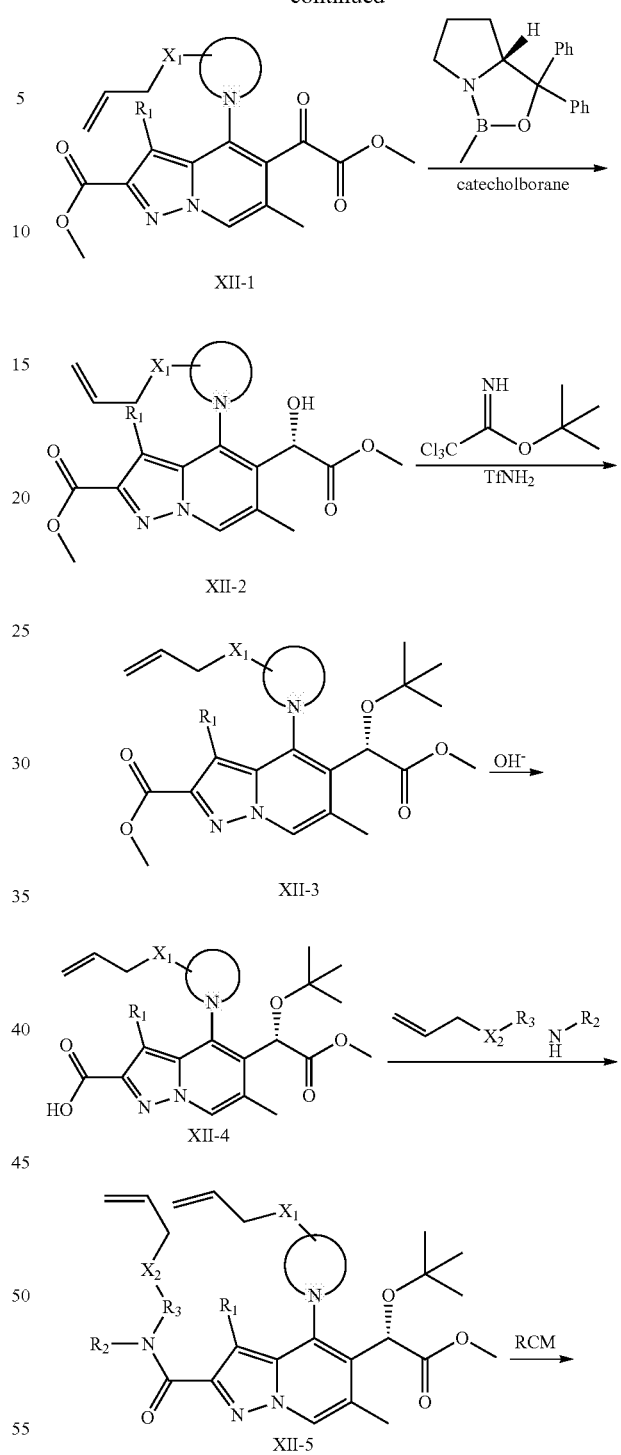
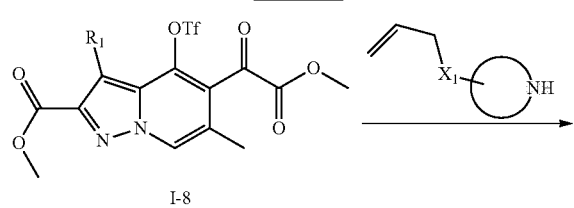
Some compounds of this invention can be prepared by the methods outlined in the Scheme XII.
Scheme XII
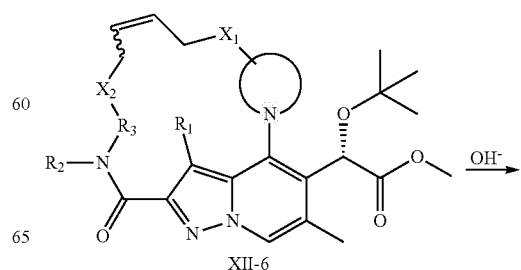

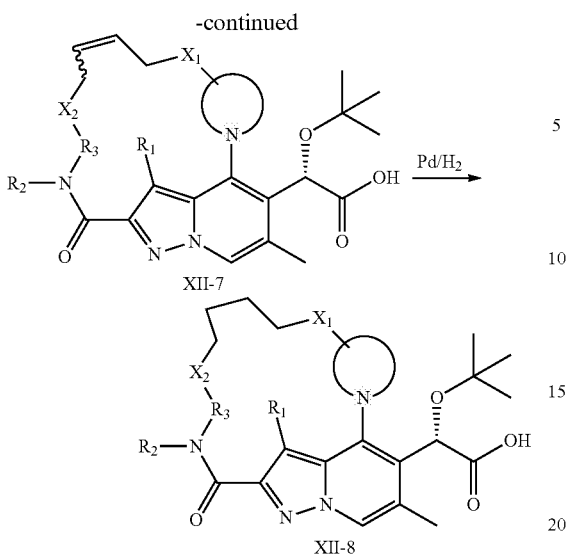

The compounds described herein were purified by the methods known to those skilled in art by normal phase column chromatography on silica gel column using appropriate solvent systems. Preparative HPLC purifications mentioned in this experimentation section were carried out by gradient elution on C18 prep-columns (5 μm) using either mobile phase A: 95:5 H$_2$O/acetonitrile with 10 mM NH$_4$OAc and mobile phase B:A:95:5 acetonitrile/H$_2$O with: 10 mM NH$_4$OAc or phase A: 95:5 H$_2$O/acetonitrile with). 1% TFA and mobile phase B:A:95:5 acetonitrile/H$_2$O with: 0.1% TFA or mobile phase A: 95:5 H$_2$O/MeOH with 20 mM NH$_4$OAc and mobile phase B: 95:5 MeOH/H$_2$O with 20 mM NH$_4$OAc.

Intermediate 1

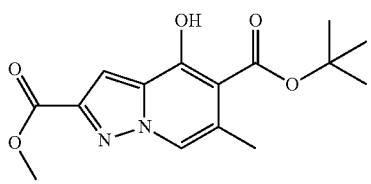 [SMILES: COC(=O)c1cc2c(O)c(C(=O)OC(C)(C)C)c(C)cn2n1]

5-tert-Butyl 2-methyl 4-hydroxy-6-methylpyrazolo [1,5-a]pyridine-2,5-dicarboxylate To a stirred colorless solution of dimethyl 1H-pyrazole-3,5-dicarboxylate (10 g, 54.3 mmol) in DMF (100 mL) was added KOtBu (6.40 g, 57.0 mmol) at once. Note: The reaction turned pale yellow and warm to to touch. After 20 min, the reaction mixture was placed in cold water bath (20° C.) and added dropwise 1-chloropropan-2-one (4.76 ml, 59.7 mmol) over 10 min. After 1 h, ethyl 2-(diethoxyphosphoryl)acetate (13.04 ml, 62.4 mmol) was added at once followed by KOtBu (12.80 g, 114 mmol) over 5 min while maintaining bath temperature between 15-20° C. The resulting dark brown reaction mixture was stirred for 2.5 h at rt and then diluted with ether (300 mL), washed with 1M HCl (75 mL), brine (50 mL), dried (MgSO$_4$), filtered and concentrated to give yellow slurry which was filtered and dried to afford 5-tert-butyl 2-methyl 4-hydroxy-6-methylpyrazolo[1,5-a] pyridine-2,5-dicarboxylate (6.645 g, 21.69 mmol, 39.9% yield) as yellow solid. The filtrated was concentrated and purified by flash chromatography using 1-lit each 5, 10, 15 and 20% EtOAc/hex to afford additional 5-tert-butyl 2-methyl 4-hydroxy-6-methylpyrazolo[1,5-a]pyridine-2,5-dicarboxylate (1.75 g, 5.71 mmol, 10.52% yield) as pale yellow solid. $^1$H NMR (400 MHz, CDCl$_3$) δ 12.95 (s, 1H), 7.84 (s, 1H), 7.40 (s, 1H), 4.00 (s, 3H), 2.47 (d, J=1.0 Hz, 3H), 1.66 (s, 9H). $^{13}$C NMR (101 MHz, CDCl$_3$) δ 170.3, 162.3, 157.4, 143.3, 133.5, 122.7, 119.3, 104.5, 102.2, 84.5, 61.0, 51.9, 28.0, 27.8, 20.6. LCMS (M+H)=307.2.

Intermediate 2

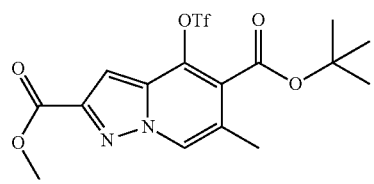 [SMILES: COC(=O)c1cc2c(OS(=O)(=O)C(F)(F)F)c(C(=O)OC(C)(C)C)c(C)cn2n1]

5-tert-Butyl 2-methyl 6-methyl-4-(((trifluoromethyl) sulfonyl)oxy)pyrazolo[1,5-a]pyridine-2,5-dicarboxylate To a stirred yellow solution of 5-tert-butyl 2-methyl 4-hydroxy-6-methylpyrazolo[1,5-a]pyridine-2,5-dicarboxylate (1.75 g, 5.71 mmol) in CH$_2$Cl$_2$ (50 mL) was added Et3N (0.995 mL, 7.14 mmol) at −78° C. To the resulting reaction mixture was added 1M Tf$_2$O/CH$_2$Cl$_2$ (6.28 mL, 6.28 mmol) over 5 min. After 30 min, the reaction was quenched with 1M NH$_4$Cl (50 mL), organic layer separated and aqueous layer extracted with CH$_2$Cl$_2$ (2×50 ml). The combine organic layers dried (Na$_2$SO$_4$), filtered and concentrated. The crude was then triturated with ethyl acetate/hexane, solids were filtered and dried to afford 5-tert-butyl 2-methyl 6-methyl-4-(((trifluoromethyl)sulfonyl)oxy)pyrazolo[1,5-a] pyridine-2,5-dicarboxylate (2 g, 4.56 mmol, 80% yield) as light yellow solid. $^1$H NMR (500 MHz, CDCl$_3$) δ 8.37 (s, 1H), 7.28 (s, 1H), 4.04 (s, 3H), 2.46 (d, J=0.9 Hz, 3H), 1.66 (s, 9H). LCMS (M+H)=439.3.

Intermediate 3

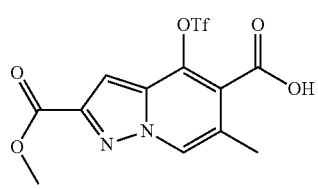 [SMILES: COC(=O)c1cc2c(OS(=O)(=O)C(F)(F)F)c(C(=O)O)c(C)cn2n1]

2-(Methoxycarbonyl)-6-methyl-4-(((trifluoromethyl) sulfonyl)oxy)pyrazolo[1,5-a]pyridine-5-carboxylic acid To a stirred solution of 5-tert-butyl 2-methyl 6-methyl-4-(((trifluoromethyl)sulfonyl)oxy)pyrazolo[1,5-a]pyridine-2, 5-dicarboxylate (2 g, 4.56 mmol) in CH$_2$Cl$_2$ (30 mL) was added TFA (8.79 ml, 114 mmol) at rt. After 5 h, the reaction mixture was concentrated to afford crude methyl 5-(chlorocarbonyl)-6-methyl-4-4-(((trifluoromethyl)sulfonyl)oxy) pyrazolo[1,5-a]pyridine-2-carboxylate as brown solid which was used in the subsequent step without purification. ¹H NMR (400 MHz, CDCl₃) δ 8.53-8.42 (m, 1H), 7.36 (s, 1H), 4.05 (s, 3H), 2.55 (d, J=1.3 Hz, 3H). LCMS (M+H)=383.2.

Intermediate 4

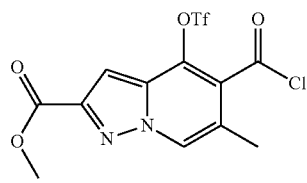 [SMILES: COC(=O)c1cc2c(OS(=O)(=O)C(F)(F)F)c(C(=O)Cl)c(C)cn2n1]

Methyl 5-(chlorocarbonyl)-6-methyl-4-(((trifluoromethyl)sulfonyl)oxy)pyrazolo[1,5-a]pyridine-2-carboxylate To a solution of 2-(methoxycarbonyl)-6-methyl-4-(((trifluoromethyl)sulfonyl)oxy)pyrazolo[1,5-a]pyridine-5-carboxylic acid (1.5 g, 3.92 mmol) in CH₂Cl₂ (25 mL, contains cat. DMF) was added 2M oxalyl chloride (2.94 mL, 5.89 mmol) and the resulting mixture was stirred at room temp for 2 h. Mixture was then concentrated, dried under high vac to afford methyl 5-(chlorocarbonyl)-6-methyl-4-(((trifluoromethyl)sulfonyl)oxy)pyrazolo[1,5-a]pyridine-2-carboxylate and used in the next step.

Intermediate 5

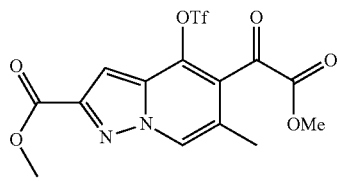 [SMILES: COC(=O)C(=O)c1c(C)cn2nc(C(=O)OC)cc2c1OS(=O)(=O)C(F)(F)F]

Methyl 5-(2-methoxy-2-oxoacetyl)-6-methyl-4-(((trifluoromethyl)sulfonyl)oxy)pyrazolo[1,5-a]pyridine-2-carboxylate To a stirred solution of methyl 5-(chlorocarbonyl)-6-methyl-4-(((trifluoromethyl)sulfonyl)oxy)pyrazolo[1,5-a] pyridine-2-carboxylate (1.5 g, 3.74 mmol) in CH₂Cl₂ (25 mL) was added 1-(cyanomethyl)tetrahydro-1H-thiophen-1-ium, bromide salt (1.169 g, 5.61 mmol) followed by DIEA (1.961 mL, 11.23 mmol) at rt. after 2 h, the reaction mixture was diluted with EtOAc (100 mL), washed with 1M HCl (10 mL), water (50 mL), brine (50 mL), dried (MgSO₄), filtered and concentrated to give intermediate (M+H)=492.2, which was used in the next step without purification. To a stirred solution of above intermediate in MeOH (30 mL) was added a solution of oxone (6.90 g, 11.23 mmol) in water (30 mL) at rt. The resulting suspension was stirred at rt. After 6 h, LCMS indicated approx 30% of desired product. Mixture was then placed in refrigerator overnight and then re-stirred at room temp for 6 h. The reaction mixture was then diluted with ethyl acetate (100 mL), aqueous layer separated and organic layer washed with water (2×50 mL), brine (50 mL), dried (MgSO₄), filtered, concentrated and purified by Bioatge (0-40% EtOAc/hexane) to afford methyl 5-(2-methoxy-2-oxoacetyl)-6-methyl-4-(((trifluoromethyl)sulfonyl)oxy) pyrazolo[1,5-a]pyridine-2-carboxylate (1.3 g, 2.451 mmol, 65.5% yield) as yellow solid. Impurities were present by NMR (sulfone). used as is in the next step without further purification. ¹H NMR (500 MHz, CDCl₃) δ 8.43 (t, J=1.0 Hz, 1H), 7.37 (d, J=0.8 Hz, 1H), 4.05 (s, 3H), 4.01 (s, 3H), 2.38 (d, J=1.1 Hz, 3H). LCMS (M+H)=425.05.

Intermediate 6

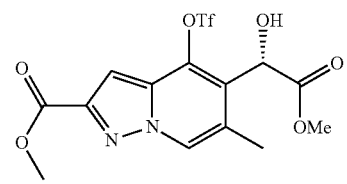 [SMILES: COC(=O)c1cc2c(OS(=O)(=O)C(F)(F)F)c([C@H](O)C(=O)OC)c(C)cn2n1]

(S)-Methyl 5-(1-hydroxy-2-methoxy-2-oxoethyl)-6-methyl-4-(((trifluoromethyl)sulfonyl)oxy)pyrazolo [1,5-a]pyridine-2-carboxylate To a stirred yellow solution of methyl 5-(2-methoxy-2-oxoacetyl)-6-methyl-4-(((trifluoromethyl)sulfonyl)oxy) pyrazolo[1,5-a]pyridine-2-carboxylate (1.2 g, 2.263 mmol) in anhydrous Toluene (50 mL) was added 1M (R)-1-methyl-3,3-diphenylhexahydropyrrolo[1,2-c][1,3,2]oxazaborole/ toluene (0.905 mL, 0.905 mmol). The mixture was cooled to −35° C. and a solution of catechoborane/toluene (0.776 mL, 3.17 mmol) was added over 5 min. After 30 min, the reaction mixture was slowly warmed to −15° C. and stirred for additional 2 h. and diluted with EtOAc (100 mL) and sat. Na₂CO₃ (50 mL). The mixture was stirred vigorously for 30 min, and the organic phase washed with sat Na₂CO₃ (2×50 mL), dried (Na₂SO₄), filtered, concentrated and the residue was purified by silica gel chromatography (5-100% EtOAc/ hexane) to afford desired (S)-methyl 5-(1-hydroxy-2-methoxy-2-oxoethyl)-6-methyl-4-(((trifluoromethyl)sulfonyl)oxy)pyrazolo[1,5-a]pyridine-2-carboxylate (300 mg, 0.704 mmol, 31.1% yield) as off-white solid. ¹H NMR (400 MHz, CDCl₃) δ 8.35 (s, 1H), 7.26 (d, J=0.8 Hz, 1H), 5.66 (d, J=2.5 Hz, 1H), 4.04 (s, 3H), 3.86 (s, 3H), 3.45 (d, J=2.5 Hz, 1H), 2.37 (d, J=1.3 Hz, 3H). LCMS (M+H)=427.2.

Intermediate 7

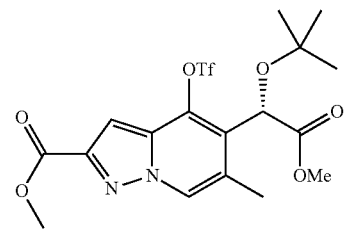 [SMILES: COC(=O)c1cc2c(OS(=O)(=O)C(F)(F)F)c([C@H](OC(C)(C)C)C(=O)OC)c(C)cn2n1]

(S)-Methyl 5-(1-(tert-butoxy)-2-methoxy-2-oxo-ethyl)-6-methyl-4-(((trifluoromethyl)sulfonyl)oxy)pyrazolo[1,5-a]pyridine-2-carboxylate To a stirred solution of (S)-methyl 5-(1-hydroxy-2-methoxy-2-oxoethyl)-6-methyl-4-4-(((trifluoromethyl)sulfonyl)oxy)pyrazolo[1,5-a]pyridine-2-carboxylate (250 mg, 0.586 mmol) in CH$_2$Cl$_2$ (10 mL) and t-butyl acetate (7.00 mL) at rt was added perchloric acid (0.151 mL, 1.759 mmol). After 3 h, the reaction mixture was diluted with CH$_2$Cl$_2$ (100 mL), carefully quenched with sat. NaHCO$_3$ (50 mL), organic layer separated and washed with brine (100 mL), dried (Na$_2$SO$_4$), filtered and concentrated to give yellow liquid. This was purified by flash column chromatography on silica gel column using (10-50% EtOAc/Hex as eluant) to afford the desired (S)-methyl 5-(1-(tert-butoxy)-2-methoxy-2-oxoethyl)-6-methyl-4-(((trifluoromethyl)sulfonyl)oxy)pyrazolo[1,5-a]pyridine-2-carboxylate (200 mg, 0.415 mmol, 70.7% yield) as viscous oil. $^1$H NMR (400 MHz, CDCl$_3$) δ 8.33 (s, 1H), 7.22 (d, J=0.8 Hz, 1H), 5.59 (s, 1H), 4.03 (s, 3H), 3.76 (s, 3H), 2.43 (d, J=1.0 Hz, 3H), 1.25 (s, 9H). LCMS (M+H)=483.3.

Intermediate 8

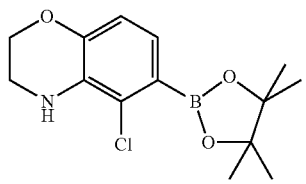 [SMILES: CC1(C)OB(c2ccc3c(c2Cl)NCCO3)OC1(C)C]

5-Chloro-6-(4,4,5,5-tetramethyl-1,3,2-dioxaborolan-2-yl)-3,4-dihydro-2H-benzo[b][1,4]oxazine The title compound was prepared from the known procedure as described in the reference WO 2009/062285.

Intermediate 9

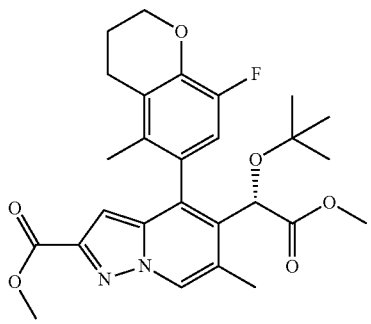 [SMILES: COC(=O)c1cc2c(-c3cc(F)c4c(c3C)CCCO4)c([C@H](OC(C)(C)C)C(=O)OC)c(C)cn2n1]

Methyl 5-((S)-1-(tert-butoxy)-2-methoxy-2-oxo-ethyl)-4-(8-fluoro-5-methylchroman-6-yl)-6-methyl-pyrazolo[1,5-a]pyridine-2-carboxylate A mixture of (S)-methyl 5-(1-(tert-butoxy)-2-methoxy-2-oxoethyl)-6-methyl-4-(((trifluoromethyl)sulfonyl)oxy)pyrazolo[1,5-a]pyridine-2-carboxylate (100 mg, 0.207 mmol), (8-fluoro-5-methylchroman-6-yl)boronic acid (87 mg, 0.415 mmol; prepared according to the procedure in WO 2009062285) and 2M Na$_2$CO$_3$ (0.207 mL, 0.415 mmol) in DMF (1 mL) was degassed for 10 min. Then, tetrakis(triphenylphosphine)palladium(0) (23.95 mg, 0.021 mmol) was added, degassed for 5 min and heated at 110° C. for 2 h using Biotage microwave. Then, cooled, diluted with ether (25 mL), washed with water and brine (10 mL each), dried (MgSO$_4$), filtered and concentrated to give crude, which was purified by Biotage (0-50% EtOAc/hexane) to affordmethyl 5-((S)-1-(tert-butoxy)-2-methoxy-2-oxoethyl)-4-(8-fluoro-5-methylchroman-6-yl)-6-methylpyrazolo[1,5-a]pyridine-2-carboxylate (42 mg, 0.084 mmol, 40.6% yield) as as inseparable mixture (approx 7:1) of atropeisomer. $^1$H NMR (500 MHz, CDCl$_3$) δ 8.30 (s, 0.85H), 8.30 (s, 0.15H), 7.83 (s, 0.15H), 7.74 (d, J=12.0 Hz, 0.85H), 7.03 (d, J=11.0 Hz, 0.15H), 6.79 (d, J=11.0 Hz, 0.85H), 5.19 (s, 0.15H), 5.11 (s, 0.85H), 4.34 (dd, J=5.8, 4.6 Hz, 2H), 4.02 (s, 0.4H), 3.97 (s, 2.6H), 3.74 (s, 0.4H), 3.67 (s, 2.6H), 2.76 (q, J=7.1 Hz, 2H), 2.65 (s, 3H), 2.51 (d, J=0.9 Hz, 3H), 2.24-2.11 (m, 2H), 1.17 (s, 7.8H), 1.04 (s, 1.2H). LCMS (M+H)=499.4.

Intermediate 10

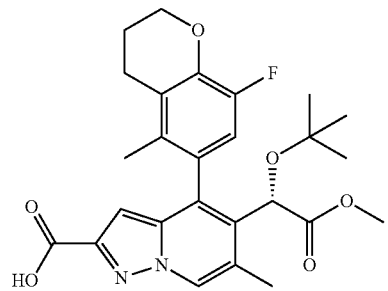 [SMILES: COC(=O)[C@@H](OC(C)(C)C)c1c(C)cn2nc(C(=O)O)cc2c1-c1cc(F)c2c(c1C)CCCO2]

5-((S)-1-(tert-Butoxy)-2-methoxy-2-oxoethyl)-4-(8-fluoro-5-methylchroman-6-yl)-6-methylpyrazolo[1,5-a]pyridine-2-carboxylic acid To a solution of methyl 5-((S)-1-(tert-butoxy)-2-methoxy-2-oxoethyl)-4-(8-fluoro-5-methylchroman-6-yl)-6-methyl-pyrazolo[1,5-a]pyridine-2-carboxylate (42 mg, 0.084 mmol) in MeOH (1 mL) and THF (1 mL) was added 1N NaOH (0.084 mL, 0.084 mmol) and the resulting mixture was stirred at room temp for 5 h. Water was then added and the mixture was extracted with ether (10 mL). Ethereal layer was then discarded and aqueous layer was acidified with 1N HCl and extracted with ethyl acetate (25 mL), washed with brine (10 mL), dried (Na$_2$SO$_4$), filtered and concentrated to afford 5-(((S)-1-(tert-butoxy)-2-methoxy-2-oxoethyl)-4-(8-fluoro-5-methylchroman-6-yl)-6-methylpyrazolo[1,5-a]pyridine-2-carboxylic acid (20 mg, 0.041 mmol, 49.0% yield) as thick paste, which was used in the next step without further purification. $^1$H NMR (500 MHz, CDCl$_3$) δ 8.39 (s, 0.15H), 8.35 (s, 0.85H), 6.80 (d, J=11.0 Hz, 1H), 6.59 (d, J=0.8 Hz, 0.15H), 6.55 (d, J=0.8 Hz, 0.85H), 5.17 (s, 0.15H), 5.12 (s, 0.85H), 4.37-4.33 (m, 2H), 3.78 (s, 0.4H), 3.67 (s, 2.6H), 2.76 (t, J=6.5 Hz, 2H), 2.52 (s, 3H), 2.19 (dd, J=6.2, 4.5 Hz, 2H), 1.84 (s, 3H), 1.17 (s, 8H), 1.04 (s, 1H). LCMS (M+H)=485.3.

Example 1

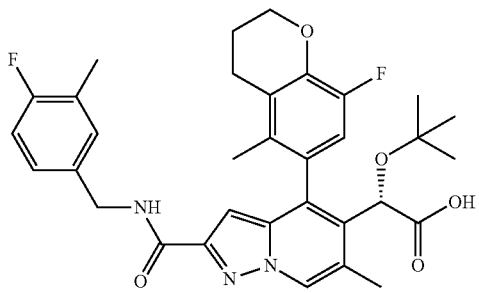 [SMILES: Cc1cc(CNC(=O)c2cc3c(-c4cc(F)c5c(c4C)CCCO5)c([C@H](OC(C)(C)C)C(=O)O)c(C)cn3n2)ccc1F]

(2S)-2-(tert-Butoxy)-2-(2-(((4-fluoro-3-methylbenzyl)carbamoyl)-4-(8-fluoro-5-methylchroman-6-yl)-6-methylpyrazolo[1,5-a]pyridin-5-yl)acetic acid To a solution of 5-((S)-1-(tert-butoxy)-2-methoxy-2-oxoethyl)-4-(8-fluoro-5-methylchroman-6-yl)-6-methylpyrazolo[1,5-a]pyridine-2-carboxylic acid (20 mg, 0.041 mmol) and (4-fluoro-3-methylphenyl)methanamine (11.49 mg, 0.083 mmol) in DMF (1 mL) was added DIEA (0.036 mL, 0.206 mmol) followed by HATU (31.4 mg, 0.083 mmol) and DMAP (0.504 mg, 4.13 μmol) and the resulting mixture was stirred at room temp for 3 h. Water was then added and the mixture was extracted with ether (2×10 mL), washed with brine (10 mL), dried ($Na_2SO_4$), filtered and concentrated. The crude was then treated with 1N NaOH (0.206 mL, 0.206 mmol) in MeOH (1 mL) at 70° C. for 16 h. Mixture was then cooled and purified by prep HPLC to afford (2S)-2-(tert-butoxy)-2-(2-((4-fluoro-3-methylbenzyl)carbamoyl)-4-(8-fluoro-5-methylchroman-6-yl)-6-methylpyrazolo[1,5-a]pyridin-5-yl)acetic acid (12.4 mg, 0.021 mmol, 50.8% yield) as inseparable mixture (approx 7:1) of atropeisomer. $^1$H NMR (500 MHz, DMSO-$d_6$) δ 8.90 (t, J=6.3 Hz, 1H), 8.47 (s, 0.88H), 8.44 (s, 0.12H), 7.20 (d, J=7.3 Hz, 1H), 7.13 (d, J=5.5 Hz, 1H), 7.09-7.02 (m, 1H), 6.84 (d, J=11.3 Hz, 1H), 6.26 (s, 0.12H), 6.19 (s, 0.88H), 4.92 (s, 0.12H), 4.86 (s, 0.88H), 4.43-4.31 (m, 2H), 4.23 (t, J=5.2 Hz, 2H), 2.72-2.65 (m, 2H), 2.45 (s, 2.7H), 2.39 (s, 0.3H), 2.19 (s, 3H), 2.05 (br. s., 2H), 1.81 (s, 2.7H), 1.79 (s, 0.3H), 1.05 (s, 8H), 0.92 (s, 1H). LCMS (M+H)=592.7.

Intermediate 11

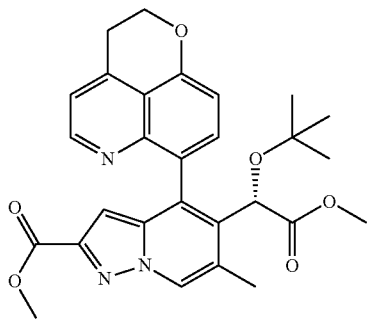 [SMILES: COC(=O)c1cc2c(-c3ccc4c5c(ccnc35)CCO4)c([C@H](OC(C)(C)C)C(=O)OC)c(C)cn2n1]

Methyl 5-((S)-1-(tert-butoxy)-2-methoxy-2-oxoethyl)-4-(2,3-dihydropyrano[4,3,2-de]quinolin-7-yl)-6-methylpyrazolo[1,5-a]pyridine-2-carboxylate A mixture of (S)-methyl 5-(1-(tert-butoxy)-2-methoxy-2-oxoethyl)-6-methyl-4-4-((((trifluoromethyl)sulfonyl)oxy)pyrazolo[1,5-a]pyridine-2-carboxylate (250 mg, 0.518 mmol), (2,3-dihydropyrano[4,3,2-de]quinolin-7-yl)boronic acid (223 mg, 1.036 mmol, ref. WO 2009/062285) and $K_2CO_3$ (143 mg, 1.036 mmol) in DMF (1 mL) was degassed for 10 min. Then, tetrakis(triphenylphosphine)palladium(0) (59.9 mg, 0.052 mmol) was added, degassed for 5 min and heated at 120° C. for 2 h using Biotage microwave. Then, cooled, diluted with ether (25 mL), washed with water and brine (10 mL each), dried ($MgSO_4$), filtered and concentrated to give crude which was purified by prep HPLC to afford methyl 5-((S)-1-(tert-butoxy)-2-methoxy-2-oxoethyl)-4-(2,3-dihydropyrano[4,3,2-de]quinolin-7-yl)-6-methylpyrazolo[1,5-a]pyridine-2-carboxylate (20 mg, 0.040 mmol, 7.66% yield) as approx 2:1 mixture of atropisomers. LCMS (M+H)=504.3.

Intermediate 12

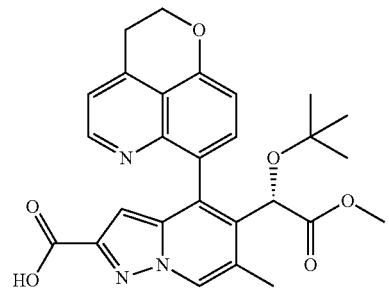 [SMILES: COC(=O)[C@@H](OC(C)(C)C)c1c(C)cn2nc(C(=O)O)cc2c1-c1ccc2c3c(ccnc13)CCO2]

5-((S)-1-(tert-Butoxy)-2-methoxy-2-oxoethyl)-4-(2,3-dihydropyrano[4,3,2-de]quinolin-7-yl)-6-methylpyrazolo[1,5-a]pyridine-2-carboxylic acid To a solution of methyl 5-((S)-1-(tert-butoxy)-2-methoxy-2-oxoethyl)-4-(2,3-dihydropyrano[4,3,2-de]quinolin-7-yl)-6-methylpyrazolo[1,5-a]pyridine-2-carboxylate (12 mg, 0.024 mmol) in MeOH (1 mL) was added 1N NaOH (0.029 mL, 0.029 mmol) and the resulting mixture was stirred at room temp for 16 h. At this point LCMS indicates completion of reaction. Mixture was then purified by prep HPLC to afford 5-((S)-1-(tert-butoxy)-2-methoxy-2-oxoethyl)-4-(2,3-dihydropyrano[4,3,2-de]quinolin-7-yl)-6-methylpyrazolo[1,5-a]pyridine-2-carboxylic acid (8 mg, 0.016 mmol, 68.6% yield) as approx 2:1 mixture of atropisomers. Used as is in the next step. LCMS (M+H)=490.2.

Example 2

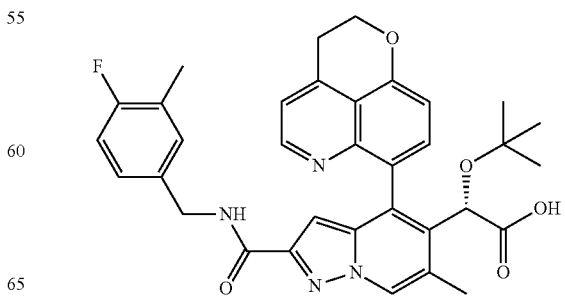

(2S)-2-(tert-Butoxy)-2-(4-(2,3-dihydropyrano[4,3,2-de]quinolin-7-yl)-2-((4-fluoro-3-methylbenzyl)carbamoyl)-6-methylpyrazolo[1,5-a]pyridin-5-yl)acetic acid To a solution of 5-((S)-1-(tert-butoxy)-2-methoxy-2-oxoethyl)-4-(2,3-dihydropyrano[4,3,2-de]quinolin-7-yl)-6-methylpyrazolo[1,5-a]pyridine-2-carboxylic acid (7 mg, 0.014 mmol) and (4-fluoro-3-methylphenyl)methanamine (3.98 mg, 0.029 mmol) in DMF (1 mL) was added DIEA (0.012 mL, 0.071 mmol) followed by HATU (10.87 mg, 0.029 mmol) and DMAP (0.175 mg, 1.430 μmol) and the resulting mixture was stirred at room temp for 3 h. Water (5 mL) was then added and the mixture was extracted with ethyl acetate (15 mL), washed with brine (5 mL), dried (Na2SO4), filtered and concentrated. The residue was then tretated with 1N NaOH (0.071 mL, 0.071 mmol) in MeOH (1 mL) at 75° C. for 3 h. Mixture was then cooled and purified by prep HPLC to afford two atropisomers. First eluting major atropisomer: ¹H NMR (500 MHz, DMSO-d₆) δ 8.82 (t, J=6.3 Hz, 1H), 8.61 (d, J=4.3 Hz, 1H), 8.45 (s, 1H), 7.88 (d, J=7.6 Hz, 1H), 7.30 (d, J=4.6 Hz, 1H), 7.16 (d, J=7.9 Hz, 2H), 7.11 (br. s., 1H), 7.07-6.99 (m, 1H), 5.86 (s, 1H), 4.97 (s, 1H), 4.52 (br. s., 2H), 4.42-4.25 (m, 2H), 3.36-3.32 (m, 2H), 2.43 (s, 3H), 2.18 (s, 3H), 1.91 (s, 9H). LCMS (M+H)=597.4 and second eluting minor atropisomer: ¹H NMR (500 MHz, DMSO-d₆) 8.85 (t, J=6.0 Hz, 1H), 8.60 (d, J=4.0 Hz, 1H), 8.52 (s, 1H), 7.59 (d, J=7.6 Hz, 1H), 7.34 (d, J=4.0 Hz, 1H), 7.16 (d, J=7.6 Hz, 1H), 7.11 (d, J=7.3 Hz, 2H), 7.07-7.00 (m, 1H), 6.02 (s, 1H), 4.87 (s, 1H), 4.58-4.46 (m, 3H), 4.34 (d, J=5.8 Hz, 2H), 3.36-3.32 (m, 4H), 2.18 (s, 3H), 1.91 (s, 9H). LCMS (M+H)=597.4.

Intermediate 13

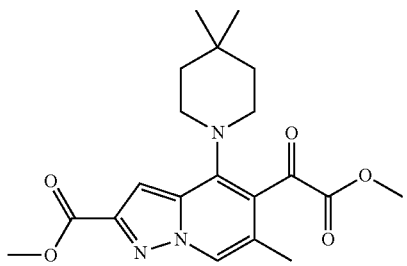

Methyl 4-(4,4-dimethylpiperidin-1-yl)-5-(2-methoxy-2-oxoacetyl)-6-methylpyrazolo[1,5-a]pyridine-2-carboxylate To a stirred solution of methyl 5-(2-methoxy-2-oxoacetyl)-6-methyl-4-(((trifluoromethyl)sulfonyl)oxy)pyrazolo[1,5-a]pyridine-2-carboxylate (2.5 g, 4.71 mmol) and DIEA (1.646 mL, 9.43 mmol) in CH₂Cl₂ (50 mL) at 0° C. was added 4,4-dimethylpiperidine (0.800 g, 7.07 mmol) in CH₂Cl₂ (10 mL) and the resulting mixture was stirred at 0° C. After 1 h, LCMS showed completion of reaction. The reaction mixture was diluted with CH₂Cl₂ (100 mL), washed with water (4×25 mL), brine (25 mL), dried (Na₂SO₄), filtered, concentrated and purified by biotage (0-40% EtOAc/Hex) to afford methyl 4-(4,4-dimethylpiperidin-1-yl)-5-(2-methoxy-2-oxoacetyl)-6-methylpyrazolo[1,5-a]pyridine-2-carboxylate (1.2 g, 3.10 mmol, 65.7% yield) as light solid. ¹H NMR (500 MHz, CDCl₃) δ 8.25 (t, J=1.1 Hz, 1H), 7.33 (d, J=0.9 Hz, 1H), 4.05 (s, 3H), 3.94 (s, 3H), 3.15 (br. s., 4H), 2.32 (d, J=1.1 Hz, 3H), 1.48 (t, J=5.7 Hz, 4H), 1.07 (s, 6H). LCMS (M+H)=388.4.

Intermediate 14

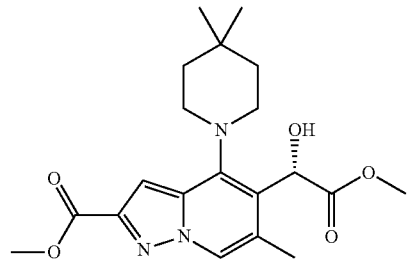

(S)-Methyl 4-(4,4-dimethylpiperidin-1-yl)-5-(1-hydroxy-2-methoxy-2-oxoethyl)-6-methylpyrazolo[1,5-a]pyridine-2-carboxylate To a stirred yellow solution of methyl 4-(4,4-dimethylpiperidin-1-yl)-5-(2-methoxy-2-oxoacetyl)-6-methylpyrazolo[1,5-a]pyridine-2-carboxylate (1.2 g, 3.10 mmol) in anhydrous Toluene (30 mL) was added 1M (R)-1-methyl-3,3-diphenylhexahydropyrrolo[1,2-c][1,3,2]oxazaborole/toluene (1.549 mL, 1.549 mmol). The mixture was cooled to −35° C. and a solution of catechoborane/toluene (1.518 mL, 6.19 mmol) was added over 5 min. After 30 min, the reaction mixture was let it sit in a freezer for 5 days. Mixture was then diluted with EtOAc (100 mL) and sat. Na₂CO₃ (50 mL). The mixture was stirred vigorously for 30 min, and the organic phase washed with sat Na₂CO₃ (2×50 mL), dried (Na₂SO₄), filtered, concentrated and the residue was purified by silica gel chromatography (5-100% EtOAc/hexane) to afford desired (S)-methyl 4-(4,4-dimethylpiperidin-1-yl)-5-(1-hydroxy-2-methoxy-2-oxoethyl)-6-methylpyrazolo[1,5-a]pyridine-2-carboxylate (330 mg, 0.847 mmol, 27.4% yield) as off-white solid. ¹H NMR (500 MHz, CDCl₃) δ 8.28 (s, 1H), 7.21 (d, J=0.9 Hz, 1H), 6.73 (d, J=8.5 Hz, 1H), 5.50 (d, J=8.5 Hz, 1H), 4.06-4.02 (m, 3H), 3.80-3.74 (m, 3H), 3.60-3.50 (m, 1H), 3.46 (t, J=11.0 Hz, 1H), 2.88 (d, J=11.5 Hz, 1H), 2.69 (d, J=11.7 Hz, 1H), 2.43 (d, J=0.9 Hz, 3H), 1.85-1.67 (m, 2H), 1.54-1.41 (m, 2H), 1.17 (s, 3H), 1.09 (s, 3H). LCMS (M+H)=390.4.

Intermediate 15

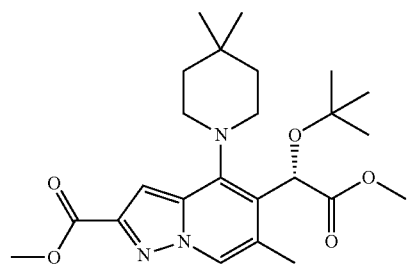

(S)-Methyl 5-(1-(tert-butoxy)-2-methoxy-2-oxo-ethyl)-4-(4,4-dimethylpiperidin-1-yl)-6-methylpyrazolo[1,5-a]pyridine-2-carboxylate To a stirred solution of (S)-methyl 4-(4,4-dimethylpiperidin-1-yl)-5-(1-hydroxy-2-methoxy-2-oxoethyl)-6-methylpyrazolo[1,5-a]pyridine-2-carboxylate (320 mg, 0.822 mmol) in fluorobenzene (8 mL) was added trifluoromethanesulfonimide (46.2 mg, 0.164 mmol) in CH$_2$Cl$_2$ (1 mL) and the mixture was heated at 40° C. tert-Butyl 2,2,2-trichloroacetimidate (3591 mg, 16.43 mmol) in fluorobenzene (2 mL) was then added and the flask was sealed and heated at 40° C. for 16 h. At this point, LCMS indicated approx 60% conversion so 2 g of tert-butyl 2,2,2-trichloroacetimidate and 20 mg of trifluoromethanesulfonimide was added and again flask was sealed and heated at 40° C. for 16 h. At this point, LCMS indicated completion of reaction. Mixture was then diluted with hexanes (50 mL) and solids were filtered off and washed with hexanes. The organic layer was washed with water, dried (Na$_2$SO$_4$), filtered and concentrated. The residue was purified via Biotage (0-40% EtOAc/hexane) to afford (S)-methyl 5-(1-(tert-butoxy)-2-methoxy-2-oxoethyl)-4-(4,4-dimethylpiperidin-1-yl)-6-methylpyrazolo[1,5-a]pyridine-2-carboxylate (300 mg, 0.673 mmol, 82% yield) as visdcous oil contaminated with trichloro acetamide. $^1$H NMR (500 MHz, CDCl$_3$) δ 8.18 (s, 1H), 7.26 (d, J=0.9 Hz, 1H), 6.43 (s, 1H), 4.03 (s, 3H), 3.72 (s, 3H), 3.67 (t, J=11.2 Hz, 1H), 3.32 (t, J=11.3 Hz, 1H), 2.98 (d, J=11.5 Hz, 1H), 2.82 (d, J=11.5 Hz, 1H), 2.37 (d, J=1.1 Hz, 3H), 1.76-1.61 (m, 2H), 1.53-1.40 (m, 2H), 1.26 (s, 9H), 1.16 (s, 3H), 1.08 (s, 3H). LCMS (M+H)=446.4.

Intermediate 16

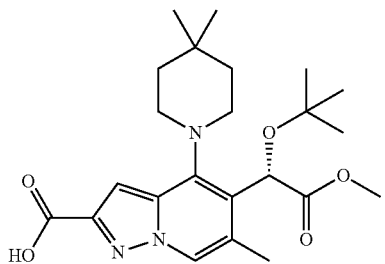 [SMILES: COC(=O)[C@@H](OC(C)(C)C)c1c(C)cn2nc(C(=O)O)cc2c1N1CCC(C)(C)CC1]

(S)-5-(1-(tert-Butoxy)-2-methoxy-2-oxoethyl)-4-(4,4-dimethylpiperidin-1-yl)-6-methylpyrazolo[1,5-a]pyridine-2-carboxylic acid To a solution of (S)-methyl 5-(1-(tert-butoxy)-2-methoxy-2-oxoethyl)-4-(4,4-dimethylpiperidin-1-yl)-6-methylpyrazolo[1,5-a]pyridine-2-carboxylate (300 mg, 0.673 mmol) in MeOH (6 mL) and THF (6 mL) was added 1N NaOH (0.741 mL, 0.741 mmol) and the resulting mixture was stirred at room temp for 16 h. Water was then added and the mixture was extracted with ether (10 mL). Ether layer was then discarded and aqueous layer was acidified with 1N HCl and extracted with ethyl acetate (25 mL), washed with brine (10 mL), dried (Na$_2$SO$_4$), filtered and concentrated to afford (S)-5-(1-(tert-butoxy)-2-methoxy-2-oxoethyl)-4-(4,4-dimethylpiperidin-1-yl)-6-methylpyrazolo[1,5-a]pyridine-2-carboxylic acid (280 mg, 0.649 mmol, 96% yield) as white foam, which was used in the next step without further purification. $^1$H NMR (500 MHz, CDCl$_3$) δ 8.26 (br. s., 1H), 7.37-7.32 (m, 1H), 6.42 (br. s., 1H), 3.74 (s, 3H), 3.70 (br. s., 1H), 3.33 (br. s., 1H), 3.00 (br. s., 1H), 2.85 (br. s., 1H), 2.41 (s, 3H), 1.73 (br. s., 1H), 1.75-1.44 (m, 4H), 1.27 (s, 9H), 1.17 (br. s., 3H), 1.09 (br. s., 3H). LCMS (M+H)=432.4.

Example 3

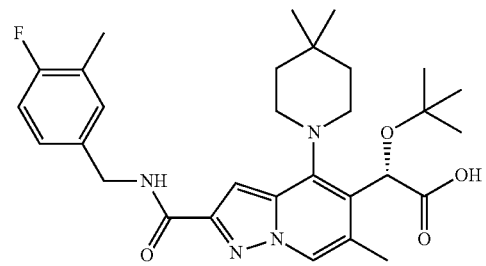 [SMILES: Cc1cc(CNC(=O)c2cc3c(N4CCC(C)(C)CC4)c([C@H](OC(C)(C)C)C(=O)O)c(C)cn3n2)ccc1F]

(S)-2-(tert-Butoxy)-2-(4-(4,4-dimethylpiperidin-1-yl)-2-((4-fluoro-3-methylbenzyl)carbamoyl)-6-methylpyrazolo[1,5-a]pyridin-5-yl)acetic acid To a solution of (S)-5-(1-(tert-butoxy)-2-methoxy-2-oxoethyl)-4-(4,4-dimethylpiperidin-1-yl)-6-methylpyrazolo[1,5-a]pyridine-2-carboxylic acid (30 mg, 0.070 mmol) and (4-fluoro-3-methylphenyl)methanamine (19.35 mg, 0.139 mmol) in DMF (1 mL) was added DIEA (0.061 mL, 0.348 mmol) followed by HATU (52.9 mg, 0.139 mmol) and DMAP (0.849 mg, 6.95 μmol) and the resulting mixture was stirred at room temp for 3 h. Water was then added and the mixture was extracted with ether (2×10 mL), washed with brine (10 mL), dried (Na$_2$SO$_4$), filtered and concentrated. The crude was then treated with 1N NaOH (0.348 mL, 0.348 mmol) in MeOH (3 mL) at 70° C. for 16 h. Mixture was then cooled and purified by prep HPLC to afford (S)-2-(tert-butoxy)-2-(4-(4,4-dimethylpiperidin-1-yl)-2-((4-fluoro-3-methylbenzyl)carbamoyl)-6-methylpyrazolo[1,5-a]pyridin-5-yl)acetic acid (20 mg, 0.037 mmol, 53.4% yield). $^1$H NMR (500 MHz, DMSO-d$_6$) δ 8.98 (t, J=6.0 Hz, 1H), 8.31 (s, 1H), 7.23 (d, J=7.9 Hz, 1H), 7.17 (br. s., 1H), 7.12 (s, 1H), 7.09-7.03 (m, 1H), 6.14 (s, 1H), 4.42 (d, J=6.1 Hz, 2H), 3.22-3.13 (m, 2H), 3.09 (br. s., 2H), 2.30 (s, 3H), 2.21 (s, 3H), 1.62 (d, J=9.8 Hz, 1H), 1.55 (d, J=11.3 Hz, 1H), 1.51-1.43 (m, 1H), 1.39 (d, J=13.4 Hz, 1H), 1.16 (s, 9H), 1.10 (s, 3H), 1.01 (s, 3H). LCMS (M+H)=539.5.

Intermediate 17

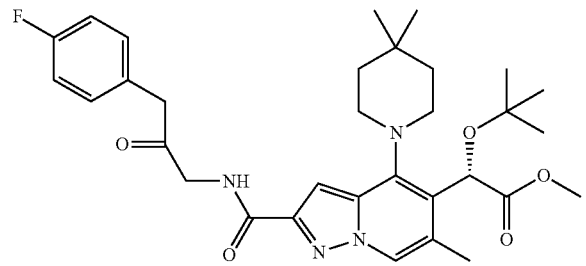 [SMILES: COC(=O)[C@@H](OC(C)(C)C)c1c(C)cn2nc(C(=O)NCC(=O)Cc3ccc(F)cc3)cc2c1N1CCC(C)(C)CC1]

(S)-Methyl 2-(tert-butoxy)-2-(4-(4,4-dimethylpiperidin-1-yl)-2-((3-(4-fluorophenyl)-2-oxopropyl)carbamoyl)-6-methylpyrazolo[1,5-a]pyridin-5-yl)acetate To a solution of (S)-5-(1-(tert-butoxy)-2-methoxy-2-oxoethyl)-4-(4,4-dimethylpiperidin-1-yl)-6-methylpyrazolo[1,5-a]pyridine-2-carboxylic acid (270 mg, 0.626 mmol) in CH$_2$Cl$_2$ (5 mL) was added oxalyl chloride (0.060 mL, 0.688 mmol) few drops of DMF was then added and the mixture was stirred at room temp for 1 h. The crude acid chloride was then added to a pre-stirred solution of 1-amino-3-(4-fluorophenyl)propan-2-one•HCl (191 mg, 0.939 mmol) and DIEA (0.656 mL, 3.75 mmol) in CH$_2$Cl$_2$ (5.00 mL) and the resulting solution was stirred at room temperature for 16 h. Water was then added and the mixture was extracted with CH$_2$Cl$_2$, dried (Na$_2$SO$_4$), filtered and concentrated. The crude was then purified by flash column chromatograpgy on silica gel column using (5-70% EtOAc/Hexane as eluant) to afford (S)-methyl 2-(tert-butoxy)-2-(4-(4,4-dimethylpiperidin-1-yl)-2-((3-(4-fluorophenyl)-2-oxopropyl)carbamoyl)-6-methylpyrazolo[1,5-a]pyridin-5-yl)acetate (200 mg, 0.344 mmol, 55.0% yield) as light yellow solid. $^1$H NMR (500 MHz, CDCl$_3$) δ 8.07 (s, 1H), 7.69 (t, J=4.9 Hz, 1H), 7.27-7.24 (m, 2H), 7.23-7.20 (m, 1H), 7.11-7.04 (m, 2H), 6.44 (s, 1H), 4.42 (d, J=5.0 Hz, 2H), 3.82 (s, 2H), 3.71 (s, 3H), 3.70-3.64 (m, 1H), 3.31 (t, J=11.3 Hz, 1H), 2.95 (d, J=12.0 Hz, 1H), 2.79 (d, J=11.7 Hz, 1H), 2.37 (d, J=0.9 Hz, 3H), 1.75-1.61 (m, 2H), 1.54-1.40 (m, 2H), 1.25 (s, 9H), 1.14 (s, 3H), 1.06 (s, 3H). LCMS (M+H)=582.5.

Example 4

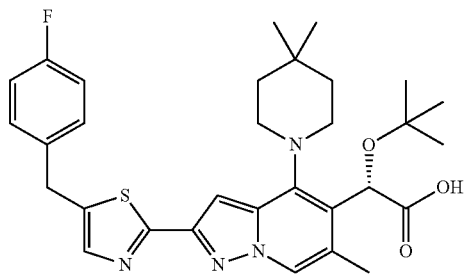 [SMILES: Cc1cn2nc(-c3ncc(Cc4ccc(F)cc4)s3)cc2c(N2CCC(C)(C)CC2)c1[C@H](OC(C)(C)C)C(=O)O]

(S)-2-(tert-Butoxy)-2-(4-(4,4-dimethylpiperidin-1-yl)-2-(5-(4-fluorobenzyl)thiazol-2-yl)-6-methylpyrazolo[1,5-a]pyridin-5-yl)acetic acid To a solution of (S)-methyl 2-(tert-butoxy)-2-(4-(4,4-dimethylpiperidin-1-yl)-2-((3-(4-fluorophenyl)-2-oxopropyl)carbamoyl)-6-methylpyrazolo[1,5-a]pyridin-5-yl)acetate (50 mg, 0.086 mmol) in toluene was added Lawesson's Reagent (38.3 mg, 0.095 mmol) and stir for 15 min at rt, 1 h at 60° C. 2 h. At this point LCMS indicated completion of reaction and appearance of desired product. Mixture was then cooled, concentrated and treated with 1N NaOH (0.258 mL, 0.258 mmol) in MeOH (3 mL) at 70° C. for 4 h. Mixture was then cooled and purified by prep HPLC to afford (S)-2-(tert-butoxy)-2-(4-(4,4-dimethylpiperidin-1-yl)-2-(5-(4-fluorobenzyl)thiazol-2-yl)-6-methylpyrazolo[1,5-a]pyridin-5-yl)acetic acid (35 mg, 0.062 mmol, 72.0% yield). $^1$H NMR (500 MHz, DMSO-d$_6$) δ 8.35 (s, 1H), 7.73 (s, 1H), 7.36 (dd, J=8.1, 5.6 Hz, 2H), 7.16 (t, J=8.7 Hz, 2H), 7.10 (s, 1H), 6.13 (s, 1H), 4.24 (s, 2H), 3.24-3.17 (m, 2H), 3.08 (br. s., 2H), 2.27 (s, 3H), 1.68-1.51 (m, 2H), 1.49-1.43 (m, 1H), 1.39 (d, J=12.5 Hz, 1H), 1.16 (s, 9H), 1.10 (s, 3H), 1.00 (s, 3H). LCMS (M+H)=565.4.

Example 5

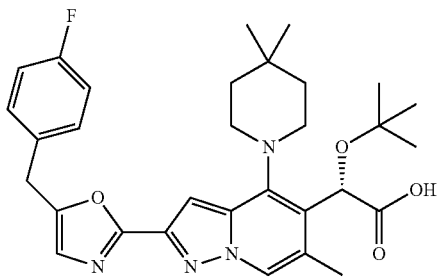 [SMILES: Cc1cn2nc(-c3ncc(Cc4ccc(F)cc4)o3)cc2c(N2CCC(C)(C)CC2)c1[C@H](OC(C)(C)C)C(=O)O]

(S)-2-(tert-Butoxy)-2-(4-(4,4-dimethylpiperidin-1-yl)-2-(5-(4-fluorobenzyl)oxazol-2-yl)-6-methylpyrazolo[1,5-a]pyridin-5-yl)acetic acid: To a solution of (S)-methyl 2-(tert-butoxy)-2-(4-(4,4-dimethylpiperidin-1-yl)-2-((3-(4-fluorophenyl)-2-oxopropyl)carbamoyl)-6-methylpyrazolo[1,5-a]pyridin-5-yl)acetate (50 mg, 0.086 mmol) in THF (2 mL) was added Burgess reagent (61.6 mg, 0.258 mmol) and the mixture was heated at 80° C. for 1 h. At this point LCMS indicated completion of reaction and appearance of desired product. Mixture was then cooled, concentrated and treated with 1N NaOH (0.258 mL, 0.258 mmol) in MeOH (3 mL) at 70° C. for 4 h. Mixture was then cooled and purified by prep HPLC to afford (S)-2-(tert-butoxy)-2-(4-(4,4-dimethylpiperidin-1-yl)-2-(5-(4-fluorobenzyl)oxazol-2-yl)-6-methylpyrazolo[1,5-a]pyridin-5-yl)acetic acid (30 mg, 0.055 mmol, 63.5% yield). $^1$H NMR (500 MHz, DMSO-d$_6$) δ 8.39 (s, 1H), 7.41-7.31 (m, 2H), 7.18 (t, J=8.9 Hz, 2H), 7.08 (s, 1H), 7.12 (s, 1H), 6.14 (s, 1H), 4.15 (s, 2H), 3.22-3.16 (m, 2H), 3.07 (br. s., 2H), 2.28 (s, 3H), 1.62 (d, J=7.9 Hz, 1H), 1.54 (d, J=9.2 Hz, 1H), 1.50-1.43 (m, 1H), 1.39 (d, J=11.9 Hz, 1H), 1.16 (s, 9H), 1.10 (s, 3H), 1.01 (s, 3H). LCMS 4 (M+H)=549.5.

The following examples could be prepared according to the procedures describe above examples.

Example 6

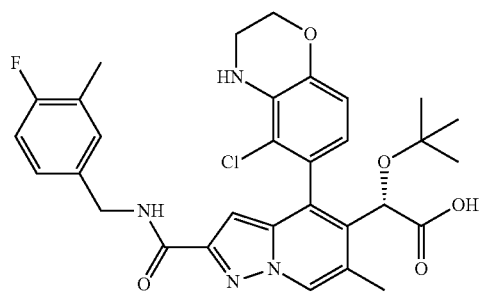 [SMILES: Cc1cc(CNC(=O)c2cc3c(-c4ccc5c(c4Cl)NCCO5)c([C@H](OC(C)(C)C)C(=O)O)c(C)cn3n2)ccc1F]

37

(2S)-2-(tert-Butoxy)-2-(4-(5-chloro-3,4-dihydro-2H-benzo[b][1,4]oxazin-6-yl)-2-((4-fluoro-3-methylbenzyl)carbamoyl)-6-methylpyrazolo[1,5-a]pyridin-5-yl)acetic acid Example 7

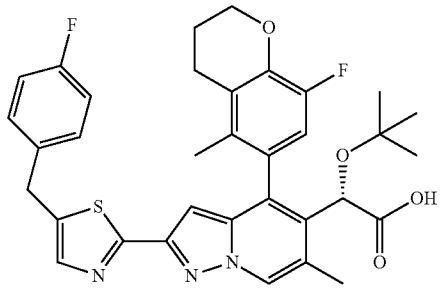

(2S)-2-(tert-Butoxy)-2-(4-(8-fluoro-5-methylchroman-6-yl)-2-(5-(4-fluorobenzyl)thiazol-2-yl)-6-methylpyrazolo[1,5-a]pyridin-5-yl)acetic acid Example 8

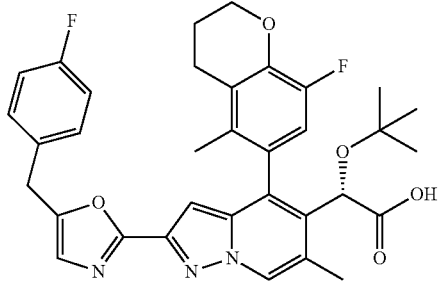 [SMILES: Cc1cn2nc(-c3ncc(Cc4ccc(F)cc4)o3)cc2c(-c2cc(F)c3c(c2C)CCCO3)c1[C@H](OC(C)(C)C)C(=O)O]

(2S)-2-(tert-Butoxy)-2-(4-(8-fluoro-5-methylchroman-6-yl)-2-(5-(4-fluorobenzyl)oxazol-2-yl)-6-methylpyrazolo[1,5-a]pyridin-5-yl)acetic acid Example 9

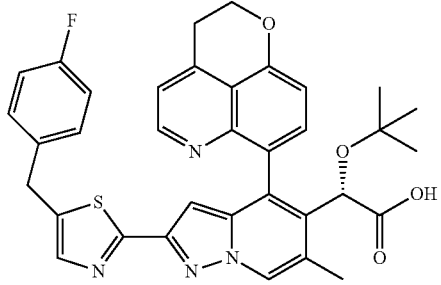 [SMILES: Cc1cn2nc(-c3ncc(Cc4ccc(F)cc4)o3)cc2c(-c2ccc3c4c(ccnc24)CCO3)c1[C@H](OC(C)(C)C)C(=O)O]

38

(2S)-2-(tert-Butoxy)-2-(4-(2,3-dihydropyrano[4,3,2-de]quinolin-7-yl)-2-(5-(4-fluorobenzyl)thiazol-2-yl)-6-methylpyrazolo[1,5-a]pyridin-5-yl)acetic acid Example 10

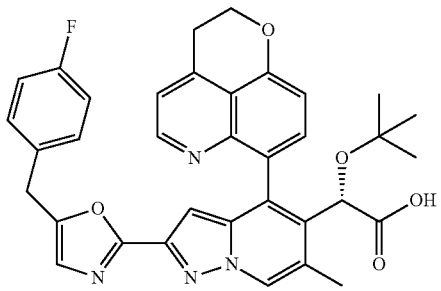

(2S)-2-(tert-Butoxy)-2-(4-(2,3-dihydropyrano[4,3,2-de]quinolin-7-yl)-2-(5-(4-fluorobenzyl)oxazol-2-yl)-6-methylpyrazolo[1,5-a]pyridin-5-yl)acetic acid Example 11

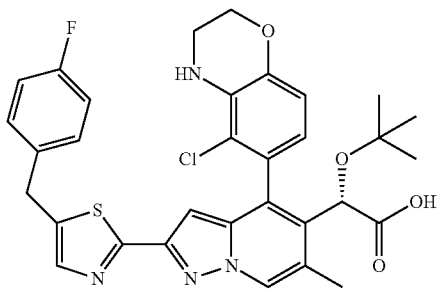 [SMILES: Cc1cn2nc(-c3ncc(Cc4ccc(F)cc4)o3)cc2c(-c2ccc3c(c2Cl)NCCO3)c1[C@H](OC(C)(C)C)C(=O)O]

(2S)-2-(tert-Butoxy)-2-(4-(5-chloro-3,4-dihydro-2H-benzo[b][1,4]oxazin-6-yl)-2-(5-(4-fluorobenzyl)thiazol-2-yl)-6-methylpyrazolo[1,5-a]pyridin-5-yl)acetic acid Example 12

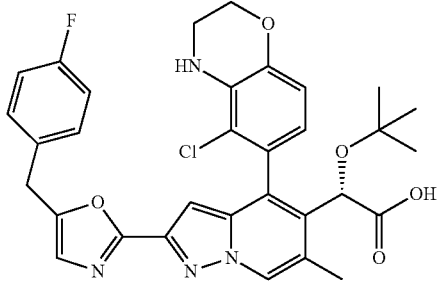

(2S)-2-(tert-Butoxy)-2-(4-(5-chloro-3,4-dihydro-2H-benzo[b][1,4]oxazin-6-yl)-2-(5-(4-fluorobenzyl)oxazol-2-yl)-6-methylpyrazolo[1,5-a]pyridin-5-yl)acetic acid Intermediate 18

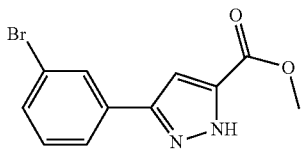 [SMILES: COC(=O)c1cc(-c2cccc(Br)c2)n[nH]1]

Methyl 3-(3-bromophenyl)-1H-pyrazole-5-carboxylate

A cold (0° C.) solution of 1-(3-bromophenyl)ethanone (15.23 g, 75 mmol) and dimethyl oxalate (8.86 g, 75 mmol) in dry DMF (25 mL) was treated with sodium hydride, 60% oil disp. (3.60 g, 90 mmol) portion-wise over 30 min. The reaction was diluted with additional DMF (50 mL), stirred for 20 min then stirred at room temperature for 16 hrs. The reaction was treated with glacial acetic acid (10.3 mL, 180 mmol) by slow addition, and then stirred for 5 min. The mixture was then treated with hydrazine monohydrate (4.09 mL, 83 mmol), stirred for 30 min then diluted with EtOAc (200 mL), water (200 mL) and brine. The mixture was filtered to remove solids and the filtrate layers were separated. The organic layer was concentrated and stored at 4° C. for 16 hrs. The crude reaction mixture was diluted with water, and stirred vigorously for 30 min, and then decanted and resulting solids were washed with additional water, collecting by vacuum filtration. The solids were stirred with acetonitrile for 15 min, and then collected by vacuum filtration, washing with several small portions of acetonitrile. The tan powder was dried under vacuum pump for 16 hrs, affording the expected product (9.74 g, 34.6 mmol, 46.2% yield). $^1$H NMR (500 MHz, CDCl$_3$) δ: 7.98 (t, J=1.7 Hz, 1H), 7.72 (dt, J=7.7, 1.3 Hz, 1H), 7.53-7.48 (m, 1H), 7.32 (t, J=7.9 Hz, 1H), 7.14 (s, 1H), 3.98 (s, 3H). LCMS (M+H)=281/283.

Intermediate 19

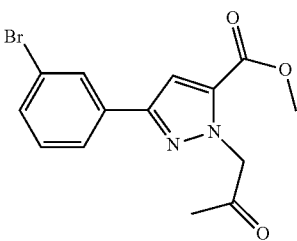 [SMILES: COC(=O)c1cc(-c2cccc(Br)c2)nn1CC(C)=O]

Methyl 3-(3-bromophenyl)-1-(2-oxopropyl)-1H-pyrazole-5-carboxylate

To a stirred suspension of methyl 3-(3-bromophenyl)-1H-pyrazole-5-carboxylate (4.45 g, 15.83 mmol) in DMF (45 mL) was added KOtBu (1.865 g, 16.62 mmol) in one portion. After 20 min, the reaction mixture was placed in a cool water bath (20° C.) and 1-chloropropan-2-one (1.389 mL, 17.41 mmol) was added over 1 min. The reaction was stirred for 4 hrs, then diluted with Et$_2$O (150 mL), washed with 1.0 N HCl (75 mL), brine (50 mL), then dried (MgSO$_4$), filtered and concentrated. The resultant slurry was collected by filtration and dried to afford the expected product (2.09 g, 6.2 mmol, 39.2% yield) as a yellow solid. $^1$H NMR (500 MHz, CDCl$_3$) δ: 7.97 (t, J=1.8 Hz, 1H), 7.71 (dt, J=7.8, 1.3 Hz, 1H), 7.47 (ddd, J=8.0, 1.9, 0.9 Hz, 1H), 7.30-7.27 (m, 1H), 7.19 (s, 1H), 5.40 (s, 2H), 3.89 (s, 3H), 2.25 (s, 3H). LCMS (M+H)=339.1.

Intermediate 20

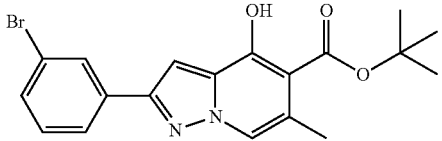 [SMILES: Cc1cn2nc(-c3cccc(Br)c3)cc2c(O)c1C(=O)OC(C)(C)C]

tert-Butyl 2-(3-bromophenyl)-4-hydroxy-6-methyl-pyrazolo[1,5-a]pyridine-5-carboxylate A cold (0° C.) solution of methyl 3-(3-bromophenyl)-1-(2-oxopropyl)-1H-pyrazole-5-carboxylate (2.09 g, 6.20 mmol) in dry DMF (12.40 ml) was treated with tert-butyl 2-(diethoxyphosphoryl)acetate (1.674 ml, 7.13 mmol) followed by KOtBu (1.461 g, 13.02 mmol) over several minutes. The reaction was stirred for 5 min, and then warmed to room temperature. The reaction was stirred for 3 hrs, then diluted with Et$_2$O (75 mL), washed with 1.0 N HCl (75 mL), brine (50 mL), dried (MgSO$_4$), filtered and concentrated. The residue was purified by biotage (120 g SiO$_2$, 0% (3 CV), 0-50% (15 CV), 60% (2 CV), EtOAc in hexanes), affording the desired product (1.98 g, 4.91 mmol, 79% yield) as a white solid. $^1$H NMR (500 MHz, CDCl$_3$) δ: 12.88 (s, 1H), 8.13 (t, J=1.8 Hz, 1H), 7.87 (dq, J=7.8, 0.8 Hz, 1H), 7.84-7.78 (m, 1H), 7.49 (ddd, J=8.0, 2.0, 1.1 Hz, 1H), 7.32 (t, J=7.9 Hz, 1H), 7.12 (d, J=0.8 Hz, 1H), 2.47 (d, J=1.1 Hz, 3H), 1.67 (s, 9H). LCMS (M+H)=405.2.

Intermediate 21

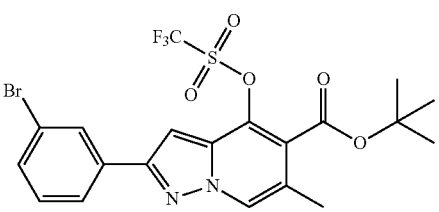 [SMILES: Cc1cn2nc(-c3cccc(Br)c3)cc2c(OS(=O)(=O)C(F)(F)F)c1C(=O)OC(C)(C)C]

tert-Butyl 2-(3-bromophenyl)-6-methyl-4-(((trifluoromethyl)sulfonyl)oxy)pyrazolo[1,5-a]pyridine-5-carboxylate To a cold (−78° C. dry ice/acetone bath) stirred solution of tert-butyl 2-(3-bromophenyl)-4-hydroxy-6-methylpyrazolo[1,5-a]pyridine-5-carboxylate (4.50 g, 11.16 mmol) in CH$_2$Cl$_2$ (100 ml) was added Et$_3$N (2.0 ml, 14.35 mmol), followed by 1.0 M triflic anhydride in CH$_2$Cl$_2$ (2.074 ml, 12.27 mmol) over 5 min. The reaction was stirred for 30 min, then was quenched with 1M NH$_4$Cl (50 mL). The layers were separated and the aq. layer was extracted with CH$_2$Cl$_2$ (50 mL). The combined organic layers were dried (MgSO$_4$), filtered and concentrated. The crude was then triturated with ethyl acetate/hexane, and the solids were filtered and dried to afford the desired product (5.450 g, 10.18 mmol, 91% yield) as a white solid from two combined crops. $^1$H NMR (500 MHz, CDCl3) δ: 8.32 (t, J=0.9 Hz, 1H), 8.11 (t, J=1.7 Hz, 1H), 7.87 (dq, J=7.7, 0.9 Hz, 1H), 7.54 (ddd, J=8.0, 2.0, 1.0 Hz, 1H), 7.34 (t, J=7.9 Hz, 1H), 6.96 (s, 1H), 2.43 (d, J=1.1 Hz, 3H), 1.65 (s, 9H). LCMS (M+H)=537.2.

Intermediate 22

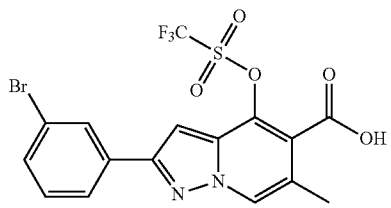 [SMILES: Cc1cn2nc(-c3cccc(Br)c3)cc2c(OS(=O)(=O)C(F)(F)F)c1C(=O)O]

2-(3-Bromophenyl)-6-methyl-4-(((trifluoromethyl)sulfonyl)oxy)pyrazolo[1,5-a]pyridine-5-carboxylic acid To a stirred solution of tert-butyl 2-(3-bromophenyl)-6-methyl-4-(((trifluoromethyl)sulfonyl)oxy)pyrazolo[1,5-a]pyridine-5-carboxylate (5.45 g, 10.18 mmol) in CH$_2$Cl$_2$ (60 mL) was added TFA (40 mL) at room temperature. The reaction was stirred for 5.5 hrs, then concentrated and the resulting solid was triturated with ethyl acetate/hexane then collected by vacuum filtration and rinsed with hexane to afford the desired product (4.85 g, 10.12 mmol, 99% yield) as a white powdery solid. $^1$H NMR (500 MHz, d$_6$-DMSO) δ: 14.53 (br. s., 1H), 8.93-8.89 (m, 1H), 8.26 (t, J=1.8 Hz, 1H), 8.09-8.04 (m, 1H), 7.64 (ddd, J=8.0, 2.0, 1.0 Hz, 1H), 7.47 (t, J=7.9 Hz, 1H), 7.34 (s, 1H), 2.39 (d, J=1.1 Hz, 3H). LC/MS (M+H)=481.1.

Intermediate 23

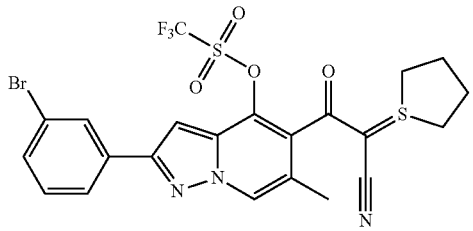 [SMILES: Cc1cn2nc(-c3cccc(Br)c3)cc2c(OS(=O)(=O)C(F)(F)F)c1C(=O)C(C#N)=S1CCCC1]

2-(3-Bromophenyl)-5-{2-cyano-2-[(1E)-1λ$^4$-thiolan-1-ylidene]acetyl}-6-methylpyrazolo[1,5-a]pyridin-4-yl trifluoromethanesulfonate To a suspension of 2-(3-bromophenyl)-6-methyl-4-4-(((trifluoromethyl)sulfonyl)oxy)pyrazolo[1,5-a]pyridine-5-carboxylic acid (4.85 g, 10.12 mmol) in CH$_2$Cl$_2$ (100 mL) was added oxalyl chloride (1.329 mL, 15.18 mmol) followed by a few drops of DMF. The resulting suspension was stirred at room temp for 1 hr, then concentrated to a yellow powdery solid, and re-dissolved in CH$_2$Cl$_2$. The solution was treated with 1-(cyanomethyl)tetrahydro-1H-thiophen-1-ium, bromide salt (3.16 g, 15.18 mmol) followed by Hunig's Base (5.30 ml, 30.4 mmol) at room temperature. The reaction was stirred for 90 min, then diluted with EtOAc (75 mL), washed with 1.0 N HCl (50 mL), water (50 mL), then brine (50 mL). The organic layer was dried (MgSO$_4$), filtered, and concentrated to afford an amber semi-solid, which was used immediately in the following step. LCMS (M+H)=590.1.

Intermediate 24

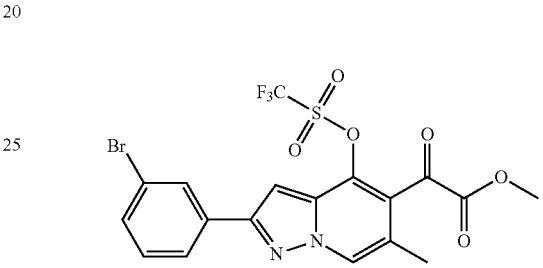

Methyl 2-(2-(3-bromophenyl)-6-methyl-4-(((trifluoromethyl)sulfonyl)oxy)pyrazolo[1,5-a]pyridin-5-yl)-2-oxoacetate To a stirred solution of 2-(3-bromophenyl)-5-{2-cyano-2-[(1E)-1λ$^4$-thiolan-1-ylidene]acetyl}-6-methylpyrazolo[1,5-a]pyridin-4-yl trifluoromethanesulfonate (5.95 g, 10.12 mmol) in MeOH (50 mL) and DMF (50 mL) was added a solution of oxone (12.44 g, 20.24 mmol) in water (100 mL) at room temperature. The resulting suspension was stirred at room temperature for 40 hrs. The reaction was treated with additional oxone (6.25 g, 10.17 mmol) and stirred for 4.5 hrs. The reaction mixture was then diluted with ethyl acetate (250 mL), the layers were separated and organic layer was washed with water (2×100 mL), brine (100 mL), dried (MgSO$_4$), filtered and concentrated, affording an orange oil which solidified upon standing. This was dissolved in CH$_2$Cl$_2$ (50 mL) and MeOH (15 mL) and then treated with TMS-diazomethane, 2.0 M in hexanes (2.0 mL, 4.00 mmol) and stirred for 30 min at room temperature. The reaction was concentrated and the resultant residue was purified by biotage (330 g SiO$_2$, 0% (3 CV), 0-50% (15 CV), 50% (2 CV), EtOAc in hexanes). Product fractions were pooled and concentrated under reduced pressure, affording the desired product (4.18 g, 8.02 mmol, 79% yield) as a yellow solid. LC/MS (M+H)=523.1.

The examples 13-20 could be prepared using methyl 2-(2-(3-bromophenyl)-6-methyl-4-(((trifluoromethyl)sulfonyl)oxy)pyrazolo[1,5-a]pyridin-5-yl)-2-oxoacetate and by following procedures for examples 1-12 or conditions well known in the art.

Example 13

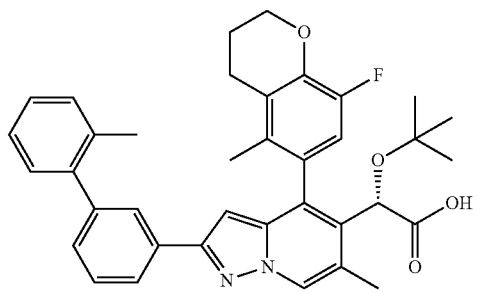 [SMILES: Cc1ccccc1-c1cccc(-c2cc3c(-c4cc(F)c5c(c4C)CCCO5)c([C@H](OC(C)(C)C)C(=O)O)c(C)cn3n2)c1]

(2S)-2-(tert-Butoxy)-2-(4-(8-fluoro-5-methylchroman-6-yl)-6-methyl-2-(2'-methyl-[1,1'-biphenyl]-3-yl)pyrazolo[1,5-a]pyridin-5-yl)acetic acid

Example 14

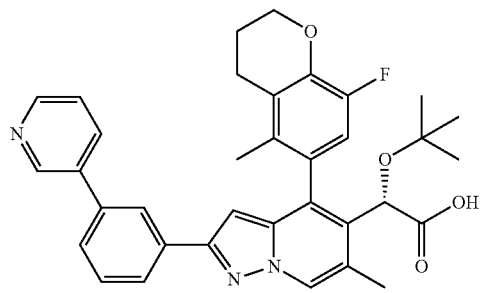 [SMILES: Cc1cn2nc(-c3cccc(-c4cccnc4)c3)cc2c(-c2cc(F)c3c(c2C)CCCO3)c1[C@H](OC(C)(C)C)C(=O)O]

(2S)-2-(tert-Butoxy)-2-(4-(8-fluoro-5-methylchroman-6-yl)-6-methyl-2-(3-(pyridin-3-yl)phenyl)pyrazolo[1,5-a]pyridin-5-yl)acetic acid

Example 15

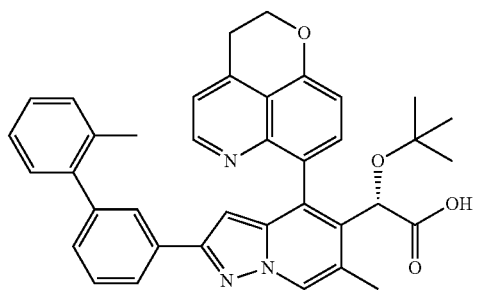 [SMILES: Cc1ccccc1-c1cccc(-c2cc3c(-c4ccc5c6c(ccnc46)CCO5)c([C@H](OC(C)(C)C)C(=O)O)c(C)cn3n2)c1]

(2S)-2-(tert-Butoxy)-2-(4-(2,3-dihydropyrano[4,3,2-de]quinolin-7-yl)-6-methyl-2-(2'-methyl-[1,1'-biphenyl]-3-yl)pyrazolo[1,5-a]pyridin-5-yl)acetic acid

Example 16

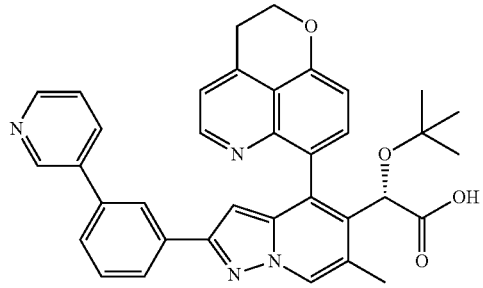 [SMILES: Cc1cn2nc(-c3cccc(-c4cccnc4)c3)cc2c(-c2ccc3c4c(ccnc24)CCO3)c1[C@H](OC(C)(C)C)C(=O)O]

(2S)-2-(tert-Butoxy)-2-(4-(2,3-dihydropyrano[4,3,2-de]quinolin-7-yl)-6-methyl-2-(3-(pyridin-3-yl)phenyl)pyrazolo[1,5-a]pyridin-5-yl)acetic acid

Example 17

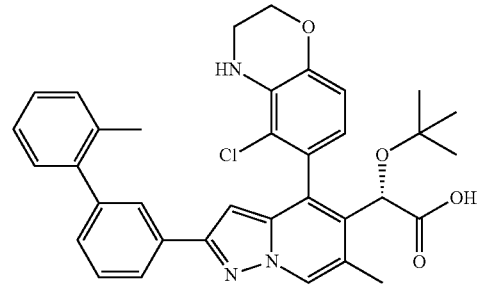 [SMILES: Cc1ccccc1-c1cccc(-c2cc3c(-c4ccc5c(c4Cl)NCCO5)c([C@H](OC(C)(C)C)C(=O)O)c(C)cn3n2)c1]

(2S)-2-(tert-Butoxy)-2-(4-(5-chloro-3,4-dihydro-2H-benzo[b][1,4]oxazin-6-yl)-6-methyl-2-(2'-methyl-[1,1'-biphenyl]-3-yl)pyrazolo[1,5-a]pyridin-5-yl)acetic acid

Example 18

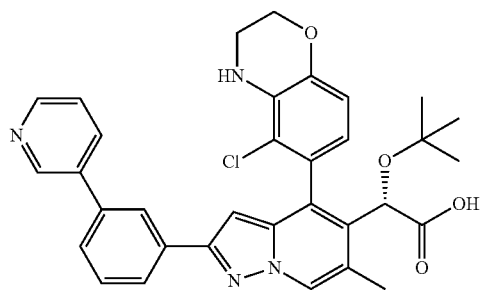 [SMILES: Cc1cn2nc(-c3cccc(-c4cccnc4)c3)cc2c(-c2ccc3c(c2Cl)NCCO3)c1[C@H](OC(C)(C)C)C(=O)O]

45

(2S)-2-(tert-Butoxy)-2-(4-(5-chloro-3,4-dihydro-2H-benzo[b][1,4]oxazin-6-yl)-6-methyl-2-(3-(pyridin-3-yl)phenyl)pyrazolo[1,5-a]pyridin-5-yl)acetic acid Example 19

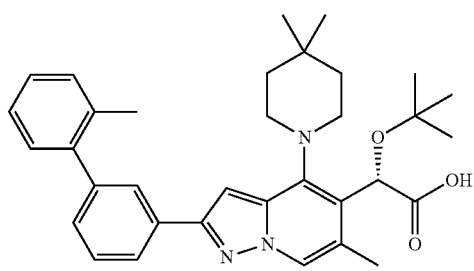 [SMILES: Cc1ccccc1-c1cccc(-c2cc3c(N4CCC(C)(C)CC4)c([C@H](OC(C)(C)C)C(=O)O)c(C)cn3n2)c1]

(S)-2-(tert-Butoxy)-2-(4-(4,4-dimethylpiperidin-1-yl)-6-methyl-2-(2'-methyl-[1,1'-biphenyl]-3-yl)pyrazolo[1,5-a]pyridin-5-yl)acetic acid Example 20

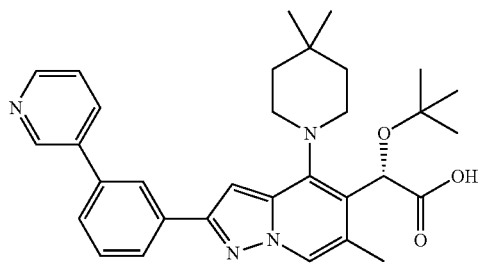 [SMILES: Cc1cn2nc(-c3cccc(-c4cccnc4)c3)cc2c(N2CCC(C)(C)CC2)c1[C@H](OC(C)(C)C)C(=O)O]

(S)-2-(tert-Butoxy)-2-(4-(4,4-dimethylpiperidin-1-yl)-6-methyl-2-(3-(pyridin-3-yl)phenyl)pyrazolo[1,5-a]pyridin-5-yl)acetic acid Example 21

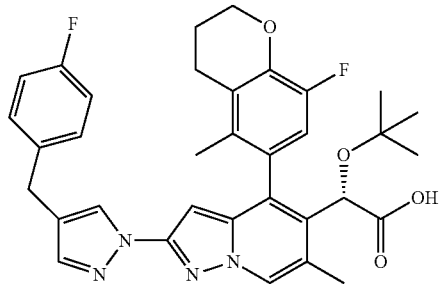 [SMILES: Cc1cn2nc(-n3cc(Cc4ccc(F)cc4)cn3)cc2c(-c2cc(F)c3c(c2C)CCCO3)c1[C@H](OC(C)(C)C)C(=O)O]

46

(2S)-2-(tert-Butoxy)-2-(4-(8-fluoro-5-methylchroman-6-yl)-2-(4-(4-fluorobenzyl)-1H-pyrazol-1-yl)-6-methylpyrazolo[1,5-a]pyridin-5-yl)acetic acid Example 22

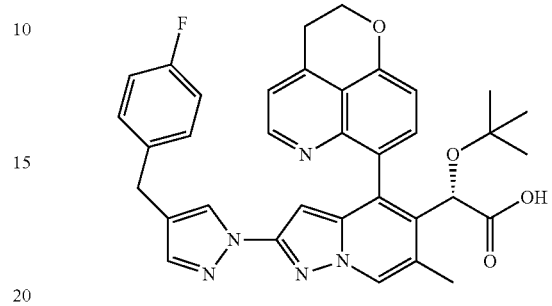

(2S)-2-(tert-Butoxy)-2-(4-(2,3-dihydropyrano[4,3,2-de]quinolin-7-yl)-2-(4-(4-fluorobenzyl)-1H-pyrazol-1-yl)-6-methylpyrazolo[1,5-a]pyridin-5-yl)acetic acid Example 23

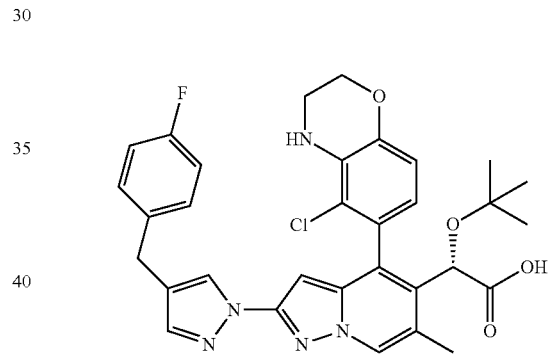

(2S)-2-(tert-Butoxy)-2-(4-(5-chloro-3,4-dihydro-2H-benzo[b][1,4]oxazin-6-yl)-2-(4-(4-fluorobenzyl)-1H-pyrazol-1-yl)-6-methylpyrazolo[1,5-a]pyridin-5-yl)acetic acid Example 24

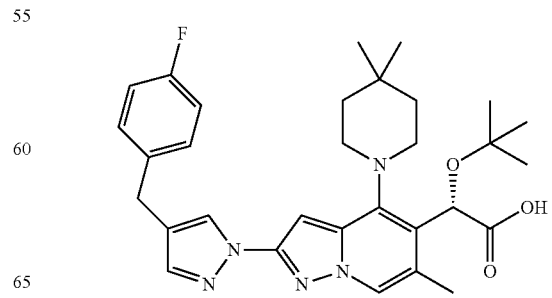

(S)-2-(tert-Butoxy)-2-(4-(4,4-dimethylpiperidin-1-yl)-2-(4-(4-fluorobenzyl)-1H-pyrazol-1-yl)-6-methylpyrazolo[1,5-a]pyridin-5-yl)acetic acid Intermediate 25

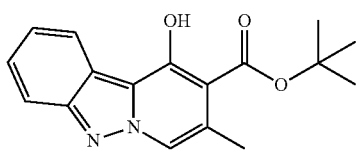 [SMILES: Cc1cn2nc3ccccc3c2c(O)c1C(=O)OC(C)(C)C]

tert-Butyl 10-hydroxy-8-methylpyrido[1,2-b]indazole-9-carboxylate

To a stirred solution of methyl 1H-indazole-3-carboxylate (10 g, 56.8 mmol) in DMF (100 mL) was added powder KOtBu (6.69 g, 59.6 mmol) ar rt. After 45 min, the reaction mixture was cooled in water bath (15° C.) and 1-chloropropan-2-one (4.98 ml, 62.4 mmol) was added over 3 min. Note: During the addition of chloroacetone, the gray reaction mixture turned dark brown to burgundy red (copper red) to light brown. After 1 h, tert-butyl 2-(diethoxyphosphoryl)acetate (16.00 ml, 68.1 mmol) was added at once followed by KOtBu (14.01 g, 125 mmol) over 2 min. After 30 min, water bath was removed and stirred for 2 h at rt, then diluted with ether (150 mL), washed with 1M HCl (70 mL), water (3×50 mL), brine (50 mL), dried (MgSO$_4$), filtered and concentrated to give brown oil which was purified by flash chromatography using 10 and 15% EtOAc/Hex to afford tert-butyl 10-hydroxy-8-methylpyrido[1,2-b]indazole-9-carboxylate (0.97 g) contaminated with impurities. LCMS (M+H)=299.15.

Intermediate 26

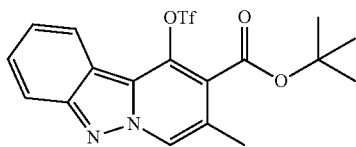 [SMILES: Cc1cn2nc3ccccc3c2c(OS(=O)(=O)C(F)(F)F)c1C(=O)OC(C)(C)C]

tert-Butyl 8-methyl-10-(((trifluoromethyl)sulfonyl)oxy)pyrido[1,2-b]indazole-9-carboxylate To a stirred solution of tert-butyl 10-hydroxy-8-methylpyrido[1,2-b]indazole-9-carboxylate (0.97 g) and Et$_3$N (0.836 ml, 6 mmol) in CH$_2$Cl$_2$ (10 mL) was added Tf$_2$O (0.676 ml, 4 mmol) at −78 C. After 2 h, the reaction mixture was diluted with ether (100 mL), washed with water (10 mL), 1M HCl (10 mL) and brine (10 mL), dried (MgSO$_4$), filtered, concentrated and purified by flash chromatography using 10 and 15% EtOAc/Hex to afford tert-butyl 8-methyl-10-(((trifluoromethyl)sulfonyl)oxy)pyrido[1,2-b]indazole-9-carboxylate (0.466 g, 1.083 mmol, 1.907% yield over two steps) as pale yellow solid and contaminated with impurities. $^1$H NMR (400 MHz, CDCl$_3$) δ 8.62 (d, J=1.3 Hz, 1H), 8.24 (d, J=8.8 Hz, 1H), 7.90 (td, J=0.8, 8.7 Hz, 1H), 7.61-7.66 (m, 1H), 7.37 (ddd, J=0.8, 6.9, 8.4 Hz, 1H), 2.61 (d, J=1.0 Hz, 3H), 1.68 (s, 9H). LCMS (M+H)=431.1.

Intermediate 27

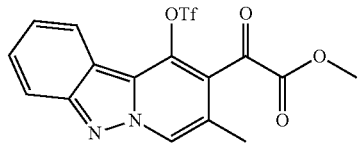 [SMILES: COC(=O)C(=O)c1c(C)cn2nc3ccccc3c2c1OS(=O)(=O)C(F)(F)F]

Methyl 2-(8-methyl-10-(((trifluoromethyl)sulfonyl)oxy)pyrido[1,2-b]indazol-9-yl)-2-oxoacetate To a stirred solution of tert-butyl 8-methyl-10-(((trifluoromethyl)sulfonyl)oxy)pyrido[1,2-b]indazole-9-carboxylate (0.46 g, 1.069 mmol) in CH$_2$Cl$_2$ (5 mL) was added TFA (2.5 mL) at rt. After 8 h, the reaction mixture was concentrated and resulting residue was used in the next step without purification. LCMS (M+H)=375.05.

To a stirred solution of above crude carboxylic acid in CH$_2$Cl$_2$ (10 mL), contains cat DMF) was added 2M oxalyl chloride/CH$_2$Cl$_2$ (1.069 ml, 2.138 mmol) at rt. After 2 h, the reaction mixture was concentrated and the resulting dark residue was used in the next step without purification.

To a stirred dark solution of crude acid chloride (0.420 g, 1.069 mmol) and 1-(cyanomethyl)tetrahydro-1H-thiophen-1-ium, bromide salt (0.334 g, 1.604 mmol) in CH$_2$Cl$_2$ (5 mL) was added DIEA (0.560 ml, 3.21 mmol) at once at at rt. After 2 h, the reaction mixture was diluted with EtOAc (50 mL), washed with 1M HCl (5 mL), water (10 mL), brine (10 mL), dried (MgSO$_4$), filtered and concentrated to give 1-(1-cyano-2-(8-methyl-10-(((trifluoromethyl)sulfonyl)oxy)pyrido[1,2-b]indazol-9-yl)-2-oxoethyl)tetrahydro-1H-thiophen-1-ium as orange solid. LCMS (M+H)=484.2. To a stirred solution of above crude 1-(1-cyano-2-(8-methyl-10-(((trifluoromethyl)sulfonyl)oxy)pyrido[1,2-b]indazol-9-yl)-2-oxoethyl)tetrahydro-1H-thiophen-1-ium in MeOH (10 mL) was added a solution of oxone (1.314 g, 2.138 mmol) in water (10 mL) at rt. After 6 h, the reaction mixture was diluted with ether (100 mL), aq layer separated and org layer washed with water (2×10 mL), brine (10 mL), dried (MgSO$_4$), filtered, concentrated and purified flash chromatography using 500 mL each 15, 20, 25 and 30% EtOAc/Hex to afford methyl 2-(8-methyl-10-(((trifluoromethyl)sulfonyl)oxy)pyrido[1,2-b]indazol-9-yl)-2-oxoacetate (0.165 g, 0.396 mmol, 37.1% yield) as yellow solid. LCMS (M+H)=417.2.

Intermediate 28

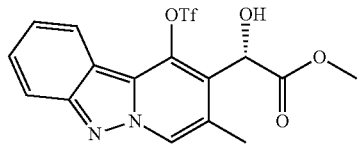 [SMILES: COC(=O)[C@@H](O)c1c(C)cn2nc3ccccc3c2c1OS(=O)(=O)C(F)(F)F]

(S)-Methyl 2-hydroxy-2-(8-methyl-10-(((trifluoromethyl)sulfonyl)oxy)pyrido[1,2-b]indazol-9-yl)acetate To a stirred solution of methyl 2-(8-methyl-10-(((trifluoromethyl)sulfonyl)oxy)pyrido[1,2-b]indazol-9-yl)-2-oxoacetate (0.165 g, 0.396 mmol) and 1M (R)-1-methyl-3,3-diphenylhexahydropyrrolo[1,2-c][1,3,2]oxazaborole/toluene (0.079 ml, 0.079 mmol) in toluene (10 mL) was added dropwise 50 wt % catecholoborane (0.106 ml, 0.495 mmol) at −30° C. Then, the reaction was slowly warm to −15° C. over 1 h and stirred for 1.5 h, diluted with EtOAc (10 mL) and sat $Na_2CO_3$ (5 mL), stirred vigarously at rt for 30 min. Aq layer separated and org layer washed with sat $Na_2CO_3$ (5 mL) and brine (5 mL), dried ($MgSO_4$), filtered and concentrated to give crude (S)-methyl 2-hydroxy-2-(8-methyl-10-(((trifluoromethyl)sulfonyl)oxy)pyrido[1,2-b]indazol-9-yl)acetate as brown which was used in the next step without purification. LCMS (M+H)=419.2.

Intermediate 29

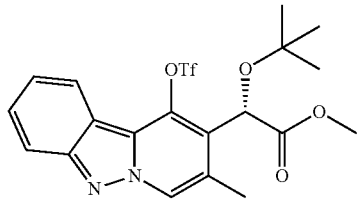 [SMILES: COC(=O)[C@@H](OC(C)(C)C)c1c(C)cn2nc3ccccc3c2c1OS(=O)(=O)C(F)(F)F]

(S)-Methyl 2-(tert-butoxy)-2-(8-methyl-10-(((trifluoromethyl)sulfonyl)oxy)pyrido[1,2-b]indazol-9-yl)acetate To a stirred solution of crude (S)-methyl 2-hydroxy-2-(8-methyl-10-(((trifluoromethyl)sulfonyl)oxy)pyrido[1,2-b]indazol-9-yl)acetate in $CH_2Cl_2$ (5 mL) and tert-butyl acetate (2.68 ml, 19.82 mmol) was added 70% perchloric acid (0.102 ml, 1.189 mmol) at rt and sealed with septa. After 3 h, the reaction mixture was diluted with $Et_2O$ (50 mL), washed with sat $Na_2CO_3$ (3×10 mL), dried ($MgSO_4$), filtered, concentrated and purified by prep-HPLC to afford (S)-methyl 2-(tert-butoxy)-2-(8-methyl-10-(((trifluoromethyl)sulfonyl)oxy)pyrido[1,2-b]indazol-9-yl)acetate (0.0162 g, 0.034 mmol, 8.62% yield over two steps) as light brown solid. LCMS (M+H)=475.3.

Intermediate 30

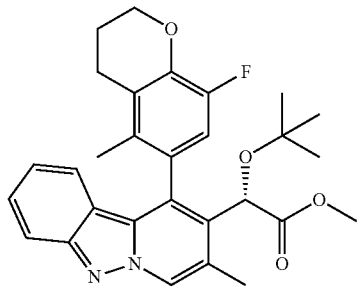 [SMILES: COC(=O)[C@@H](OC(C)(C)C)c1c(C)cn2nc3ccccc3c2c1-c1cc(F)c2c(c1C)CCCO2]

(2S)-Methyl 2-(tert-butoxy)-2-(10-(8-fluoro-5-methylchroman-6-yl)-8-methylpyrido[1,2-b]indazol-9-yl)acetate A mixture of (S)-methyl 2-(tert-butoxy)-2-(8-methyl-10-(((trifluoromethyl)sulfonyl)oxy)pyrido[1,2-b]indazol-9-yl)acetate (0.016 g, 0.034 mmol), (8-fluoro-5-methylchroman-6-yl)boronic acid (0.014 g, 0.067 mmol) and 2M $Na_2CO_3$ (0.034 ml, 0.067 mmol) in DMF (1 mL) was degassed for 10 min. Then, tetrakis(triphenylphosphine)palladium(0) (3.90 mg, 3.37 μmol) was added, degassed for 5 min and heated at 110° C. for 2 h using Biotage microwave. Then, cooled, diluted with ether (25 mL), washed with water and brine (10 mL each), dried ($MgSO_4$), filtered and concentrated to give crude (2S)-methyl 2-(tert-butoxy)-2-(10-(8-fluoro-5-methylchroman-6-yl)-8-methylpyrido[1,2-b]indazol-9-yl)acetate which was used in the subsequent step without purification. LCMS (M+H)=491.4.

Example 25

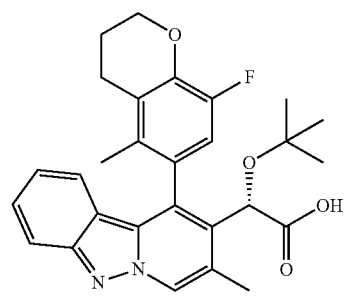 [SMILES: Cc1cn2nc3ccccc3c2c(-c2cc(F)c3c(c2C)CCCO3)c1[C@H](OC(C)(C)C)C(=O)O]

(2S)-2-(tert-Butoxy)-2-(10-(8-fluoro-5-methylchroman-6-yl)-8-methylpyrido[1,2-b]indazol-9-yl)acetic acid To the above crude (2S)-methyl 2-(tert-butoxy)-2-(10-(8-fluoro-5-methylchroman-6-yl)-8-methylpyrido[1,2-b]indazol-9-yl)acetate was added MeOH (1 mL) and 1M NaOH (0.337 ml, 0.337 mmol) and heated at reflux for 16 h. LCMS at this point showed presence of unreacted ester and desired product. So, added additional 1M NaOH (0.337 ml, 0.337 mmol) and refluxed for 24 h. Then, cooled and purified by prep-HPLC to afford (2S)-2-(tert-butoxy)-2-(10-(8-fluoro-5-methylchroman-6-yl)-8-methylpyrido[1,2-b]indazol-9-yl)acetic acid (0.0035 g, 7.27 μmol, 21.56% yield over two steps) as off-white solid and 5:1 mixture of atropisomers. $^1$H NMR (400 MHz, $CDCl_3$) δ 8.63 (s, 1H), 7.80 (d, J=8.5 Hz, 1H), 7.43-7.49 (m, 1H), 6.91-6.97 (m, 2H), 6.46 (d, J=8.3 Hz, 1H), 5.31 (s, 1H), 4.34-4.41 (m, 2H), 2.79 (t, J=6.5 Hz, 2H), 2.59 (s, 3H), 2.18-2.24 (m, 2H), 1.91 (s, 3H), 1.23 (s, 9H). LCMS (M+H)=477.4.

Intermediate 31

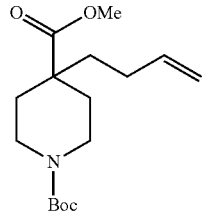 [SMILES: C=CCCC1(C(=O)OC)CCN(C(=O)OC(C)(C)C)CC1]

1-tert-Butyl 4-methyl 4-(but-3-en-1-yl)piperidine-1,4-dicarboxylate

A mixture of diisopropylamine (17.57 mL, 123 mmol) and THF (300 mL) was cooled to −78° C. and 1.6 M solution of n-BuLi (77 mL, 123 mmol) in hexane was added slowly. The mixture was stirred for 15 min, warmed to 0° C. for 20 min and cooled back to −78° C. 1-tert-Butyl 4-methyl piperidine-1,4-dicarboxylate (25 g, 103 mmol) in THF (25 mL) was added dropwise and the mixture was stirred for 40 min. Then, a mixture of HMPA (17.88 mL, 103 mmol) 4-bromobut-1-ene (27.7 g, 206 mmol) was added and the mixture was stirred for 1 h before it was warmed to room temp and stirr for 16 h. Sat. NH$_4$Cl was then added and the mixture was extracted with ether (2×500 mL), dried (Na$_2$SO$_4$), filtered and concentrated. The residue was purified by Biotage (0-20% EtOAc/hexane; 300 g column) to afford 1-tert-butyl 4-methyl 4-(but-3-en-1-yl)piperidine-1,4-dicarboxylate (22 g, 74.0 mmol, 72.0% yield) as light yellow oil. $^1$H NMR (500 MHz, CDCl$_3$) δ 5.76 (ddt, J=17.0, 10.3, 6.5 Hz, 1H), 5.06-4.92 (m, 2H), 3.94-3.85 (m, 2H), 3.73 (s, 3H), 2.95-2.80 (m, 2H), 2.13 (d, J=13.1 Hz, 2H), 2.02-1.93 (m, 2H), 1.64-1.58 (m, 2H), 1.47 (s, 9H), 1.42-1.32 (m, 2H). LCMS (M+H)=298.2.

Intermediate 32

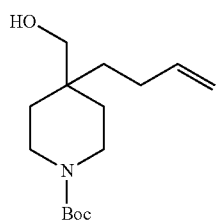 [SMILES: C=CCCC1(CO)CCN(C(=O)OC(C)(C)C)CC1]

tert-Butyl 4-(but-3-en-1-yl)-4-(hydroxymethyl)piperidine-1-carboxylate

To a solution of 1-tert-butyl 4-methyl 4-(but-3-en-1-yl) piperidine-1,4-dicarboxylate (21.2 g, 71.3 mmol) in THF (300 mL) at 0° C. was added 2M LAH/THF (35.6 mL, 71.3 mmol) and the resulting mixture was stirred at 0° C. for 1 h and then stirred at room temp for 2 h. The mixture was then recooled to 0° C. and water (2.7 mL), 1N NaOH (2.7 mL) and water (8.2 mL) were added successively and the mixture was stirred for 5 min. The solids were filtered off and the cake was washed with ethyl acetate. The filterate was washed with water (2×50 mL), brine (100 mL), dried (Na$_2$SO$_4$), filtered and concentrated under reduced pressure to give tert-butyl 4-(but-3-en-1-yl)-4-(hydroxymethyl)piperidine-1-carboxylate (16.5 g, 61.3 mmol, 86% yield) as yellow oil. $^1$H NMR (500 MHz, CDCl$_3$) δ 5.90-5.78 (m, 1H), 5.13-5.01 (m, 1H), 5.01-4.86 (m, 1H), 3.57-3.42 (m, 4H), 3.39-3.28 (m, 2H), 2.46-2.33 (m, 1H), 2.06-1.99 (m, 2H), 1.54-1.38 (m, 14H).

Intermediate 33

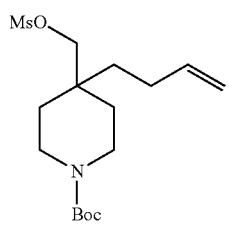 [SMILES: C=CCCC1(COS(C)(=O)=O)CCN(C(=O)OC(C)(C)C)CC1]

tert-Butyl 4-(but-3-en-1-yl)-4-(((methylsulfonyl)oxy)methyl)piperidine-1-carboxylate Ms-Cl (5.59 mL, 71.7 mmol) was added dropwise at 0° C. to a stirred solution of tert-butyl 4-(but-3-en-1-yl)-4-(hydroxymethyl)piperidine-1-carboxylate (16.1 g, 59.8 mmol) TEA (16.66 mL, 120 mmol) and DMAP (0.365 g, 2.99 mmol) in CH$_2$Cl$_2$ (300 mL) and the mixture was stirred at room temp for 2 h. Water was then added and the mixture was extracted with methylene chloride (100 mL), dried (Na$_2$SO$_4$), filtered and concentrated. The residue was purified by Biotage (0-40% Hex/EtOAc) to afford tert-butyl 4-(but-3-en-1-yl)-4-(((methylsulfonyl)oxy)methyl)piperidine-1-carboxylate (18 g, 51.8 mmol, 87% yield) as colorless oil. $^1$H NMR (500 MHz, CDCl$_3$) δ 5.88-5.75 (m, 1H), 5.11-4.90 (m, 2H), 4.09 (s, 2H), 3.58-3.44 (m, 2H), 3.40-3.32 (m, 2H), 3.05 (s, 3H), 2.07-2.02 (m, 2H), 1.59-1.54 (m, 2H), 1.53-1.49 (m, 4H), 1.48 (s, 9H).

Intermediate 34

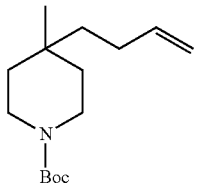 [SMILES: C=CCCC1(C)CCN(C(=O)OC(C)(C)C)CC1]

tert-Butyl 4-(but-3-en-1-yl)-4-methylpiperidine-1-carboxylate

To a solution of tert-butyl 4-(but-3-en-1-yl)-4-(((methylsulfonyl)oxy)methyl)piperidine-1-carboxylate (17 g, 48.9 mmol) in THF (250 mL) was added 1M solution of Superhydride (98 mL, 98 mmol) in THF and the resulting mixture was refluxed for 3 h. After cooling to room temp water was added and the mixture was extracted with ether (2×200 mL), washed with brine (100 mL), dried (Na$_2$SO$_4$), filtered and concentrated. The residue was purified by Biotage (0-20% EtOAc/hexane) to afford tert-butyl 4-(but-3-en-1-yl)-4-methylpiperidine-1-carboxylate (3.5 g, 13.81 mmol, 28.2% yield). $^1$H NMR (500 MHz, CDCl$_3$) δ 5.88-5.80 (m, 1H), 5.03 (dq, J=17.1, 1.7 Hz, 1H), 4.96 (ddt, J=10.2, 2.1, 1.1 Hz, 1H), 3.62-3.49 (m, 2H), 3.23 (ddd, J=13.4, 9.3, 3.8 Hz, 2H), 2.09-1.97 (m, 2H), 1.48 (s, 9H), 1.43-1.22 (m, 6H), 0.96 (s, 3H). LCMS (M+H)=254.2. 8 g of starting material was also recovered.

Intermediate 35

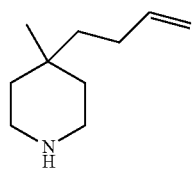

4-(But-3-en-1-yl)-4-methylpiperidine•HCl

A mixture of tert-butyl 4-(but-3-en-1-yl)-4-methylpiperidine-1-carboxylate (3.5 g, 13.81 mmol) and 4M HCl/dioxane (17.27 ml, 69.1 mmol) was stirred at room temp for 3 h. Mixture was then concentrated and dried under high vac to afford 4-(but-3-en-1-yl)-4-methylpiperidine•HCl (2.6 g, 13.70 mmol, 99% yield) as off-white solid. $^1$H NMR (500 MHz, DMSO-d$_6$) δ 5.83 (ddt, J=17.0, 10.3, 6.6 Hz, 1H), 5.05 (dq, J=17.1, 1.7 Hz, 1H), 5.00-4.80 (m, 1H), 3.11-2.90 (m, 5H), 2.05-1.90 (m, 2H), 1.56-1.42 (m, 5H), 1.38-1.26 (m, 2H), 0.95 (s, 3H). LCMS (M+H)=154.1.

Intermediate 36

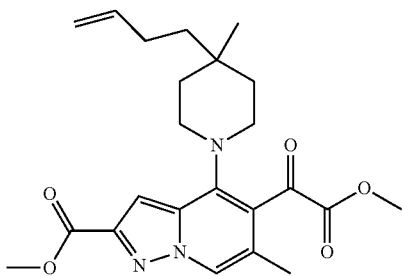

Methyl 4-(4-(but-3-en-1-yl)-4-methylpiperidin-1-yl)-5-(2-methoxy-2-oxoacetyl)-6-methylpyrazolo[1,5-a]pyridine-2-carboxylate To a stirred solution of methyl 5-(2-methoxy-2-oxoacetyl)-6-methyl-4-(((trifluoromethyl)sulfonyl)oxy)pyrazolo[1,5-a]pyridine-2-carboxylate (1.5 g, 2.83 mmol) and DIEA (1.482 mL, 8.48 mmol) in NMP (5 mL) was added 4-(but-3-en-1-yl)-4-methylpiperidine, HCl (0.805 g, 4.24 mmol) at rt. After 2 h, LCMS showed completion of reaction and major product as phenol and desired product as minor. The reaction mixture was diluted with ether (100 mL), washed with water (4×25 mL), brine (25 mL), dried (Na2SO4), filtered, concentrated and purified by Biotage (0-30% EtOAc/Hex) to afford methyl 4-(4-(but-3-en-1-yl)-4-methylpiperidin-1-yl)-5-(2-methoxy-2-oxoacetyl)-6-methylpyrazolo[1,5-a]pyridine-2-carboxylate (180 mg, 0.421 mmol, 14.89% yield) as yellow solid. $^1$H NMR (500 MHz, CDCl$_3$) δ 8.27-8.23 (m, 1H), 7.32 (d, J=0.8 Hz, 1H), 5.93-5.81 (m, 1H), 5.11-5.05 (m, 1H), 5.00 (dd, J=10.2, 1.8 Hz, 1H), 4.05 (s, 3H), 3.94 (s, 3H), 3.31-3.20 (m, 2H), 3.12-3.05 (m, 2H), 2.32 (d, J=1.1 Hz, 3H), 2.13-2.05 (m, 2H), 1.58-1.52 (m, 2H), 1.50-1.39 (m, 4H), 1.06 (s, 3H). LCMS (M+H)=428.4.

Intermediate 37

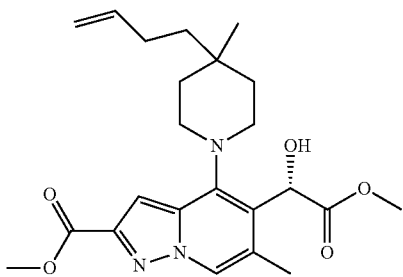

(S)-Methyl 4-(4-(but-3-en-1-yl)-4-methylpiperidin-1-yl)-5-(1-hydroxy-2-methoxy-2-oxoethyl)-6-methylpyrazolo[1,5-a]pyridine-2-carboxylate To a stirred yellow solution of methyl 4-(4-(but-3-en-1-yl)-4-methylpiperidin-1-yl)-5-(2-methoxy-2-oxoacetyl)-6-methylpyrazolo[1,5-a]pyridine-2-carboxylate (180 mg, 0.421 mmol) in anhydrous toluene (5 mL) was added 1M (R)-1-methyl-3,3-diphenylhexahydropyrrolo[1,2-c][1,3,2]oxazaborole/toluene (0.168 mL, 0.168 mmol). The mixture was cooled to −35° C. and a solution of 50% catechoborane/toluene (0.144 mL, 0.589 mmol) was added over 5 min. After 30 min, the reaction mixture was slowly warmed to −15° C. and stirred for additional 3 h. At this point LCMS indicates approx 40% conversion. 0.1 mL more of 50% catechoborane was then added and the mixture was let it sit in the freezer for 16 h. At this point LCMS indicates approx 60% conversion. Another 0.1 mL of 50% catechoborane was added and the mixture was then again let it sit in a freezer for 2 days. Mixture was then diluted with EtOAc (50 mL) and sat. Na$_2$CO$_3$ (25 mL). The mixture was stirred vigorously for 30 min, and the organic phase washed with sat Na$_2$CO$_3$ (2×10 mL), dried (Na$_2$SO$_4$), filtered, concentrated and the residue was purified by silica gel chromatography (5-100% EtOAc/hexane) to afford desired (S)-methyl 4-(4-(but-3-en-1-yl)-4-methylpiperidin-1-yl)-5-(1-hydroxy-2-methoxy-2-oxoethyl)-6-methylpyrazolo[1,5-a]pyridine-2-carboxylate (70 mg, 0.163 mmol, 38.7% yield) as off-white solid. $^1$H NMR (500 MHz, CDCl$_3$) δ 8.27 (s, 1H), 7.21 (s, 0.75H), 7.18 (s, 0.25H), 6.62 (d, J=8.4 Hz, 1H), 6.01-5.83 (m, 1H), 5.53-5.47 (m, 1H), 5.19-5.02 (m, 1H), 4.99 (d, J=10.2 Hz, 1H), 4.03 (s, 3H), 3.77 (s, 3H), 3.61-3.39 (m, 2H), 2.95-2.80 (m, 1H), 2.76-2.58 (m, 1H), 2.43 (s, 3H), 2.17-2.08 (m, 2H), 1.84-1.65 (m, 3H), 1.56-1.39 (m, 3H), 1.16 (s, 2H), 1.05 (s, 1H). LCMS (M+H)=430.4.

Intermediate 38

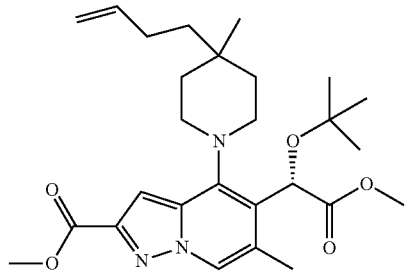

(S)-Methyl 4-(4-(but-3-en-1-yl)-4-methylpiperidin-1-yl)-5-(1-(tert-butoxy)-2-methoxy-2-oxoethyl)-6-methylpyrazolo[1,5-a]pyridine-2-carboxylate To a stirred solution of (S)-methyl 4-(4-(but-3-en-1-yl)-4-methylpiperidin-1-yl)-5-(1-hydroxy-2-methoxy-2-oxoethyl)-6-methylpyrazolo[1,5-a]pyridine-2-carboxylate (65 mg, 0.151 mmol) in fluorobenzene (2 mL) was added trifluorosulfonamide (2.256 mg, 0.015 mmol) in CH$_2$Cl$_2$ (0.2 mL) and the mixture was heated at 40° C. tert-Butyl 2,2,2-trichloroacetimidate (331 mg, 1.513 mmol) in fluorobenzene (0.5 mL) was then added and the mixture was heated for heated at 40° C. for 4 h. At this point LCMS indicates approx 60% conversion so another 5 equiv of tert-butyl 2,2,2-trichloroacetimidate was added and the mixture was heated for 16 h. Then cooled to room temp, water was added and the mixture was extracted with ether (25 mL), dried (Na$_2$SO$_4$), filtered and concentrated. The residue was purified by Biotage (0-40% EtOAc/hexane) to afford (S)-methyl 4-(4-(but-3-en-1-yl)-4-methylpiperidin-1-yl)-5-(1-(tert-butoxy)-2-methoxy-2-oxoethyl)-6-methylpyrazolo[1,5-a]pyridine-2-carboxylate (45 mg, 0.093 mmol, 61.2% yield) as viscous oil. $^1$H NMR (500 MHz, CDCl$_3$) δ 8.18 (s, 1H), 7.29 (s, 0.7H), 7.24 (s, 0.3H), 6.43 (s, 0.7H), 6.40 (s, 0.3H), 6.01-5.83 (m, 1H), 5.17-4.93 (m, 2H), 4.03 (s, 3H), 3.72 (s, 3H), 3.70-3.63 (m, 1H), 3.38-3.27 (m, 1H), 3.05-2.94 (m, 1H), 2.88-2.77 (m, 1H), 2.39-2.34 (m, 3H), 2.20-2.08 (m, 2H), 1.76-1.62 (m, 3H), 1.57-1.38 (m, 3H), 1.26 (s, 9H), 1.16 (s, 2H), 1.04 (s, 1H). LCMS (M+H)=486.4.

Intermediate 39

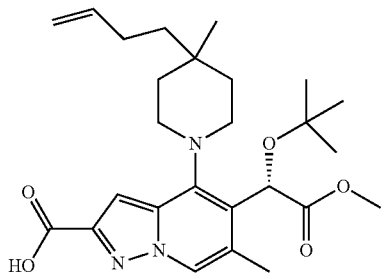 [SMILES: C=CCCC1(C)CCN(c2c([C@H](OC(C)(C)C)C(=O)OC)c(C)cn3nc(C(=O)O)cc23)CC1]

(S)-4-(4-(But-3-en-1-yl)-4-methylpiperidin-1-yl)-5-(1-(tert-butoxy)-2-methoxy-2-oxoethyl)-6-methyl-pyrazolo[1,5-a]pyridine-2-carboxylic acid To a solution of (S)-methyl 4-(4-(but-3-en-1-yl)-4-methylpiperidin-1-yl)-5-(1-(tert-butoxy)-2-methoxy-2-oxoethyl)-6-methylpyrazolo[1,5-a]pyridine-2-carboxylate (45 mg, 0.093 mmol) in MeOH (1 mL) and THF (1 mL) was added 1N NaOH (0.102 mL, 0.102 mmol) and the resulting mixture was stirred at room temp for 5 h. Water was then added and the mixture was extracted with ether (10 mL). Ethereal layer was then discarded and aqueous layer was acidified with 1N HCl and extracted with ethyl acetate (25 mL), washed with brine (10 mL), dried (Na2SO4), filtered and concentrated to afford (S)-4-(4-(but-3-en-1-yl)-4-methylpiperidin-1-yl)-5-(1-(tert-butoxy)-2-methoxy-2-oxoethyl)-6-methylpyrazolo[1,5-a]pyridine-2-carboxylic acid (40 mg, 0.085 mmol, 92% yield) as thick paste, which was used in the next step without further purification. $^1$H NMR (500 MHz, CDCl$_3$) δ 8.31 (s., 1H), 7.36 (s, 0.7H), 7.32 (s, 0.3H), 6.42 (s, 0.7H), 6.39 (s, 0.3H), 6.03-5.85 (m, 1H), 5.18-4.94 (m, 2H), 3.73 (s, 3H), 3.35 (br. s, 1H), 3.01 (br. s., 1H), 2.85 (br. s., 1H), 2.41 (s, 3H), 2.22-2.10 (m, 2H), 1.79-1.60 (m, 4H), 1.60-1.48 (m, 2H), 1.48-1.42 (m, 2H), 1.27 (s, 9H), 1.17 (s, 2H), 1.05 (s, 1H). LCMS (M+H)= 472.4.

Intermediate 40

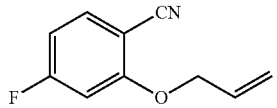

2-(Allyloxy)-4-fluorobenzonitrile

To a stirred suspension of NaH (60%, 7.6 g, 190 mmol) in toluene (300 mL) at room temp was added dropwise allyl alcohol (12.95 mL, 190 mmmol). After 30 min, 2,4-difluorobenzonitrile (27.82 g, 190 mmol) was added at once and the resulting mixture was stirred for 16 h. The mixture was then diluted with ether (300 mL), washed with water (100 mL), brine (100 mL), dried (Na$_2$SO$_4$), filtered and concentrated to give white slurry, which was purified flash chromatography on silica gel column using 9:1 Hex/EtOAc followed by 7:3 Hex/EtOAc to afford 2-(allyloxy)-4-fluorobenzonitrile (22 g, 67%) as colorless oil. $^1$H NMR (500 MHz, CDCl$_3$) δ 7.54 (dd, J=8.5, 6.4 Hz, 1H), 6.74-6.64 (m, 2H), 6.02 (ddt, J=17.3, 10.5, 5.0 Hz, 1H), 5.47 (dq, J=17.2, 1.6 Hz, 1H), 5.35 (dq, J=10.6, 1.4 Hz, 1H), 4.64 (dt, J=5.0, 1.6 Hz, 2H). LCMS (M+H)=178.14.

Intermediate 41

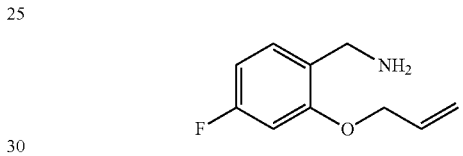

(2-(Allyloxy)-4-fluorophenyl)methanamine Hydrochloride

To an ice-cold solution of 1M LiAlH$_4$ in THF (79 mL, 79 mmol) was added drop wise over 1 h a solution of 2-(allyloxy)-4-fluorobenzonitrile (14 g, 79 mmol) in THF (80 mL). The addition flask was rinsed with THF (15 mL) and added to the reaction mixture. Then, the reaction was stirred 3 h while allowing it to warm to 0° C. The reaction mixture cooled in ice-bath and carefully quenched with water (3 mL), 15% aq. NaOH (3 ml) and water (8 mL). Then, the reaction mixture was stirred for additional 1 h at room temperature and the resulting solids were removed by filtering. The filter cake was washed with ether and combined filtrate dried (Na$_2$SO$_4$), filtered and concentrated to give product as pale yellow oil, which was purified on silica gel (5-10% MeOH/CH$_2$Cl$_2$) to afford (2-(allyloxy)-4-fluorophenyl)methanamine (2 g, 14%). $^1$H NMR (500 MHz, CDCl$_3$) δ 7.17-7.11 (m, 1H), 6.61-6.52 (m, 2H), 6.11-5.99 (m, 1H), 5.46-5.39 (m, 1H), 5.31-5.28 (m, 1H), 4.53 (dt, J=4.9, 1.5 Hz, 2H), 3.82-3.77 (m, 2H), 1.94 (br. s, 2H). This was dissolved in 1:1 an anhydrous ether/hexanes (30 mL) and treated with 2M HCl/Et$_2$O (5.52 ml, 11 mmol). The resulting yellow precipitate was filtered and dried to afford (2-(allyloxy)-4-fluorophenyl)methanamine hydrochloride (2.1 g, 95%). $^1$H NMR (500 MHz, DMSO-d$_6$) δ 7.46 (dd, J=8.4, 6.9 Hz, 1H), 6.99 (dd, J=11.3, 2.4 Hz, 1H), 6.84 (td, J=8.5, 2.4 Hz, 1H), 6.14-6.04 (m, 1H), 5.49-5.41 (m, 1H), 5.30 (dd, J=10.7, 1.5 Hz, 1H), 4.70-4.65 (m, 2H), 3.95 (d, J=4.6 Hz, 2H).

57

Intermediate 42

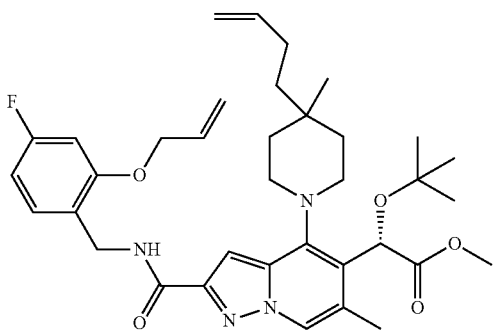 [SMILES: C=CCCC1(C)CCN(c2c([C@H](OC(C)(C)C)C(=O)OC)c(C)cn3nc(C(=O)NCc4ccc(F)cc4OCC=C)cc23)CC1]

(S)-Methyl 2-(2-((2-(allyloxy)-4-fluorobenzyl)carbamoyl)-4-(4-(but-3-en-1-yl)-4-methylpiperidin-1-yl)-6-methylpyrazolo[1,5-a]pyridin-5-yl)-2-(tert-butoxy)acetate To a solution of (S)-4-(4-(but-3-en-1-yl)-4-methylpiperidin-1-yl)-5-(1-(tert-butoxy)-2-methoxy-2-oxoethyl)-6-methylpyrazolo[1,5-a]pyridine-2-carboxylic acid (40 mg, 0.085 mmol) and (2-(allyloxy)-4-fluorophenyl)methanamine, HCl (36.9 mg, 0.170 mmol) in DMF (2 mL) was added DIEA (0.074 mL, 0.424 mmol) followed by HATU (64.5 mg, 0.170 mmol) and DMAP (1.036 mg, 8.48 µmol) and the resulting mixture was stirred at room temp for 3 h. Water was then added and the mixture was extracted with ether (2×10 mL), washed with brine (10 mL), dried (Na$_2$SO$_4$), filtered and concentrated. The residue was purified by Biotage (0-40% EtOAc/hexane) to afford (S)-methyl 2-(2-((2-(allyloxy)-4-fluorobenzyl)carbamoyl)-4-(4-(but-3-en-1-yl)-4-methylpiperidin-1-yl)-6-methylpyrazolo[1,5-a]pyridin-5-yl)-2-(tert-butoxy)acetate (34 mg, 0.054 mmol, 63.1% yield) as viscous oil. $^1$H NMR (500 MHz, CDCl$_3$) δ 8.02 (s, 1H), 7.53 (t, J=6.1 Hz, 1H), 7.37-7.32 (m, 1H), 7.26 (s, 0.7H), 7.23 (s, 0.3H), 6.67-6.60 (m, 2H), 6.44 (s, 0.7H), 6.42 (s, 0.3H), 6.16-6.02 (m, 1H), 5.98-5.83 (m, 1H), 5.52-5.45 (m, 1H), 5.39-5.34 (m, 1H), 5.14-4.96 (m, 2H), 4.67 (d, J=6.1 Hz, 2H), 4.62 (dt, J=5.1, 1.5 Hz, 2H), 3.77-3.64 (m, 4H), 3.38-3.20 (m, 1H), 3.00-2.89 (m, 1H), 2.79 (d, J=11.5 Hz, 1H), 2.36 (s, 3H), 2.18-2.03 (m, 2H), 1.73-1.59 (m, 3H), 1.54-1.36 (m, 3H), 1.25 (s, 9H), 1.13 (s, 2H), 1.03 (s, 1H). LCMS (M+H)=635.6.

Example 26

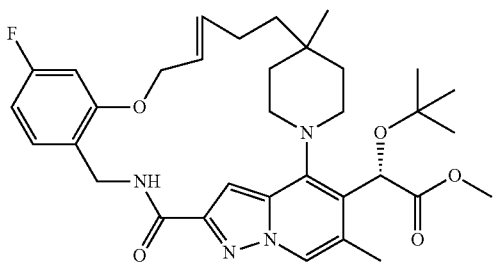 [SMILES: COC(=O)[C@@H](OC(C)(C)C)c1c(C)cn2nc3cc2c1N1CCC(C)(CC/C=C/COc2cc(F)ccc2CNC3=O)CC1]

58

(2S)-2-(tert-Butoxy)-2-[(21E)-16-fluoro-4,25-dimethyl-10-oxo-19-oxa-1,6,11,30-tetraazapentacyclo[23.2.2.1$^{6,9}$.0$^{2,7}$.0$^{13,18}$]triaconta-2,4,7,9(30),13(18),14,16,21-octaen-3-yl]acetic acid To a solution of (S)-methyl 2-(2-((2-(allyloxy)-4-fluorobenzyl)carbamoyl)-4-(4-(but-3-en-1-yl)-4-methylpiperidin-1-yl)-6-methylpyrazolo[1,5-a]pyridin-5-yl)-2-(tert-butoxy)acetate (30 mg, 0.047 mmol) in DCE (30 mL) at 70° C. was added Hoveyda-Grubbs Catalyst 2nd Generation (2.97 mg, 4.73 µmol). After, 2 h at 70° C., mixture was cooled, the solvent was removed by rotary evaporator and the residue was purified by biotage (0-30% EtOAc/hexane). Product fractions were pooled and concentrated under reduced pressure, affording desired ester, which was treated with 1N NaOH (0.236 mL, 0.236 mmol) in MeOH (1 mL) at 70° C. for 3 h. Mixture was then cooled and purified by prep HPLC to afford (2S)-tert-butoxy(16-fluoro-4,25-dimethyl-10-oxo-19-oxa-1,6,11,30-tetraazapentacyclo[23.2.2.1~6,9.0~2,7.0~13,18~]triaconta-2,4,7,9(30),13,15,17,21-octaen-3-yl)acetic acid (15 mg, 0.025 mmol, 53.5% yield). $^1$H NMR (500 MHz, DMSO-d$_6$) δ 8.65 (t, J=5.6 Hz, 1H), 8.37 (s, 1H), 7.38 (t, J=7.6 Hz, 1H), 7.01 (dd, J=11.9, 2.1 Hz, 1H), 6.93 (s, 1H), 6.72-6.62 (m, 1H), 6.26 (s, 1H), 6.09-5.93 (m, 2H), 4.81-4.68 (m, 2H), 4.34 (d, J=5.5 Hz, 2H), 3.69 (t, J=11.0 Hz, 2H), 2.87 (br. s., 1H), 2.28 (s, 3H), 2.07-1.95 (m, 2H), 1.98-1.92 (m, 1H), 1.70-1.57 (m, 3H), 1.54-1.41 (m, 2H), 1.18 (s, 9H), 0.98 (s, 3H). LCMS (M+H)=593.5.

Intermediate 43

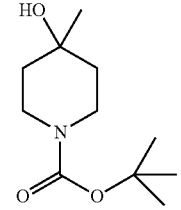

tert-Butyl 4-hydroxy-4-methylpiperidine-1-carboxylate

Under an N2 atmosphere, a 3N solution in ether of methylmagnesium bromide (1.67 mL, 5.02 mmol) was added dropwise to a cooled (−25° C.) solution of tert-butyl 4-hydroxy-4-methylpiperidine-1-carboxylate (4 g, 20.08 mmol) in ether (20 mL). The reaction mixture was allowed to warm to rt and was stirred for 2 h. It was then cooled to 0° C. and quenched by the addition of sat. aq. ammonium chloride. Another 20 mL of ether was added and the mixture was partitioned in a separatory funnel. The organic phase was set aside and the aqueous phase was extracted with another 20 mL of ether. The combined ether extracts were dried over MgSO$_4$, filtered and evaporated to obtain an oil, which was then purified by biotage, eluting with 0-50% EtOAc/hexane to obtain tert-butyl 4-hydroxy-4-methylpiperidine-1-carboxylate (4.30 g, 18.0 mmol, 90%) as a colorless oil. $^1$H NMR (400 MHz, CDCl$_3$) δ 3.84-3.65 (m, 2H), 3.34-3.18 (m, 2H), 2.59-2.39 (m, 1H), 1.61-1.53 (m, 4H), 1.50-1.45 (m, 9H), 1.32-1.27 (m, 3H).

Intermediate 44

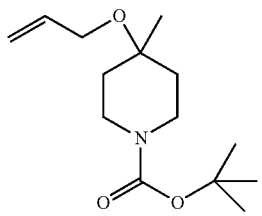 [SMILES: C=CCOC1(C)CCN(C(=O)OC(C)(C)C)CC1]

tert-Butyl 4-(allyloxy)-4-methylpiperidine-1-carboxylate

To a mixture of tert-butyl 4-hydroxy-4-methylpiperidine-1-carboxylate (4.30 g, 20.0 mmol) in DMF (50 mL) at 0° C. was added NaH (60 wt %) (1.60 g, 39.9 mmol). The mixture was then stirred at rt for 2 h. At this time allyl bromide (8.64 mL, 100 mmol) was added slowly over the course of 5 min. The reaction mixture was stirred at rt for 3 h. It was then cooled to 0° C. and quenched with sat. aq. ammonium chloride. The reaction mixture was extracted with ether. The organic phase was dried over MgSO$_4$, filtered and concentrated to obtain a colorless oil, which was then purified by biotage, eluting with 0-25% EtOAc/hexane to isolate 3.1 g (61%) of tert-butyl 4-(allyloxy)-4-methylpiperidine-1-carboxylate as a colorless oil. $^1$H NMR (500 MHz, CDCl$_3$) δ 6.02-5.90 (m, 1H), 5.32 (dd, J=17.2, 1.7 Hz, 1H), 5.16 (dd, J=10.4, 1.4 Hz, 1H), 3.94-3.88 (m, 2H), 3.73 (br. s., 2H), 3.19 (br. s., 2H), 1.78 (d, J=13.1 Hz, 2H), 1.53-1.42 (m, 11H), 1.21 (s, 3H).

Intermediate 45

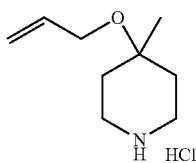

4-(Allyloxy)-4-methylpiperidine hydrogen chloride salt

A mixture of tert-butyl 4-(allyloxy)-4-methylpiperidine-1-carboxylate (3.10 g, 12.1 mmol) and 4N HCl/dioxane (15 mL, 60.0 mmol) was stirred at rt for 3 h. It was then concentrated in vacuum to obtain 2.2 g (95%) of 4-(allyloxy)-4-methylpiperidine hydrochloride as a light brown solid. $^1$H NMR (500 MHz, CD$_3$OD) δ 6.02-5.92 (m, 1H), 5.33 (dd, J=17.2, 1.7 Hz, 1H), 5.15 (dd, J=10.6, 1.7 Hz, 1H), 3.96 (dt, J=5.1, 1.6 Hz, 2H), 3.23-3.18 (m, 4H), 2.06 (dd, J=15.3, 2.5 Hz, 2H), 1.77-1.69 (m, 2H), 1.31-1.28 (s, 3H). Free amine is obtained by stirring DCM solution of amine•HCl salt with aqueous Na$_2$CO$_3$.

Intermediate 46

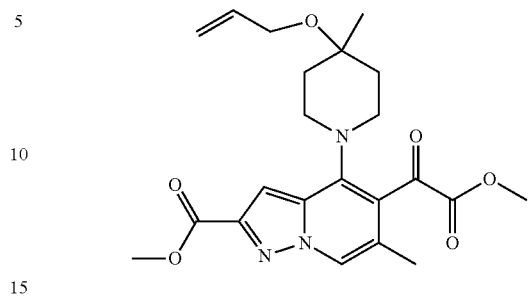

Methyl 4-(4-(allyloxy)-4-methylpiperidin-1-yl)-5-(2-methoxy-2-oxoacetyl)-6-methylpyrazolo[1,5-a]pyridine-2-carboxylate To a stirred solution of methyl 5-(2-methoxy-2-oxoacetyl)-6-methyl-4-(((trifluoromethyl)sulfonyl)oxy)pyrazolo[1,5-a]pyridine-2-carboxylate (2.5 g, 4.71 mmol) and DIEA (1.646 mL, 9.43 mmol) in CH2Cl2 (50 mL) at 0° C. was added 4-(allyloxy)-4-methylpiperidine (1.098 g, 7.07 mmol) in CH2Cl2 (10 mL) and the resulting mixture was stirred at room temp. After 1 h, LCMS showed completion of reaction. The reaction mixture was diluted with CH2Cl2 (100 mL), washed with water (4×25 mL), brine (25 mL), dried (MgSO4), filtered, concentrated and purified by biotage (0-40% EtOAc/Hex) to afford methyl 4-(4-(allyloxy)-4-methylpiperidin-1-yl)-5-(2-methoxy-2-oxoacetyl)-6-methylpyrazolo[1,5-a]pyridine-2-carboxylate (1.5 g, 3.49 mmol, 74.1% yield) as light solid. $^1$H NMR (500 MHz, CDCl$_3$) δ 8.26-8.24 (m, 1H), 7.34 (d, J=0.9 Hz, 1H), 6.03 (ddt, J=17.2, 10.4, 5.2 Hz, 1H), 5.46-5.38 (m, 1H), 5.25 (dq, J=10.4, 1.5 Hz, 1H), 4.04 (s, 3H), 3.92 (s, 3H), 3.59-3.48 (m, 2H), 2.87 (d, J=11.2 Hz, 2H), 2.33 (d, J=1.1 Hz, 3H), 1.90 (d, J=12.3 Hz, 2H), 1.68-1.60 (m, 2H), 1.28 (s, 3H). LCMS (M+H)=430.3.

Intermediate 47

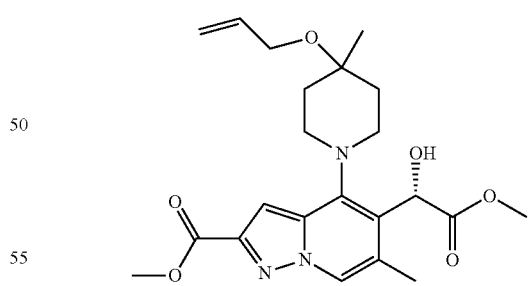

(S)-Methyl 4-(4-(allyloxy)-4-methylpiperidin-1-yl)-5-(1-hydroxy-2-methoxy-2-oxoethyl)-6-methylpyrazolo[1,5-]pyridine-2-carboxylate To a stirred yellow solution of methyl 4-(4-(allyloxy)-4-methylpiperidin-1-yl)-5-(2-methoxy-2-oxoacetyl)-6-methylpyrazolo[1,5-a]pyridine-2-carboxylate (1.4 g, 3.26 mmol) in anhydrous Toluene (50 mL) was added 1M (R)-1-methyl-3,3-diphenylhexahydropyrrolo[1,2-c][1,3,2]oxazaborole/ toluene (3.26 mL, 3.26 mmol). The mixture was cooled to −35° C. and a 50% solution of catecboborane/toluene (1.597 mL, 6.52 mmol) was added over 5 min. After 30 min, the reaction mixture was let it sit in a freezer (approx −10° C.) for 5 days. At this point LCMS indicates completion of reaction. Mixture was then warm to room temp and diluted with EtOAc (200 mL) and sat. Na₂CO₃ (100 mL). The mixture was stirred vigorously for 30 min, and the organic phase washed with sat Na₂CO₃ (2×100 mL), dried (Na2SO4), filtered, concentrated and the residue was purified by silica gel chromatography (5-100% EtOAc/hexane) to afford desired (S)-methyl 4-(4-(allyloxy)-4-methylpiperidin-1-yl)-5-(1-hydroxy-2-methoxy-2-oxoethyl)-6-methylpyrazolo[1,5-a]pyridine-2-carboxylate (700 mg, 1.622 mmol, 49.8% yield) as off-white solid. ¹H NMR (500 MHz, CDCl₃) δ 8.29-8.26 (m, 1H), 7.28-7.25 (m, 1H), 6.88 (d, J=8.7 Hz, 1H), 6.12 (ddt, J=17.1, 10.4, 5.1 Hz, 1H), 5.53-5.46 (m, 2H), 5.35-5.29 (m, 1H), 4.02 (s, 3H), 4.00 (dt, J=5.2, 1.4 Hz, 1H), 3.79-3.73 (m, 1H), 3.77 (s, 3H), 3.76-3.72 (m, 1H), 3.70-3.60 (m, 1H), 2.81 (d, J=11.2 Hz, 1H), 2.67-2.56 (m, 1H), 2.46-2.41 (m, 3H), 2.04-1.94 (m, 2H), 1.90-1.71 (m, 2H), 1.32 (s, 3H). LCMS (M+H)=432.3.

Intermediate 48

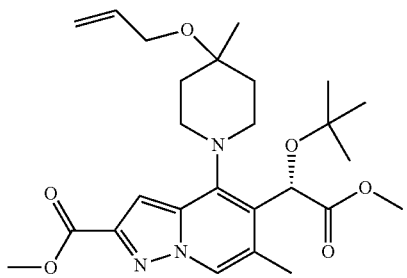

(S)-Methyl 4-(4-(allyloxy)-4-methylpiperidin-1-yl)-5-(1-(tert-butoxy)-2-methoxy-2-oxoethyl)-6-methylpyrazolo[1,5-a]pyridine-2-carboxylate To a stirred solution of (S)-methyl 4-(4-(allyloxy)-4-methylpiperidin-1-yl)-5-(1-hydroxy-2-methoxy-2-oxoethyl)-6-methylpyrazolo[1,5-a]pyridine-2-carboxylate (700 mg, 1.622 mmol) in fluorobenzene (10 mL) was added trifluoromethanesulfonimide (45.6 mg, 0.162 mmol) in CH₂Cl₂ (2 mL) and the mixture was heated at 40° C. tert-butyl 2,2,2-trichloroacetimidate (3545 mg, 16.22 mmol) in fluorobenzene (2 mL) was then added and the mixture was heated for 4 h. At this point LCMS indicates approx 50% conversion so 2 g of tert-butyl 2,2,2-trichloroacetimidate in fluorobenze (3 mL) was added and flask was sealed, heated at 40° C. for another 16 h. At this point LCMS indicates completion of reaction. Mixture was then diluted with hexanes (50 mL) and solids were filtered off and washed with hexane. the organic layer was washed with water, dried (Na2SO4), filtered and concentrated. The residue was purified via Biotage (0-40% EtOAc/hexane) to afford (S)-methyl 4-(4-(allyloxy)-4-methylpiperidin-1-yl)-5-(1-(tert-butoxy)-2-methoxy-2-oxoethyl)-6-methylpyrazolo[1,5-a]pyridine-2-carboxylate (720 mg, 1.477 mmol, 91% yield) as viscous oil. ¹H NMR (500 MHz, CDCl₃) δ 8.18 (s, 1H), 7.31 (s, 1H), 6.43 (s, 1H), 6.17-6.05 (m, 1H), 5.49 (dd, J=17.2, 1.6 Hz, 1H), 5.30 (dd, J=10.4, 1.4 Hz, 1H), 4.01 (s, 3H), 3.86 (t, J=10.8 Hz, 1H), 3.74 (s, 3H), 3.51 (t, J=10.9 Hz, 1H), 2.91 (d, J=11.3 Hz, 1H), 2.72 (d, J=10.9 Hz, 1H), 2.38 (d, J=0.9 Hz, 3H), 2.05-1.94 (m, 2H), 1.81-1.65 (m, 2H), 1.34 (s, 3H), 1.26 (s, 9H). LCMS (M+H)=488.3.

Intermediate 49

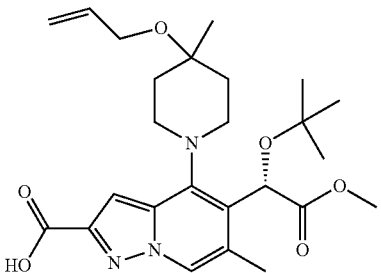 [SMILES: C=CCOC1(C)CCN(c2c([C@H](OC(C)(C)C)C(=O)OC)c(C)cn3nc(C(=O)O)cc23)CC1]

(S)-4-(4-(Allyloxy)-4-methylpiperidin-1-yl)-5-(1-(tert-butoxy)-2-methoxy-2-oxoethyl)-6-methylpyrazolo[1,5-a]pyridine-2-carboxylic acid To a solution of (S)-methyl 4-(4-(allyloxy)-4-methylpiperidin-1-yl)-5-(1-(tert-butoxy)-2-methoxy-2-oxoethyl)-6-methylpyrazolo[1,5-a]pyridine-2-carboxylate (720 mg, 1.477 mmol) in MeOH (10 mL) was added 1N NaOH (1.624 mL, 1.624 mmol) and the resulting mixture was stirred at room temp for 16 h. Water was then added and the mixture was extracted with ether (10 mL). Ethereal layer was then discarded and aqueous layer was acidified with 1N HCl and extracted with ethyl acetate (25 mL), washed with brine (10 mL), dried (Na2SO4), filtered and concentrated to afford (S)-4-(4-(allyloxy)-4-methylpiperidin-1-yl)-5-(1-(tert-butoxy)-2-methoxy-2-oxoethyl)-6-methylpyrazolo[1,5-a]pyridine-2-carboxylic acid (680 mg, 1.436 mmol, 97% yield) as thick paste, which was used in the next step without further purification. ¹H NMR (500 MHz, CDCl₃) δ 8.23 (s, 1H), 7.37 (s, 1H), 6.43 (s, 1H), 6.16-6.05 (m, 1H), 5.48 (dd, J=17.1, 1.5 Hz, 1H), 5.31 (d, J=10.4 Hz, 1H), 4.02 (d, J=5.4 Hz, 2H), 3.87 (t, J=11.2 Hz, 1H), 3.72 (s, 3H), 3.52 (t, J=11.7 Hz, 2H), 2.92 (d, J=11.7 Hz, 1H), 2.74 (d, J=10.1 Hz, 1H), 2.43-2.37 (m, 3H), 2.00 (t, J=14.5 Hz, 2H), 1.82-1.64 (m, 2H), 1.32 (s, 3H), 1.28 (s, 9H). LCMS (M+H)=475.5.

Intermediate 50

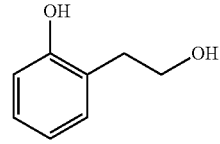

2-(2-Hydroxyethyl)phenol

To a cold (0° C.) solution of 2-(2-hydroxyphenyl)acetic acid (10 g, 65.7 mmol) in THF (150 mL) was added Et₃N (10.08 mL, 72.3 mmol) followed by ethyl chloroformate (6.31 mL, 65.7 mmol) dropwise. The mixture was stirred at 0° C. for 1 h and then solids were filtered and the filtrate was added to a cooled (0° C.) solution of NaBH₄ (3.73 g, 99 mmol) in 50% aqueous THF. The mixture was stirred at 0° C. for 1 h and then at room temp for 2 h. The solvent was removed in vacuo and the residue was digested in water (200 mL) and ether (500 mL). The ether layer was separated, washed with 2M $Na_2CO_3$, water, 1M citric acid and water, dried ($Na_2SO_4$), filtered and concentrated to afford 2-(2-hydroxyethyl)phenol (7 g, 50.7 mmol, 77% yield) as colorless oil, which was used in the next step without purification. $^1$H NMR (500 MHz, $CDCl_3$) δ 7.17 (td, J=7.7, 1.7 Hz, 1H), 7.09 (dd, J=7.5, 1.5 Hz, 1H), 6.92 (dd, J=8.0, 1.0 Hz, 1H), 6.88 (td, J=7.4, 1.3 Hz, 1H), 3.98 (dd, J=5.8, 5.0 Hz, 2H), 2.94-2.88 (m, 2H).

Intermediate 51

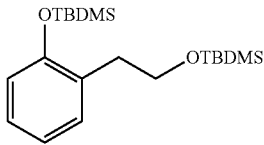 [SMILES: CC(C)(C)[Si](C)(C)OCCc1ccccc1O[Si](C)(C)C(C)(C)C]

tert-Butyl(2-(2-((tert-butyldimethylsilyl)oxy)ethyl) phenoxy)dimethylsilane

To a solution of 2-(2-hydroxyethyl)phenol (6 g, 43.4 mmol) in DMF (150 mL) at 0° C. was added imidazole (8.87 g, 130 mmol) followed by TBDMS-Cl (19.64 g, 130 mmol) and the resulting mixture was stirred at room temp for 72 h. Water (50 mL) was then added and the mixture was extracted with ether (2×200 mL). Ether layer was then washed with brine (50 mL), dried ($Na_2SO_4$), filtered and concentrated. The residue was purified by Biotage (0-10% EtOAc/hexane; 300 g column) to afford tert-butyl(2-(2-((tert-butyldimethylsilyl)oxy)ethyl)phenoxy)dimethylsilane (10.4 g, 28.4 mmol, 65.3% yield) as colorless oil. $^1$H NMR (500 MHz, $CDCl_3$) δ 7.19 (d, J=1.7 Hz, 1H), 6.89 (d, J=1.3 Hz, 1H), 6.80 (dd, J=8.0, 1.1 Hz, 1H), 3.81 (t, J=7.3 Hz, 2H), 2.87 (t, J=7.3 Hz, 2H), 1.06 (s, 9H), 0.90 (s, 9H), 0.28 (s, 6H), 0.02 (s, 6H).

Intermediate 52

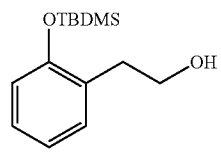 [SMILES: CC(C)(C)[Si](C)(C)Oc1ccccc1CCO]

2-(2-((tert-Butyldimethylsilyl)oxy)phenyl)ethanol

To a solution of tert-butyl(2-(2-((tert-butyldimethylsilyl) oxy)ethyl)phenoxy)dimethylsilane (8.87 g, 24.19 mmol) in ethanol (100 mL) was added PPTS (0.608 g, 2.419 mmol) and the mixture was heated at 50° C. for 1 h. The solvents were then removed and the residue was purified by flash chromatography (5-30% EtOAc/hexane) to afford 2-(2-((tert-butyldimethylsilyl)oxy)phenyl)ethanol (4.4 g, 17.43 mmol, 72.1% yield) as colorless oil. $^1$H NMR (500 MHz, $CDCl_3$) δ 7.20 (dd, J=7.4, 1.6 Hz, 1H), 7.14 (td, J=7.7, 1.7 Hz, 1H), 6.97-6.90 (m, 1H), 6.84 (dd, J=8.1, 1.0 Hz, 1H), 3.86 (q, J=6.5 Hz, 2H), 2.91 (t, J=6.5 Hz, 2H), 1.62 (t, J=5.8 Hz, 1H), 1.05 (s, 9H), 0.28 (s, 6H).

Intermediate 53

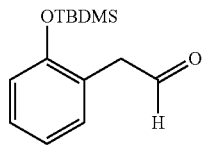 [SMILES: CC(C)(C)[Si](C)(C)Oc1ccccc1CC=O]

2-(2-((tert-Butyldimethylsilyl)oxy)phenyl)acetaldehyde

To a solution of 2-(2-((tert-butyldimethylsilyl)oxy)phenyl)ethanol (4.3 g, 17.03 mmol) in $CH_2Cl_2$ (120 mL) at 0° C. was added Dess-Martin periodinane (10.84 g, 25.6 mmol) and the mixture was stirred at 0° C. for 1 h, and then mixture was warmed to room temp and stirr for additional 1 h. Mixture was then diluted with $CH_2Cl_2$ (100 mL) and washed with sat. $NaHCO_3$ (50 mL) solution, dried ($Na_2SO_4$), filtered and concentrated. The residue was then purified by flash chromatography (5-30% EtOAc/hexane) to afford 2-(2-((tert-butyldimethylsilyl)oxy)phenyl)acetaldehyde (3.4 g, 13.58 mmol, 80% yield) as colorless oil. $^1$H NMR (500 MHz, $CDCl_3$) δ 9.72 (t, J=2.2 Hz, 1H), 7.22 (td, J=7.8, 1.8 Hz, 1H), 7.17 (dd, J=7.5, 1.5 Hz, 1H), 7.01-6.94 (m, 1H), 6.90 (dd, J=8.1, 0.9 Hz, 1H), 3.66 (d, J=2.2 Hz, 2H), 1.04 (s, 9H), 0.29 (s, 6H).

Intermediate 54

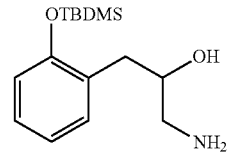

1-Amino-3-(2-((tert-butyldimethylsilypoxy)phenyl) propan-2-ol

TMS-CN (2.002 mL, 14.94 mmol) was added dropwise to a mixture of 2-(2-((tert-butyldimethylsilyl)oxy)phenyl)acetaldehyde (3.4 g, 13.58 mmol) and $ZnI_2$ (0.217 g, 0.679 mmol) in a dry round bottom flask and the mixture was stirred at room temp for 1 h. The crude cyanohydrin ether was then dissolved in ether (5 mL) and added dropwise to a solution of 2M LAH 2M/THF (7.47 mL, 14.94 mmol) in ether (20 mL) and stirred at room temp for 1 h. Water (1 mL) was then added dropwise, followed by 15% NaOH (1 mL) and then water (2 mL). Mixture was the stirred for 15 min (granular yellow precepitate were formed). Filtration, drying ($Na_2SO_4$) and concentration gave a 1-amino-3-(2-((tert-butyldimethylsilyl)oxy)phenyl)propan-2-ol (2.2 g, 7.82 mmol, 57.6% yield) as yellow oil, which was used in the next step without further purification. $^1$H NMR (500 MHz, $CDCl_3$) δ 7.19 (dd, J=7.4, 1.7 Hz, 1H), 7.13 (td, J=7.7, 1.7 Hz, 1H), 6.95-6.91 (m, 1H), 6.84 (dd, J=8.1, 1.0 Hz, 1H), 3.85-3.78 (m, 1H), 2.86-2.73 (m, 3H), 2.62 (dd, J=12.9, 7.7 Hz, 1H), 1.06 (s, 9H), 0.29 (s, 6H).

Intermediate 55

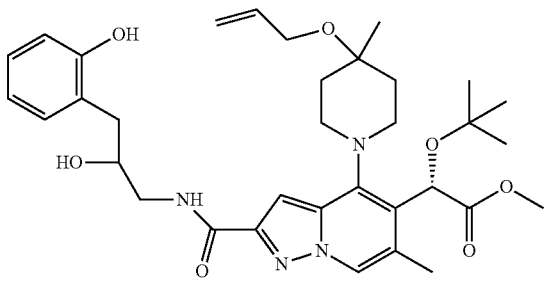 [SMILES: C=CCOC1(C)CCN(c2c([C@H](OC(C)(C)C)C(=O)OC)c(C)cn3nc(C(=O)NCC(O)Cc4ccccc4O)cc23)CC1]

(2S)-Methyl 2-(4-(4-(allyloxy)-4-methylpiperidin-1-yl)-2-((2-hydroxy-3-(2-hydroxyphenyl)propyl)carbamoyl)-6-methylpyrazolo[1,5-a]pyridin-5-yl)-2-(tert-butoxy)acetate To a solution of (S)-4-(4-(allyloxy)-4-methylpiperidin-1-yl)-5-(1-(tert-butoxy)-2-methoxy-2-oxoethyl)-6-methylpyrazolo[1,5-a]pyridine-2-carboxylic acid (330 mg, 0.697 mmol) in CH$_2$Cl$_2$ (7 mL) was added oxalyl chloride (0.383 mL, 0.767 mmol). 1 drop of DMF was then added and the mixture was stirred at room temp for 1 h. The crude acid chloride was then added to a pre-stirred solution of 1-amino-3-(2-((tert-butyldimethylsilyl)oxy)phenyl)propan-2-ol•HCl (332 mg, 1.045 mmol) and DIEA (0.609 mL, 3.48 mmol) in CH$_2$Cl$_2$ (7.00 mL) at 0° C. and the resulting solution was stirred at room temperature for 4 h. Water was then added and the mixture was extracted with dichloromethane, dried (Na$_2$SO$_4$), filtered and concentrated. The residue ws then treated with 1M TBAF (0.697 mL, 0.697 mmol) in THF (7.00 mL) at room temp for 1 h. Mixture was then concentrated and purified by flash column chromatograpgy on silica gel column using (5-100% EtOAc/Hex as eluant) to afford (2S)-methyl 2-(4-(4-(allyloxy)-4-methylpiperidin-1-yl)-2-((2-hydroxy-3-(2-hydroxyphenyl)propyl)carbamoyl)-6-methylpyrazolo[1,5-a]pyridin-5-yl)-2-(tert-butoxy)acetate (220 mg, 0.353 mmol, 50.7% yield) as white solid. $^1$H NMR (500 MHz, CDCl$_3$) δ 8.03 (s, 1H), 7.58-7.45 (m, 1H), 7.27 (s, 1H), 7.21-7.13 (m, 1H), 7.10-7.03 (m, 1H), 7.00-6.93 (m, 1H), 6.86 (t, J=7.4 Hz, 1H), 6.47-6.37 (m, 1H), 6.14-5.92 (m, 1H), 5.45 (dd, J=17.2, 1.4 Hz, 1H), 5.30 (d, J=11.5 Hz, 1H), 4.33-4.24 (m, 1H), 4.10-3.95 (m, 2H), 3.86 (t, J=11.3 Hz, 1H), 3.71 (s, 3H), 3.65-3.45 (m, 3H), 3.03-2.87 (m, 3H), 2.72 (d, J=11.2 Hz, 1H), 2.38 (s, 3H), 2.03-1.87 (m, 2H), 1.82-1.65 (m, 2H), 1.30 (s, 3H), 1.25 (s, 9H). LCMS (M+H)=623.5.

Intermediate 56

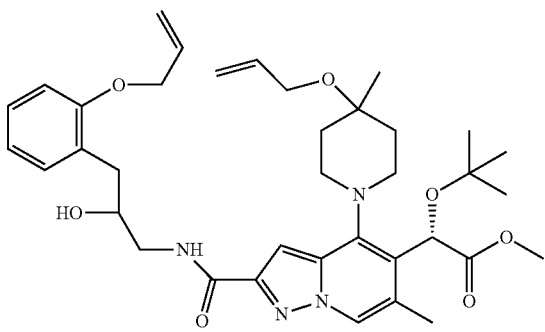 [SMILES: C=CCOc1ccccc1CC(O)CNC(=O)c1cc2c(N3CCC(C)(OCC=C)CC3)c([C@H](OC(C)(C)C)C(=O)OC)c(C)cn2n1]

(2S)-Methyl 2-(4-(4-(allyloxy)-4-methylpiperidin-1-yl)-2-((3-(2-(allyloxy)phenyl)-2-hydroxypropyl)carbamoyl)-6-methylpyrazolo[1,5-a]pyridin-5-yl)-2-(tert-butoxy)acetate To a solution of (2S)-methyl 2-(4-(4-(allyloxy)-4-methylpiperidin-1-yl)-2-((2-hydroxy-3-(2-hydroxyphenyl)propyl)carbamoyl)-6-methylpyrazolo[1,5-a]pyridin-5-yl)-2-(tert-butoxy)acetate (200 mg, 0.321 mmol) in DMF (4 mL) was added K$_2$CO$_3$ (44.4 mg, 0.321 mmol) and the mixture was heated at 70° C. for 10 min. Mixture was then cooled to room temp and added 3-bromoprop-1-ene (0.033 mL, 0.385 mmol) and the resulting mixture was stirred at room temp for 16 h. Water was then added and the mixture was extracted with ether (2×25 mL), washed with brine (10 mL), dried (Na$_2$SO$_4$), filtered and concentrated to afford (2S)-methyl 2-(4-(4-(allyloxy)-4-methylpiperidin-1-yl)-2-((3-(2-(allyloxy)phenyl)-2-hydroxypropyl)carbamoyl)-6-methylpyrazolo[1,5-a]pyridin-5-yl)-2-(tert-butoxy)acetate (180 mg, 0.272 mmol, 85% yield) as thick paste, which was used in the next step without further purification. $^1$H NMR (500 MHz, CDCl$_3$) δ 8.04 (s, 1H), 7.61-7.46 (m, 1H), 7.28 (s, 1H), 7.26-7.20 (m, 2H), 6.96 (t, J=7.3 Hz, 1H), 6.93-6.82 (m, 1H), 6.45-6.39 (m, 1H), 6.17-5.95 (m, 2H), 5.45 (dd, J=17.3, 1.3 Hz, 2H), 5.37-5.26 (m, 2H), 4.67-4.57 (m, 2H), 4.14 (dd, J=6.1, 3.0 Hz, 1H), 4.06-3.95 (m, 2H), 3.87 (t, J=10.9 Hz, 1H), 3.77 (tdd, J=10.1, 6.3, 3.4 Hz, 1H), 3.71 (s, 3H), 3.56-3.46 (m, 1H), 3.46-3.38 (m, 1H), 3.19-3.11 (m, 1H), 3.07-2.99 (m, 1H), 2.93-2.85 (m, 2H), 2.72 (d, J=10.6 Hz, 1H), 2.37 (s, 3H), 2.03-1.85 (m, 2H), 1.80-1.65 (m, 1H), 1.32 (s, 3H), 1.26 (s, 9H). LCMS (M+H)=663.6.

Intermediate 57

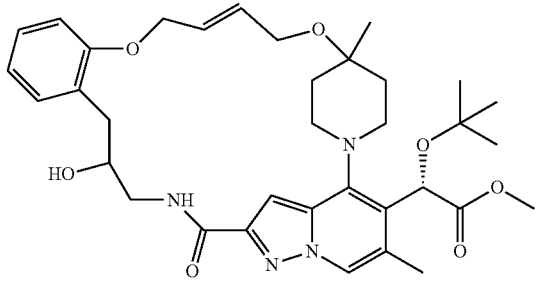 [SMILES: COC(=O)[C@@H](OC(C)(C)C)c1c(C)cn2nc3cc2c1N1CCC(C)(CC1)OC/C=C/COc1ccccc1CC(O)CNC3=O]

Methyl (2S)-2-(tert-butoxy)-2-[13-hydroxy-4,27-dimethyl-10-oxo-21,26-dioxa-1,6,11,32-tetraazapentacyclo[25.2.2.1$^{6,9}$.0$^{2,7}$.0$^{15,20}$]dotriaconta-2,4,7,9(32),15(20),16,18,23-octaen-3-yl]acetate To a solution of (2S)-methyl 2-(4-(4-(allyloxy)-4-methylpiperidin-1-yl)-2-((3-(2-(allyloxy)phenyl)-2-hydroxypropyl)carbamoyl)-6-methylpyrazolo[1,5-a]pyridin-5-yl)-2-(tert-butoxy)acetate (180 mg, 0.272 mmol) in DCE (150 mL) at 70° C. was added Hoveyda-Grubbs catalyst 2$^{nd}$ generation (13.61 mg, 0.022 mmol) and the mixture was heated at 70° C. for 3 h. At this point LCMS indicates consumption of starting material and desired product as major. Mixture was then cooled, concentrated under reduced pressure and purified via Biotage (0-80% EtOAc/hexane, 24 g column) to afford methyl (2S)-2-(tert-butoxy)-2-[13-hydroxy-4,27-dimethyl-10-oxo-21,26-dioxa-1,6,11,32-tetraazapentacyclo[25.2.2.1$^{6,9}$.0$^{2,7}$.0$^{15,20}$]dotriaconta-2,4,7,9(32),15(20),16,18,23-octaen-3-yl]acetate (100 mg, 0.158 mmol, 58.0% yield) as thick paste. $^1$H NMR (500 MHz, CDCl$_3$) δ 8.23 (d, J=2.8 Hz, 1H), 7.26 (t, J=8.0 Hz, 2H), 7.05-6.96 (m, 2H), 6.93 (s, 1H), 6.82-6.69 (m, 1H), 6.46 (d, J=17.7 Hz, 1H), 6.35-6.24 (m, 1H), 6.21-6.10 (m, 1H), 4.61 (t, J=4.9 Hz, 2H), 4.08 (d, J=4.3 Hz, 3H), 3.94-3.75 (m, 2H), 3.73-3.68 (m, 3H), 3.65-3.52 (m, 3H), 3.13-2.81 (m, 3H), 2.78-2.63 (m, 1H), 2.39 (dd, J=6.9, 0.9 Hz, 3H), 2.11-1.92 (m, 2H), 1.88-1.67 (m, 2H), 1.35 (s, 3H), 1.28 (s, 9H). LCMS (M+H)=635.6.

Intermediate 58

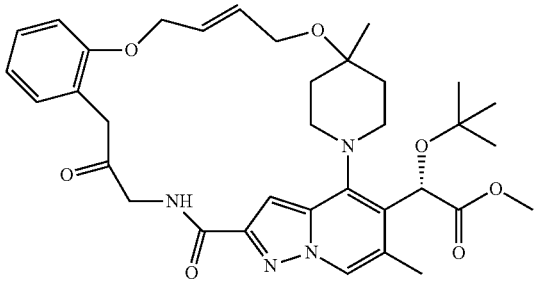 [SMILES: COC(=O)[C@@H](OC(C)(C)C)c1c(C)cn2nc3cc2c1N1CCC(C)(CC1)OC/C=C/COc1ccccc1CC(=O)CNC3=O]

Methyl (2S)-2-(tert-butoxy)-2-[4,27-dimethyl-10,13-dioxo-21,26-dioxa-1,6,11,32-tetraazapentacyclo [25.2.2.1$^{6,9}$.0$^{2,7}$.0$^{15,20}$]dotriaconta-2,4,7,9(32),15(20),16,18,23-octaen-3-yl]acetate To a solution of Reactant 1 (100 mg, 0.158 mmol) in CH$_2$Cl$_2$ (4 mL) was added powdered 4 A sieves (300 mg) and NMO (27.7 mg, 0.236 mmol). After stirring the mixture for 10 min, TPAP (5.54 mg, 0.016 mmol) was added and the mixture was stirred at room temp for 2 h. At this point LCMS indicates approx 50% conversion, so another 100 mg of NMO and 4 A sieves (300 mg) were added and the mixture was stirred at room temp for 16 h. Mixture was then filtered through a pad of silica gel and filtrate was concentrated and purified by Biotage (0-30% EtOAc/hexane; 25 g column) to afford methyl (2S)-2-(tert-butoxy)-2-[4,27-dimethyl-10,13-dioxo-21,26-dioxa-1,6,11,32-tetraazapentacyclo[25.2.2.1$^{6,9}$.0$^{2,7}$.0$^{15,20}$]dotriaconta-2,4,7,9(32),15(20),16,18,23-octaen-3-yl]acetate (20 mg, 0.032 mmol, 20.06% yield) as thick paste. NMR showed impurities. Used as in the next step without further purification. LCMS (M+H)=633.5.

Example 27

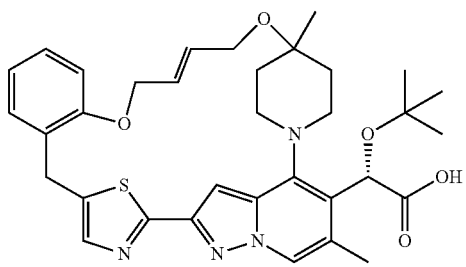 [SMILES: Cc1cn2nc3cc2c(c1[C@H](OC(C)(C)C)C(=O)O)N1CCC(C)(CC1)OC/C=C/COc1ccccc1Cc1cnc-3s1]

(2S)-2-(tert-Butoxy)-2-[(23E)-4,27-dimethyl-21,26-dioxa-32-thia-1,6,11,33-tetraazahexacyclo[25.2.2. 1$^{6,9}$.1$^{10,13}$.0$^{2,7}$.0$^{15,20}$]tritriaconta-2,4,7,9 (33),10,12,15(20),16,18,23-decaen-3-yl]acetic acid To a solution of methyl (2S)-2-(tert-butoxy)-2-[(23E)-4,27-dimethyl-10,13-dioxo-21,26-dioxa-1,6,11,32-tetraazapentacyclo[25.2.2.1$^{6,9}$.0$^{2,7}$.0$^{15,20}$]dotriaconta-2,4,7,9(32),15(20),16,18,23-octaen-3-yl]acetate (20 mg, 0.032 mmol) in Toluene (1 mL) was added Lawesson's Reagent (15.34 mg, 0.038 mmol) and the resulting mixture was heated at 70° C. for 3 h. Mixture was then cooled, concentrated and crude was treated with 1N NaOH (0.095 mL, 0.095 mmol) in MeOH (1 mL) at 70° C. for 3 h. Mixture was then cooled and purified by prep HPLC to afford (2S)-2-(tert-butoxy)-2-[(23E)-4,27-dimethyl-21,26-dioxa-32-thia-1,6,11,33-tetraazahexacyclo[25.2.2.1$^{6,9}$.1$^{10,13}$.0$^{2,7}$.0$^{15,20}$]tritriaconta-2, 4,7,9(33),10,12,15(20),16,18,23-decaen-3-yl]acetic acid (3.1 mg, 5.03 μmol, 15.90% yield). $^1$H NMR (500 MHz, DMSO-d$_6$) δ 8.39 (s, 1H), 7.80-7.71 (m, 1H), 7.34 (d, J=7.0 Hz, 1H), 7.29-7.21 (m, 1H), 7.14-7.04 (m, 1H), 6.99 (s, 1H), 6.89 (t, J=7.2 Hz, 1H), 6.28 (s, 1H), 6.23-6.18 (m, 1H), 6.18-6.05 (m, 1H), 4.90 (d, J=4.9 Hz, 2H), 4.14 (s, 2H), 4.07 (d, J=5.5 Hz, 2H), 3.87-3.73 (m, 1H), 3.66 (d, J=13.7 Hz, 2H), 3.57-3.51 (m, 1H), 2.83 (d, J=7.0 Hz, 1H), 2.31 (s, 3H), 1.86-1.69 (m, 2H), 1.67-1.54 (m, 1H), 1.29 (s, 3H), 1.20 (s, 9H). LCMS (M+H)=617.5.

Intermediate 59

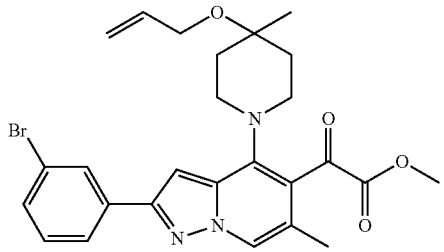 [SMILES: C=CCOC1(C)CCN(c2c(C(=O)C(=O)OC)c(C)cn3nc(-c4cccc(Br)c4)cc23)CC1]

Methyl 2-(4-(4-(allyloxy)-4-methylpiperidin-1-yl)-2-(3-bromophenyl)-6-methylpyrazolo[1,5-a]pyridin-5-yl)-2-oxoacetate A cold (0° C.) solution of methyl 2-(2-(3-bromophenyl)-6-methyl-4-(((trifluoromethyl)sulfonyl)oxy)pyrazolo[1,5-a] pyridin-5-yl)-2-oxoacetate (2.224 g, 4.27 mmol) and Hunig's Base (1.50 ml, 8.59 mmol) in CH$_2$Cl$_2$ (30 ml) was treated with a solution of 4-(allyloxy)-4-methylpiperidine (1.020 g, 6.57 mmol) in CH$_2$Cl$_2$ (10 ml), and the reaction was stirred for 4.5 hrs, then stored at 5° C. for 16 hrs. Finally, the reaction was stirred at room temperature for 4 hrs, then concentrated to dryness. The residue was purified by biotage (80 g SiO$_2$, 0% (1 CV), 0-50% (10 CV), 50% (2 CV), EtOAc in hexanes). Product fractions were pooled and concentrated under reduced pressure, affording the desired product (1.521 g, 2.74 mmol, 64.3% yield) as a yellow viscous oil. $^1$H NMR (500 MHz, CDCl$_3$) δ 8.23-8.20 (m, 1H), 8.09 (t, J=1.7 Hz, 1H), 7.88 (dt, J=7.8, 1.2 Hz, 1H), 7.51 (ddd, J=8.0, 2.0, 1.0 Hz, 1H), 7.33 (t, J=7.9 Hz, 1H), 7.01 (d, J=0.6 Hz, 1H), 6.07 (ddt, J=17.2, 10.3, 5.1 Hz, 1H), 5.51-5.42 (m, 1H), 5.33-5.27 (m, 1H), 3.98 (dt, J=5.0, 1.6 Hz, 2H), 3.92 (s, 3H), 3.59 (t, J=11.0 Hz, 2H), 2.84 (d, J=10.1 Hz, 2H), 2.32 (d, J=1.1 Hz, 3H), 1.91 (d, J=12.0 Hz, 2H), 1.67-1.58 (m, 2H), 1.30-1.26 (m, 3H). LC/MS (M+H)=526.2, 528.2.

Intermediate 60

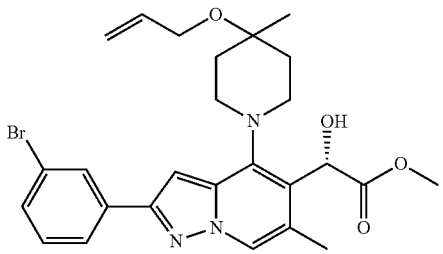 [SMILES: C=CCOC1(C)CCN(c2c([C@H](O)C(=O)OC)c(C)cn3nc(-c4cccc(Br)c4)cc23)CC1]

(S)-Methyl 2-(4-(4-(allyloxy)-4-methylpiperidin-1-yl)-2-(3-bromophenyl)-6-methylpyrazolo[1,5-a]pyridin-5-yl)-2-hydroxyacetate A solution of methyl 2-(4-(4-(allyloxy)-4-methylpiperidin-1-yl)-2-(3-bromophenyl)-6-methylpyrazolo[1,5-a]pyridin-5-yl)-2-oxoacetate (5.20 g, 9.88 mmol) and (R)-1-methyl-3,3-diphenylhexahydropyrrolo[1,2-c][1,3,2]oxazaborole (1.095 g, 3.95 mmol) in dry toluene (200 ml) was cooled (−40° C., dry ice/acetonitrile), then treated with catecholborane, 50 wt % in toluene (7.26 ml, 29.6 mmol). The reaction was stopped and placed in a −40° C. freezer for 60 hrs. The reaction was diluted with EtOAc (300 mL) and washed with sat. Na$_2$CO$_3$ (150 mL). The mixture was stirred vigorously for 30 min, and the organic phase washed with sat Na$_2$CO$_3$ (2×50 mL), brine, then dried (MgSO$_4$), filtered, and concentrated. The residue was purified by biotage (220 g SiO$_2$, 0% (3 CV), 0-50% (10 CV), 50% (2 CV), EtOAc in hexanes). Product fractions were pooled and concentrated under reduced pressure, affording the desired product (3.90 g, 7.38 mmol, 74.7% yield) as a viscous clear oil. $^1$H NMR (500 MHz, CDCl$_3$) δ 8.22 (s, 1H), 8.07 (t, J=1.7 Hz, 1H), 7.88 (dt, J=7.9, 1.2 Hz, 1H), 7.52-7.47 (m, 1H), 7.34-7.31 (m, 1H), 7.29 (d, J=8.7 Hz, 1H), 6.94 (d, J=0.5 Hz, 1H), 6.16 (ddt, J=17.2, 10.3, 5.1 Hz, 1H), 5.55 (dq, J=17.1, 1.8 Hz, 1H), 5.45 (d, J=9.0 Hz, 1H), 5.41 (dq, J=10.4, 1.5 Hz, 1H), 4.01 (dt, J=5.1, 1.5 Hz, 2H), 3.88-3.80 (m, 1H), 3.78-3.68 (m, 4H), 2.80 (d, J=11.3 Hz, 1H), 2.62 (d, J=10.9 Hz, 1H), 2.41 (d, J=0.9 Hz, 3H), 2.04-1.94 (m, 2H), 1.86 (td, J=13.1, 4.6 Hz, 1H), 1.77 (td, J=13.3, 4.6 Hz, 1H), 1.32 (s, 3H). LCMS (M+H)=530.3.

Intermediate 61

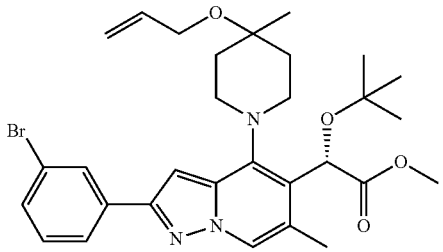 [SMILES: C=CCOC1(C)CCN(c2c([C@H](OC(C)(C)C)C(=O)OC)c(C)cn3nc(-c4cccc(Br)c4)cc23)CC1]

(S)-Methyl 2-(4-(4-(allyloxy)-4-methylpiperidin-1-yl)-2-(3-bromophenyl)-6-methylpyrazolo[1,5-a]pyridin-5-yl)-2-(tert-butoxy)acetate A 75 mL pressure vessel was charged with a solution of (S)-methyl 2-(4-(4-(allyloxy)-4-methylpiperidin-1-yl)-2-(3-bromophenyl)-6-methylpyrazolo[1,5-a]pyridin-5-yl)-2-hydroxyacetate (3.90 g, 7.38 mmol) in fluorobenzene (30 ml) and treated with trifluoromethanesulfonimide (0.207 g, 0.738 mmol) then warmed (40° C. oil bath). To the mixture was added tert-butyl 2,2,2-trichloroacetimidate (16.13 g, 73.8 mmol) and the reaction was immediately stopped and stirred for with heating overnight. The reaction was filtered to remove solids, and washed with several large volumes of hexanes. The filtrate was again filtered to remove a second crop of solids, and that filtrate was then concentrated to a light yellow oil, which was purified by biotage (220 g SiO$_2$, 0% (3 CV), 0-60% (10 CV), 60% (2 CV), EtOAc in hexanes). Product fractions were pooled and concentrated under reduced pressure, affording the desired product (2.538 g, 4.34 mmol, 58.8% yield) as a white glassy solid after drying twice from Et$_2$O. $^1$H NMR (500 MHz, CDCl$_3$) δ 8.13 (s, 1H), 8.08 (t, J=1.7 Hz, 1H), 7.88 (dt, J=7.8, 1.2 Hz, 1H), 7.50-7.46 (m, 1H), 7.33-7.28 (m, 1H), 6.98 (s, 1H), 6.46 (s, 1H), 6.15 (ddt, J=17.2, 10.3, 5.1 Hz, 1H), 5.55 (dq, J=17.1, 1.7 Hz, 1H), 5.38 (dd, J=10.4, 1.7 Hz, 1H), 4.03 (dt, J=5.0, 1.4 Hz, 2H), 3.95-3.87 (m, 1H), 3.69 (s, 3H), 3.64-3.55 (m, 1H), 2.89 (m, 1H), 2.70 (m, 1H), 2.36 (d, J=0.9 Hz, 3H), 2.04-1.93 (m, 2H), 1.77 (td, J=13.1, 4.7 Hz, 1H), 1.69 (td, J=13.0, 4.5 Hz, 1H), 1.32 (s, 3H), 1.26 (s, 9H). LCMS (M+H)=586.4.

Example 28

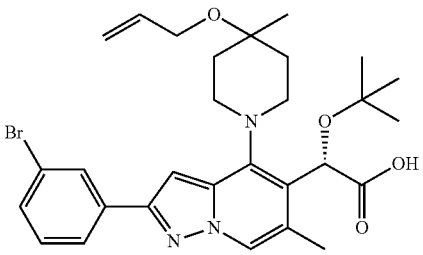 [SMILES: C=CCOC1(C)CCN(c2c([C@H](OC(C)(C)C)C(=O)O)c(C)cn3nc(-c4cccc(Br)c4)cc23)CC1]

(S)-2-(4-(4-(Allyloxy)-4-methylpiperidin-1-yl)-2-(3-bromophenyl)-6-methylpyrazolo[1,5-a]pyridin-5-yl)-2-(tert-butoxy)acetic acid A solution of (S)-methyl 2-(4-(4-(allyloxy)-4-methylpiperidin-1-yl)-2-(3-bromophenyl)-6-methylpyrazolo[1,5-a]pyridin-5-yl)-2-(tert-butoxy)acetate (0.015 g, 0.026 mmol) in MeOH (0.5 mL) was treated with 1.0 N NaOH (0.128 mL, 0.128 mmol) and heated (70° C. heating block) for 10 hrs. The reaction was cooled, then diluted with water (5 mL) and 1.0 N HCl (3 mL). The resulting solids were extracted into CH$_2$Cl$_2$, and the organic layer was washed with brine, then dried (MgSO$_4$), filtered, and concentrated under reduced pressure, to afford the desired product (0.0102 g, 0.018 mmol, 63% yield) as a glassy white solid. $^1$H NMR (500 MHz, CDCl$_3$) δ 8.21 (s, 1H), 8.07 (t, J=1.7 Hz, 1H), 7.88 (dt, J=7.9, 1.2 Hz, 1H), 7.50 (ddd, J=8.0, 1.9, 0.9 Hz, 1H), 7.32 (t, J=7.9 Hz, 1H), 6.99 (d, J=0.5 Hz, 1H), 6.16 (ddt, J=17.1, 10.4, 5.1 Hz, 1H), 5.55 (dq, J=17.2, 1.7 Hz, 1H), 5.41 (dd, J=10.4, 1.6 Hz, 1H), 4.02 (dt, J=5.1, 1.5 Hz, 2H), 4.00-3.96 (m, 1H), 3.68 (t, J=11.1 Hz, 1H), 3.28 (d, J=9.5 Hz, 1H), 2.75 (d, J=11.2 Hz, 1H), 2.42 (s, 3H), 2.08-1.96 (m, 2H), 1.81 (td, J=13.4, 4.3 Hz, 2H), 1.33 (s, 3H), 1.30 (s, 10H). LCMS (M+H)=572.4.

Intermediate 62

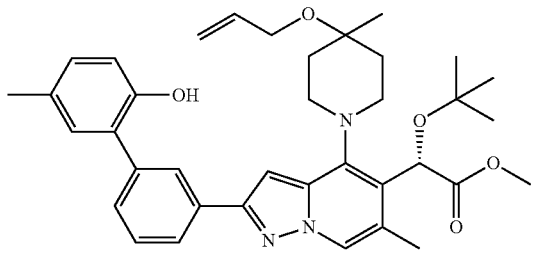

(S)-Methyl 2-(4-(4-(allyloxy)-4-methylpiperidin-1-yl)-2-(2'-hydroxy-5'-methyl-[1,1'-biphenyl]-3-yl)-6-methylpyrazolo[1,5-a]pyridin-5-yl)-2-(tert-butoxy)acetate A solution of ((S)-methyl 2-(4-(4-(allyloxy)-4-methylpiperidin-1-yl)-2-(3-bromophenyl)-6-methylpyrazolo[1,5-a]pyridin-5-yl)-2-(tert-butoxy)acetate (0.521 g, 0.891 mmol), (2-hydroxy-5-methylphenyl)boronic acid (0.271 g, 1.783 mmol) and 2.0 M aq. $Na_2CO_3$ (1.337 ml, 2.67 mmol) in DMF (8 mL) was sparged with nitrogen for 10 min, treated with $Pd(Ph_3P)_4$ (0.072 g, 0.062 mmol), then sparged for 5 min. The reaction was sealed and stirred with heating (85° C. oil bath) for 5 hrs. To this reaction was added the crude reaction mixture from another reaction (0.081 mg scale). The reaction was cooled, then diluted with water (20 mL) and extracted into $Et_2O$ (2×50 mL). The combined extracts were dried ($MgSO_4$), filtered, and concentrated under reduced pressure, and the residue was purified by biotage (40 g $SiO_2$, 0% (3 CV), 0-60% (15 CV), 60% (2 CV), EtOAc in hexanes). Product fractions were pooled and concentrated under reduced pressure, dried once from $Et_2O$, then dried under vacuum pump overnight, to afford the desired product (0.511 g, 0.835 mmol, 94% yield) as a pale yellow glassy solid. $^1$H NMR (500 MHz, $CDCl_3$) δ 8.15 (s, 1H), 8.02-8.00 (m, 1H), 7.98 (m, 1H), 7.55 (t, J=7.7 Hz, 1H), 7.47-7.44 (m, 1H), 7.14 (d, J=1.7 Hz, 1H), 7.09 (dd, J=8.3, 2.0 Hz, 1H), 7.02 (s, 1H), 6.91 (d, J=8.2 Hz, 1H), 6.46 (s, 1H), 6.08 (ddt, J=17.0, 10.4, 5.2 Hz, 1H), 5.46 (dd, J=17.2, 1.7 Hz, 1H), 5.17-5.12 (m, 2H), 4.00 (d, J=5.2 Hz, 2H), 3.69 (s, 3H), 3.63-3.55 (m, 1H), 2.90 (d, J=9.0 Hz, 1H), 2.71 (d, J=11.2 Hz, 1H), 2.37-2.33 (m, 6H), 2.02-1.93 (m, 2H), 1.77 (td, J=13.1, 4.7 Hz, 1H), 1.68 (td, J=13.0, 4.4 Hz, 1H), 1.30 (s, 3H), 1.26 (s, 9H). LCMS (M+H)=612.5.

Intermediate 63

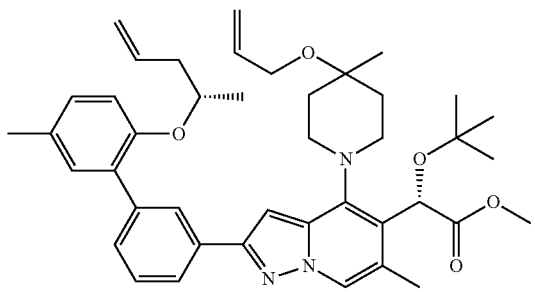

(S)-Methyl 2-(4-(4-(allyloxy)-4-methylpiperidin-1-yl)-6-methyl-2-(5'-methyl-2'-((S)-pent-4-en-2-yloxy)-[1,1'-biphenyl]-3-yl)pyrazolo[1,5-a]pyridin-5-yl)-2-(tert-butoxy)acetate A solution of (S)-methyl 2-(4-(4-(allyloxy)-4-methylpiperidin-1-yl)-2-(2'-hydroxy-5'-methyl-[1,1'-biphenyl]-3-yl)-6-methylpyrazolo[1,5-a]pyridin-5-yl)-2-(tert-butoxy)acetate (0.120 g, 0.196 mmol) in dry THF (2 mL) was treated sequentially with (R)-pent-4-en-2-ol (0.050 g, 0.581 mmol), $Ph_3P$ (0.155 g, 0.591 mmol) and DEAD (0.10 ml, 0.632 mmol), and the reaction was stirred for 20 hrs, all under nitrogen. The reaction was diluted with water (10 mL) and extracted into concentrated under reduced pressure, then the residue was purified by biotage (4 g $SiO_2$, 0% (3 CV), 0-60% (15 CV), 60% (2 CV), EtOAc in hexanes). Product fractions were pooled and concentrated under reduced pressure, affording the desired product (0.154 g, 0.180 mmol, 92% yield) as an amber viscous oil. $^1$H NMR (500 MHz, $CDCl_3$) δ 8.19-8.13 (m, 1H), 8.06 (t, J=1.5 Hz, 1H), 7.90 (d, J=7.7 Hz, 1H), 7.57 (d, J=7.9 Hz, 1H), 7.49-7.41 (m, 1H), 7.25 (d, J=1.9 Hz, 1H), 7.10 (dd, J=8.2, 1.7 Hz, 1H), 7.01 (s, 1H), 6.91 (d, J=8.4 Hz, 1H), 6.46 (s, 1H), 6.07 (ddt, J=17.0, 10.4, 5.2 Hz, 1H), 5.80-5.70 (m, 1H), 5.48 (d, J=1.7 Hz, 1H), 5.46-5.43 (m, 1H), 5.14 (dd, J=10.5, 1.5 Hz, 1H), 5.05-4.95 (m, 2H), 4.33-4.16 (m, 2H), 4.04-3.97 (m, 2H), 3.92 (t, J=11.0 Hz, 1H), 3.74-3.66 (m, 3H), 3.59 (t, J=11.6 Hz, 1H), 2.90 (d, J=9.0 Hz, 1H), 2.72 (d, J=11.0 Hz, 1H), 2.45-2.33 (m, 6H), 2.24 (dt, J=14.0, 6.9 Hz, 1H), 2.03-1.92 (m, 2H), 1.76 (td, J=13.1, 4.7 Hz, 1H), 1.68 (td, J=13.0, 4.3 Hz, 1H), 1.30 (s, 3H), 1.26 (s, 9H), 1.18 (d, J=6.1 Hz, 2H). LCMS (M+H)=681.7.

Intermediate 64

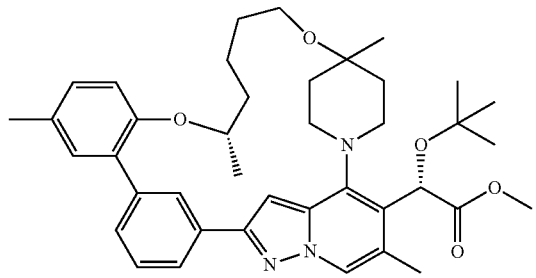

Methyl (2S)-2-(tert-butoxy)-2-[(22S)-4,17,22,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetate A solution of (S)-methyl 2-(4-(4-(allyloxy)-4-methylpiperidin-1-yl)-6-methyl-2-(5'-methyl-2'-((S)-pent-4-en-2-yloxy)-[1,1'-biphenyl]-3-yl)pyrazolo[1,5-a]pyridin-5-yl)-2-(tert-butoxy)acetate (0.135 g, 0.198 mmol) and copper (I) iodide (0.038 g, 0.198 mmol) in DCE (100 mL) was warmed (70° C. oil bath), then treated with Hoveyda-Grubbs catalyst, 2nd generation (8.68 mg, 0.014 mmol), and the reaction was stirred for 3.5 hrs, then warmed at a higher temperature (85° C.) and the reaction was stirred for 1 hr. The reaction was treated with additional Hoveyda-Grubbs cat., 2nd gen. (8.68 mg, 0.014 mmol) and stirring was continued for 2 hrs then concentrated under reduced pressure and the residue was stored at 4° C. for 16 hrs. The residue was dissolved in MeOH (2 mL), treated with 10 wt % Pd/C (0.018 g, 0.017 mmol) and hydrogen gas (balloon), and stirred for 3 hrs. The reaction was treated with additional 10 wt % Pd/C (0.018 g, 0.017 mmol), re-charged with $H_2$ (g) and stirred for 3 hrs.

Then the reaction mixture was filtered (0.45 μm syringe tip filter) and concentrated by rotary evaporator to dryness. The product was purified by prep-HPLC and product fractions were pooled, concentrated, and used immediately in the following step. LCMS (M+H)=654.45.

Example 29

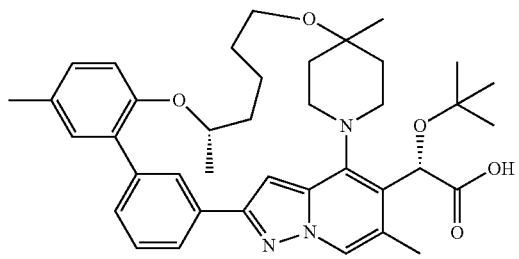 [SMILES: Cc1ccc2c(c1)-c1cccc(c1)-c1cc3c(c([C@H](OC(C)(C)C)C(=O)O)c(C)cn3n1)N1CCC(C)(CC1)OCCCC[C@H](C)O2]

(2S)-2-(tert-Butoxy)-21[(22S)-4,17,22,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9 (34),10 (33),11,13,15(20),16,18-decaen-3-yl]acetic acid A solution of methyl (2S)-2-(tert-butoxy)-2-[(22S)-4,17,22,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10 (33),11,13,15(20),16,18-decaen-3-yl]acetate (0.071 g, 0.109 mmol) in MeOH (1 mL) was treated with 1.0 M NaOH (0.543 mL, 0.543 mmol). The addition of base resulted in an insoluble gum so THF (1 mL) was added and the reaction was stirred 3.5 hrs. The reaction was cooled, then diluted with EtOAc (10 mL) and 1.0 N HCl (5 mL) and water (5 mL). The layers were separated and the organic layer was washed with brine, then dried (MgSO$_4$), filtered, and concentrated under reduced pressure. The crude material was purified via preparative LCMS. Fractions containing the desired product were combined and dried via centrifugal evaporation, affording the desired product (0.050 g, 0.078 mmol, 72.0% yield). $^1$H NMR (500 MHz, CDCl$_3$) δ 8.24 (s, 2H), 8.17-8.07 (m, 1H), 7.56-7.46 (m, 1H), 7.42-7.35 (m, 1H), 7.22-7.16 (m, 1H), 7.15-7.05 (m, 2H), 6.96-6.88 (m, 1H), 4.60-4.51 (m, 1H), 4.03-3.89 (m, 1H), 3.67 (t, J=11.6 Hz, 1H), 3.56-3.42 (m, 2H), 3.34 (br. s., 1H), 3.20 (d, J=10.1 Hz, 1H), 2.82-2.64 (m, 1H), 2.41 (s, 2H), 2.35 (s, 3H), 2.02-1.92 (m, 3H), 1.87-1.74 (m, 5H), 1.70-1.51 (m, 3H), 1.31 (s, 9H), 1.27 (s, 3H), 1.15 (d, J=6.0 Hz, 3H). LCMS (M+H)=640.6.

Intermediate 65

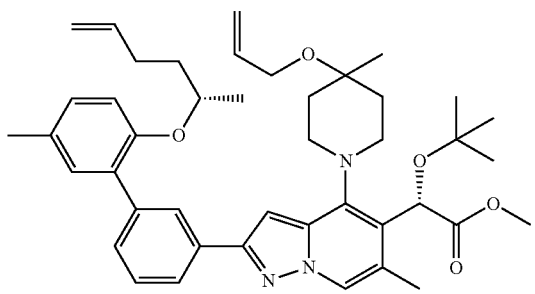

Methyl (2S)-2-(tert-butoxy)-2-[2-(3-{2-[(2S)-hex-5-en-2-yloxy]-5-methylphenyl}phenyl)-6-methyl-4-[4-methyl-4-(prop-2-en-1-yloxy)piperidin-1-yl]pyrazolo[1,5-a]pyridin-5-yl]acetate A solution of (S)-methyl 2-(4-(4-(allyloxy)-4-methylpiperidin-1-yl)-2-(2'-hydroxy-5'-methyl-[1,1'-biphenyl]-3-yl)-6-methylpyrazolo[1,5-a]pyridin-5-yl)-2-(tert-butoxy)acetate (0.125 g, 0.204 mmol) in dry THF (2.0 ml) was treated sequentially with (R)-hex-5-en-2-ol (0.063 g, 0.613 mmol), Ph$_3$P (0.161 g, 0.613 mmol) and DEAD (0.097 ml, 0.613 mmol), and the reaction was stirred for 16 hrs. The reaction was concentrated under reduced pressure, then the residue was taken up in Et$_2$O (10 mL) and washed with water (2×10 mL), then dried (MgSO$_4$), filtered, and concentrated under reduced pressure. The residue was purified by biotage (40 g SiO$_2$, 0-50% (25 CV), 50% (4 CV), EtOAc in hexanes). Product fractions were pooled and concentrated under reduced pressure, affording the desired product (0.069 g, 0.099 mmol, 48.7% yield) as a clear film. $^1$H NMR (500 MHz, CDCl$_3$) δ 8.19-8.14 (m, 1H), 8.11-8.04 (m, 1H), 7.89 (m, 1H), 7.61-7.52 (m, 1H), 7.50-7.40 (m, 1H), 7.25 (d, J=1.9 Hz, 1H), 7.10 (dd, J=8.3, 2.0 Hz, 1H), 7.02 (s, 1H), 6.90 (d, J=8.4 Hz, 1H), 6.51-6.39 (m, 1H), 6.14-5.94 (m, 1H), 5.73 (ddt, J=17.0, 10.3, 6.7 Hz, 1H), 5.51-5.31 (m, 1H), 5.22-5.07 (m, 1H), 4.97-4.83 (m, 2H), 4.35-4.19 (m, 1H), 4.09-3.97 (m, 2H), 3.93 (t, J=11.0 Hz, 1H), 3.74-3.68 (m, 3H), 3.65-3.55 (m, 1H), 2.90 (d, J=9.3 Hz, 1H), 2.72 (d, J=11.0 Hz, 1H), 2.36 (s, 6H), 2.13-2.04 (m, 2H), 2.02-1.93 (m, 2H), 1.81-1.64 (m, 3H), 1.30 (s, 3H), 1.27 (s, 9H), 1.18 (d, J=6.1 Hz, 2H). LCMS (M+H)=694.5.

Example 30

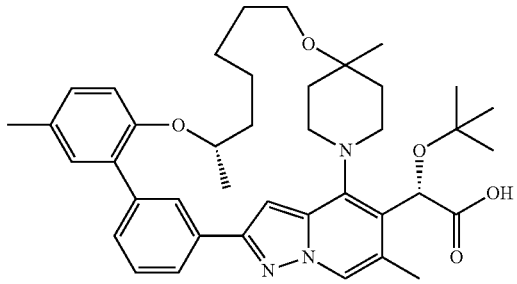 [SMILES: Cc1ccc2c(c1)-c1cccc(c1)-c1cc3c(c([C@H](OC(C)(C)C)C(=O)O)c(C)cn3n1)N1CCC(C)(CC1)OCCCCC[C@H](C)O2]

(2S)-2-(tert-Butoxy)-2-[(22S)-4,17,22,29-tetramethyl-21,28-dioxa-1,6,35-triazahexacyclo[27.2.2.1$^{6,9}$.1$^{10,14}$.0$^{2,7}$.0$^{15,20}$]pentatriaconta-2,4,7,9 (35),10 (34),11,13,15(20),16,18-decaen-3-yl]acetic acid A solution of methyl (2S)-2-(tert-butoxy)-2-[2-(3-{2-[(2S)-hex-5-en-2-yloxy]-5-methylphenyl}phenyl)-6-methyl-4-[4-methyl-4-(prop-2-en-1-yloxy)piperidin-1-yl] pyrazolo[1,5-a]pyridin-5-yl]acetate (0.045 g, 0.065 mmol) in dichloroethane (35 mL) was heated (85° C. oil bath) and then treated with Hoveyda-Grubbs catalyst 2nd generation (5 mg, 7.98 μmol), and the reaction was stirred for 3 hrs, then concentrated. The residue was dissolved in MeOH (1.0 mL) then treated with Pd/C (6.92 mg, 6.50 μmol) and H$_2$ gas (balloon). The reaction was stirred for 2 hrs and filtered (0.45 μm syringe tip filter). The filtrate was diluted with THF (1.0 mL), treated with NaOH (0.065 mL, 0.065 mmol) and the reaction was heated (75° C. oil bath) for 3 hrs. The reaction was cooled, diluted with 1.0 N HCl and extracted with CH₂Cl₂. The organic layer was dried (MgSO₄), filtered, and concentrated under reduced pressure, and the residue was separated into two isomers via preparative HPLC; (0.0176 g, 0.026 mmol, 40.6% yield). ¹H NMR (500 MHz, DMSO-d₆) δ 8.40 (s, 1H), 8.04-7.96 (m, 2H), 7.50 (t, J=8.1 Hz, 1H), 7.33 (d, J=7.3 Hz, 1H), 7.13 (d, J=4.3 Hz, 2H), 7.10-7.03 (m, 1H), 6.87 (s, 1H), 6.20 (s, 1H), 4.51 (d, J=5.2 Hz, 1H), 3.78 (t, J=10.5 Hz, 1H), 2.99 (br. s., 1H), 2.66 (d, J=10.4 Hz, 1H), 2.28 (s, 6H), 1.93-1.76 (m, 2H), 1.71-1.43 (m, 10H), 1.21-1.11 (m, 12H), 1.03 (d, J=6.1 Hz, 3H). LCMS (M+H)=654.8.

Example 31

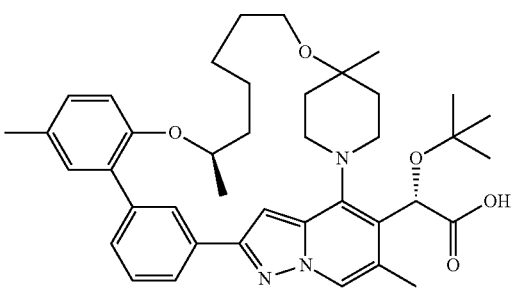 [SMILES: Cc1ccc2c(c1)-c1cccc(c1)-c1cc3c(c([C@H](OC(C)(C)C)C(=O)O)c(C)cn3n1)N1CCC(C)(CC1)OCCCCC[C@@H](C)O2]

(2S)-2-(tert-Butoxy)-2-[(22R)-4,17,22,29-tetramethyl-21,28-dioxa-1,6,35-triazahexacyclo[27.2.2. 1⁶,⁹.1¹⁰,¹⁴.0²,⁷.0¹⁵,²⁰]pentatriaconta-2,4,7,9 (35),10 (34),11,13,15(20),16,18-decaen-3-yl]acetic acid From the preceding example, an early eluting isomer (0.0053 g, 7.94 μmol, 12.22% yield) was isolated. ¹H NMR (400 MHz, DMSO-d₆) δ 8.40 (s, 1H), 8.03 (s, 1H), 7.94 (d, J=7.6 Hz, 1H), 7.52 (t, J=7.6 Hz, 1H), 7.37 (d, J=7.6 Hz, 1H), 7.26-7.10 (m, 2H), 7.10-6.99 (m, 1H), 6.91-6.79 (m, 1H), 6.19 (s, 1H), 4.56 (br. s., 1H), 3.84-3.64 (m, 1H), 3.00 (br. s., 1H), 2.72 (d, J=8.3 Hz, 1H), 2.29 (s, 7H), 2.00 (d, J=13.4 Hz, 1H), 1.86-1.40 (m, 11H), 1.35 (s, 2H), 1.20 (s, 3H), 1.19-1.12 (m, 12H). LCMS (M+H)=654.8.

Intermediate 66

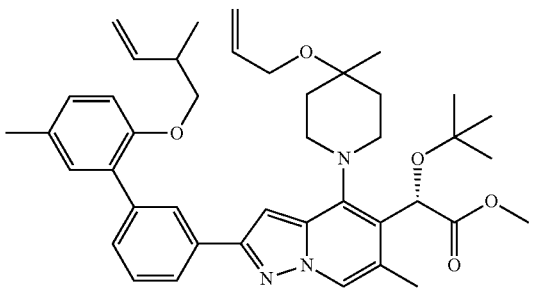

(2S)-Methyl 2-(4-(4-(allyloxy)-4-methylpiperidin-1-yl)-6-methyl-2-(5'-methyl-2'-((2-methylbut-3-en-1-yl)oxy)-[1,1'-biphenyl]-3-yl)pyrazolo[1,5-a]pyridin-5-yl)-2-(tert-butoxy)acetate A solution of (S)-methyl 2-(4-(4-(allyloxy)-4-methylpiperidin-1-yl)-2-(2'-hydroxy-5'-methyl-[1,1'-biphenyl]-3-yl)-6-methylpyrazolo[1,5-a]pyridin-5-yl)-2-(tert-butoxy)acetate (0.150 g, 0.245 mmol) in dry THF (2.452 ml) was treated sequentially with 2-methylbut-3-en-1-ol (0.063 g, 0.736 mmol), Ph₃P (0.193 g, 0.736 mmol) and DEAD (0.116 ml, 0.736 mmol), and the reaction was stirred under nitrogen for 16 hrs. The reaction was diluted with Et₂O (10 mL) and washed with water (2×10 mL), then dried (MgSO₄), filtered, and concentrated under reduced pressure. The residue was purified by biotage (40 g SiO₂, 0-50% (25 CV), 50% (4 CV), EtOAc in hexanes). Product fractions were pooled and concentrated under reduced pressure, affording the desired product (0.148 g, 0.218 mmol, 89% yield) as a clear viscous oil. ¹H NMR (500 MHz, CDCl₃) δ 8.19-8.13 (m, 1H), 8.10-8.03 (m, 1H), 7.92 (d, J=7.9 Hz, 1H), 7.60-7.52 (m, 1H), 7.50-7.41 (m, 1H), 7.25 (d, J=2.2 Hz, 1H), 7.11 (dd, J=8.3, 1.8 Hz, 1H), 7.01 (s, 1H), 6.92-6.83 (m, 1H), 6.46 (s, 1H), 6.07 (ddt, J=17.1, 10.4, 5.1 Hz, 1H), 5.79 (ddd, J=17.4, 10.4, 7.1 Hz, 1H), 5.50-5.42 (m, 1H), 5.12 (dd, J=10.4, 1.6 Hz, 1H), 5.02 (d, J=17.2 Hz, 1H), 4.96 (dt, J=10.4, 1.3 Hz, 1H), 4.09-3.96 (m, 2H), 3.96-3.88 (m, 1H), 3.88-3.82 (m, 1H), 3.79-3.72 (m, 1H), 3.72-3.67 (m, 3H), 3.64-3.55 (m, 1H), 2.94-2.87 (m, 1H), 2.75-2.68 (m, 1H), 2.58 (dt, J=13.2, 6.6 Hz, 1H), 2.38-2.34 (m, 6H), 2.03-1.93 (m, 2H), 1.77 (td, J=13.1, 4.7 Hz, 1H), 1.68 (td, J=13.0, 4.5 Hz, 1H), 1.30 (s, 2H), 1.26 (s, 9H), 1.04 (d, J=6.9 Hz, 3H). LCMS (M+H)=682.6.

Intermediate 67

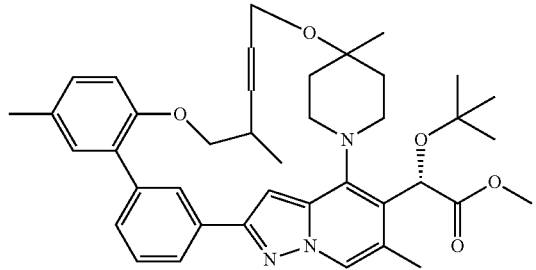

Methyl (2S)-2-(tert-butoxy)-2-{4,17,23,28-tetramethyl-21,27-dioxa-1,6,34-triazahexacyclo[26.2.2. 1⁶,⁹.1¹⁰,¹⁴.0²,⁷.0¹⁵,²⁰]tetratriaconta-2,4,7,9(34),10 (33),11,13,15(20),16,18,24-undecaen-3-yl}acetate A solution of (2S)-methyl 2-(4-(4-(allyloxy)-4-methylpiperidin-1-yl)-6-methyl-2-(5'-methyl-2'-((2-methylbut-3-en-1-yl)oxy)-[1,1'-biphenyl]-3-yl)pyrazolo[1,5-a]pyridin-5-yl)-2-(tert-butoxy)acetate (0.145 g, 0.213 mmol) in dry DCE (100 mL) was heated (85° C. oil bath), and then treated with Hoveyda-Grubbs catalyst, 2nd generation (0.020 g, 0.032 mmol). The reaction was stirred for 2 hrs, then cooled, and concentrated. The residue was purified by biotage (12 g SiO₂, 0% (3 CV), 0-60% (15 CV), 60% (2 CV), EtOAc in hexanes). Product fractions were pooled and concentrated under reduced pressure, affording the desired product (0.114 g, 0.175 mmol, 82% yield). ¹H NMR (500 MHz, CDCl3) δ 8.23-8.10 (m, 2H), 8.08-7.94 (m, 1H), 7.58-7.44 (m, 1H), 7.40-7.32 (m, 1H), 7.19 (dd, J=14.6, 2.0 Hz, 1H), 7.14-7.02 (m, 2H), 6.94 (t, J=8.1 Hz, 1H), 6.50 (d, J=7.7 Hz, 1H), 6.22-6.14 (m, 1H), 5.89-5.74 (m, 1H), 4.21-4.16 (m, 1H), 4.08-3.93 (m, 3H), 3.87-3.79 (m, 1H), 3.67 (d, J=2.4 Hz, 3H), 3.63 (d, J=14.0 Hz, 1H), 3.07-2.83 (m, 1H), 2.75-2.61

(m, 2H), 1.98 (dd, J=10.9, 2.5 Hz, 2H), 1.79-1.62 (m, 2H), 1.31 (d, J=1.6 Hz, 3H), 1.28-1.24 (m, 11H), 1.05-0.94 (m, 3H). Note: complex spectrum is a result of mixture of (R)- and (S)-methyl configuration in macrocycle linker and possible cis- and trans-olefin configuration. Piperidine proton signals are partially broadened and do not integrate to their full complement. LCMS (M+H)=652.45.

Intermediate 68

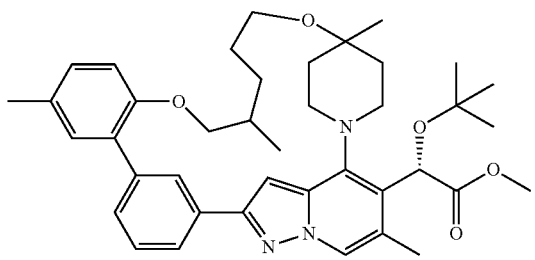

Methyl (2S)-2-(tert-butoxy)-2-{4,17,23,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9 (34),10 (33),11,13,15(20),16,18-decaen-3-yl}acetate A solution of methyl (2S)-2-(tert-butoxy)-2-{4,17,23,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18,24-undecaen-3-yl}acetate (0.114 g, 0.175 mmol) in MeOH (2.5 ml) was treated with 10 wt % Pd/C (0.019 g, 0.017 mmol), then three times evacuated and back-filled with hydrogen gas (balloon). The reaction was stirred for 6 hrs, then filtered (0.45 µm syringe tip filter) and the filtrate was concentrated under reduced pressure. The residue was purified by biotage (12 g SiO$_2$, 0% (3 CV), 0-60% (15 CV), 60% (2 CV), EtOAc in hexanes). Product fractions were pooled and concentrated under reduced pressure, affording the desired product (0.078 g, 0.119 mmol, 68.2% yield) as a viscous green oil. $^1$H NMR (500 MHz, CDCl$_3$) δ 8.27 (d, J=16.7 Hz, 1H), 8.16 (s, 1H), 8.06 (dd, J=17.7, 7.8 Hz, 1H), 7.51 (td, J=7.6, 2.8 Hz, 1H), 7.41-7.35 (m, 1H), 7.23 (dd, J=6.0, 2.0 Hz, 1H), 7.15-7.06 (m, 2H), 6.92 (d, J=8.4 Hz, 1H), 6.49 (d, J=11.2 Hz, 1H), 4.25-4.17 (m, 1H), 3.98-3.88 (m, 1H), 3.72-3.65 (m, 4H), 3.60 (t, J=11.7 Hz, 1H), 3.56-3.47 (m, 2H), 2.96-2.83 (m, 1H), 2.72-2.61 (m, 1H), 2.38-2.33 (m, 6H), 2.11 (dd, J=8.1, 4.3 Hz, 1H), 2.00-1.86 (m, 3H), 1.83-1.61 (m, 5H), 1.28-1.24 (m, 12H), 0.95-0.85 (m, 3H). Note: spectrum indicates the product is present as a pair of diasteriomers. LCMS (M+H)= 654.45.

Example 32

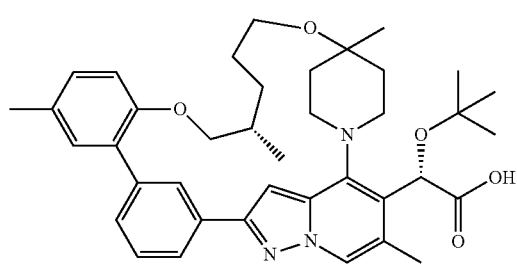 [SMILES: Cc1ccc2c(c1)-c1cccc(c1)-c1cc3c(c([C@H](OC(C)(C)C)C(=O)O)c(C)cn3n1)N1CCC(C)(CC1)OCCC[C@H](C)CO2]

(2S)-2-(tert-Butoxy)-2-[(23S)-4,17,23,28-tetramethyl-21,27-dioxa-1,6,34-triazahexacyclo[26.2.2. 1$^{6,9}$.1$^{10,14}$.0$^{2,7}$.0$^{15,20}$]tetratriaconta-2,4,7,9 (34),10 (33),11,13,15(20),16,18-decaen-3-yl]acetic acid A solution of methyl (2S)-2-(tert-butoxy)-2-{4,17,23,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13, 15(20),16,18-decaen-3-yl}acetate (0.078 g, 0.119 mmol) in MeOH (1.0 mL) was treated with 1.0 M aq. NaOH (0.596 mL, 0.596 mmol) and stirred, monitoring by LCMS until reaction was complete. The crude reaction mixture purified by preparative LCMS, first using a TFA containing mobile phase to resolve diasteriomers, then final purification of each product using ammonium acetate conditions. Resolved product fractions were dried via centrifugal evaporation, to afford the desired resolved products. The early eluting diasteriomer (0.0132 g, 0.021 mmol, 17.3% yield) was isolated as a co-product. $^1$H NMR (400 MHz, CDCl$_3$) δ 8.22 (d, J=13.9 Hz, 2H), 8.04 (d, J=7.8 Hz, 1H), 7.52 (t, J=7.7 Hz, 1H), 7.40 (d, J=7.6 Hz, 1H), 7.20 (d, J=2.2 Hz, 1H), 7.12 (dd, J=8.2, 2.1 Hz, 1H), 7.06 (s, 1H), 6.92 (d, J=8.3 Hz, 1H), 4.01 (t, J=10.8 Hz, 1H), 3.95-3.87 (m, 1H), 3.81 (dd, J=9.0, 3.4 Hz, 1H), 3.67 (t, J=10.8 Hz, 1H), 3.51 (br. s., 2H), 3.29 (d, J=10.0 Hz, 1H), 2.79-2.68 (m, 1H), 2.42 (s, 3H), 2.35 (s, 3H), 1.97 (d, J=13.4 Hz, 3H), 1.89-1.73 (m, 7H), 1.30 (s, 9H), 1.28 (s, 3H), 0.91 (d, J=7.1 Hz, 3H). LCMS (M+H)= 640.5.

Example 33

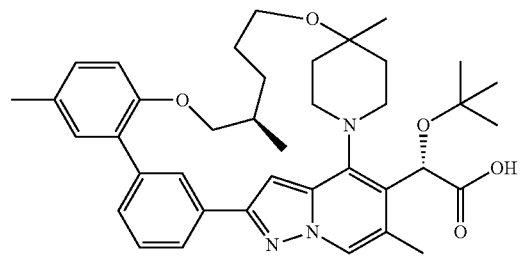 [SMILES: Cc1ccc2c(c1)-c1cccc(c1)-c1cc3c(c([C@H](OC(C)(C)C)C(=O)O)c(C)cn3n1)N1CCC(C)(CC1)OCCC[C@@H](C)CO2]

(2S)-2-(tert-Butoxy)-2-[(23R)-4,17,23,28-tetramethyl-21,27-dioxa-1,6,34-triazahexacyclo[26.2.2. 1$^{6,9}$.1$^{10,14}$.0$^{2,7}$.0$^{15,20}$]tetratriaconta-2,4,7,9 (34),10 (33),11,13,15(20),16,18-decaen-3-yl]acetic acid This later eluting diasteriomer (0.0128 g, 0.020 mmol, 16.8% yield) was isolated as a co-product from the preceding example. $^1$H NMR (400 MHz, CDCl$_3$) δ 8.25 (d, J=6.4 Hz, 2H), 8.08 (d, J=7.8 Hz, 1H), 7.51 (t, J=7.7 Hz, 1H), 7.39 (d, J=7.8 Hz, 1H), 7.22 (d, J=2.0 Hz, 1H), 7.16-7.08 (m, 2H), 6.91 (d, J=8.3 Hz, 1H), 4.22 (d, J=7.6 Hz, 1H), 4.02 (t, J=11.5 Hz, 1H), 3.67 (dd, J=9.3, 5.4 Hz, 2H), 3.59-3.43 (m, 2H), 3.33 (br. s., 1H), 2.78-2.68 (m, 1H), 2.42 (s, 3H), 2.35 (s, 3H), 1.99 (d, J=13.2 Hz, 3H), 1.94-1.74 (m, 7H), 1.30 (s, 9H), 1.28 (s, 4H), 0.86 (d, J=6.8 Hz, 3H). LCMS (M+H)= 640.5.

Intermediate 69

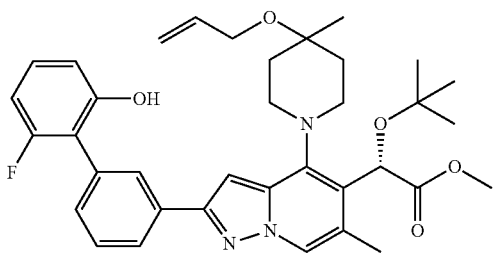 [SMILES: C=CCOC1(C)CCN(c2c([C@H](OC(C)(C)C)C(=O)OC)c(C)cn3nc(-c4cccc(-c5c(O)cccc5F)c4)cc23)CC1]

(S)-Methyl 2-(4-(4-(allyloxy)-4-methylpiperidin-1-yl)-2-(2'-fluoro-6'-hydroxy-[1,1'-biphenyl]-3-yl)-6-methylpyrazolo[1,5-a]pyridin-5-yl)-2-(tert-butoxy)acetate A solution of ((S)-methyl 2-(4-(4-(allyloxy)-4-methylpiperidin-1-yl)-2-(3-bromophenyl)-6-methylpyrazolo[1,5-a]pyridin-5-yl)-2-(tert-butoxy)acetate (0.102 g, 0.174 mmol), (2-fluoro-6-hydroxyphenyl)boronic acid (0.054 g, 0.349 mmol) and 2.0 M aq. $Na_2CO_3$ (0.262 ml, 0.523 mmol) in DMF (1.745 ml) was sparged with nitrogen for 10 min, treated with $Pd(Ph_3P)_4$ (0.014 g, 0.012 mmol), then sparged for 5 min. The reaction was stirred with heating (85° C. oil bath) for 2 hrs. The reaction was diluted with 1.0 N HCl (5 mL) and water (5 mL) and extracted into $Et_2O$ (2×10 mL). The combined extracts were dried ($MgSO_4$), filtered, and concentrated under reduced pressure and the residue was purified by biotage (12 g $SiO_2$, 0% (3 CV), 0-60% (15 CV), 60% (2 CV), EtOAc in hexanes). Product fractions were pooled and concentrated under reduced pressure, affording the desired product (0.082 g, 0.133 mmol, 76% yield) as a pale yellow oil. LCMS (M+H)=617.6.

Intermediate 70

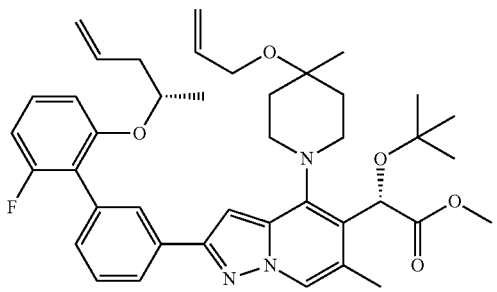 [SMILES: C=CCOC1(C)CCN(c2c([C@H](OC(C)(C)C)C(=O)OC)c(C)cn3nc(-c4cccc(-c5c(F)cccc5O[C@@H](C)CC=C)c4)cc23)CC1]

Methyl (2S)-2-(tert-butoxy)-2-[2-(3-{2-fluoro-6-[(2S)-pent-4-en-2-yloxy]phenyl}phenyl)-6-methyl-4-[4-methyl-4-(prop-2-en-1-yloxy)piperidin-1-yl]pyrazolo[1,5-a]pyridin-5-yl]acetate A solution of (S)-methyl 2-(4-(4-(allyloxy)-4-methylpiperidin-1-yl)-2-(2'-fluoro-6'-hydroxy-[1,1'-biphenyl]-3-yl)-6-methylpyrazolo[1,5-a]pyridin-5-yl)-2-(tert-butoxy)acetate (0.070 g, 0.114 mmol) in THF (1.2 mL) was treated sequentially with (R)-pent-4-en-2-ol (0.049 g, 0.568 mmol), $Ph_3P$ (0.149 g, 0.568 mmol) then DEAD (0.090 mL, 0.568 mmol). The reaction was stirred under $N_2$ atm. for 3 hrs, then the reaction was diluted with $Et_2O$ (10 mL), washed with water (10 mL) then concentrated and the residue was purified by biotage (24 g $SiO_2$, 0-40% (20 CV), 40% (2 CV), EtOAc in hexanes). Product fractions were pooled and concentrated under reduced pressure, affording the desired product (0.035 g, 0.051 mmol, 45% yield) as a pale yellow oil. LCMS (M+H)=684.45.

Example 34

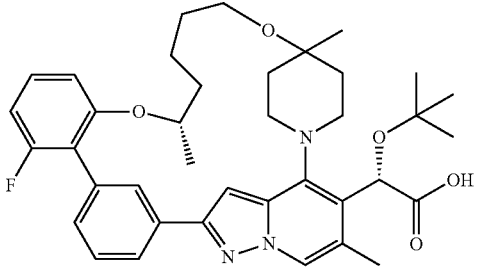 [SMILES: Cc1cn2nc3cc2c(c1[C@H](OC(C)(C)C)C(=O)O)N1CCC(C)(CC1)OCCCC[C@H](C)Oc1cccc(F)c1-c1cccc-3c1]

(2S)-2-(tert-Butoxy)-2-[(22S)-16-fluoro-4,22,28-trimethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetic acid A solution of (S)-methyl 2-(4-(4-(allyloxy)-4-methylpiperidin-1-yl)-2-(2'-fluoro-6'-((S)-pent-4-en-2-yloxy)-[1,1'-biphenyl]-3-yl)-6-methylpyrazolo[1,5-a]pyridin-5-yl)-2-(tert-butoxy)acetate (0.055 g, 0.080 mmol) in DCE (40 ml) was heated (85° C. oil bath) and then treated with Hoveyda-Grubbs catalyst, 2nd generation (3.53 mg, 5.63 µmol). The reaction was stirred for 2 hrs, then concentrated. The crude mixture in MeOH (1.0 mL) was treated with 10 wt % Pd/C (8.51 mg, 8.00 µmol), and the sealed flask was three times evacuated then back-filled with $H_2$ gas (balloon). The reaction was stirred for 3 hrs, then filtered (0.45 µm syringe tip filter), and the filtrate was concentrated under reduced pressure. The residue was dissolved in MeOH (1.0 mL) and THF (1.0 mL) was treated with 1.0 N NaOH (0.400 mL, 0.400 mmol), and the mixture was heated (75° C. oil bath) for 5 hrs. The reaction was filtered (0.45 µm syringe tip filter) and the crude material was purified via preparative LCMS. Fractions containing the desired product were combined and dried via centrifugal evaporation, to afford the desired product (0.0105 g, 0.016 mmol, 19.57% yield). $^1$H NMR (500 MHz, DMSO-d$_6$) δ 8.40 (s, 1H), 8.05-7.91 (m, 2H), 7.51 (t, J=7.6 Hz, 1H), 7.40-7.27 (m, 2H), 7.10-6.97 (m, 2H), 6.95-6.83 (m, 1H), 6.22 (br. s., 1H), 4.67 (br. s., 1H), 3.80 (t, J=11.3 Hz, 1H), 2.98 (br. s., 1H), 2.56 (d, J=10.1 Hz, 1H), 2.28 (s, 3H), 1.98-1.84 (m, 2H), 1.81-1.60 (m, 6H), 1.59-1.42 (m, 2H), 1.16 (s, 15H), 1.10 (d, J=6.1 Hz, 3H). LCMS (M+H)=644.7.

Example 35

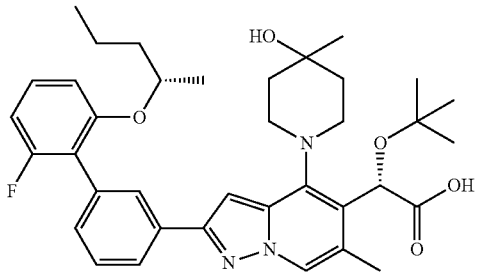 [SMILES: CCC[C@H](C)Oc1cccc(F)c1-c1cccc(-c2cc3c(N4CCC(C)(O)CC4)c([C@H](OC(C)(C)C)C(=O)O)c(C)cn3n2)c1]

(2S)-2-(tert-Butoxy)-2-[2-{3-{2-fluoro-6-[(2S)-pentan-2-yloxy]phenyl}phenyl)-4-(4-hydroxy-4-methylpiperidin-1-yl)-6-methylpyrazolo[1,5-a]pyridin-5-yl] acetic acid This material was isolated as a by-product from the preceding example (0.0263 g, 0.041 mmol, 51.5% yield). $^1$H NMR (500 MHz, DMSO-$d_6$) δ 8.35 (br. s., 1H), 8.05-7.88 (m, 2H), 7.55-7.45 (m, 1H), 7.42-7.27 (m, 2H), 7.20-7.11 (m, 1H), 7.00 (d, J=8.9 Hz, 1H), 6.90 (t, J=8.7 Hz, 1H), 6.26-6.16 (m, 1H), 4.67-4.33 (m, 2H), 3.89 (d, J=10.4 Hz, 1H), 3.43 (br. s., 1H), 3.15 (br. s., 1H), 3.00-2.80 (m, 1H), 2.67 (d, J=11.3 Hz, 1H), 2.28 (s, 3H), 1.82-1.25 (m, 8H), 1.21 (s, 2H), 1.20-1.14 (m, 12H), 0.77 (t, J=7.3 Hz, 3H). LCMS (M+H)=632.6.

Intermediate 71

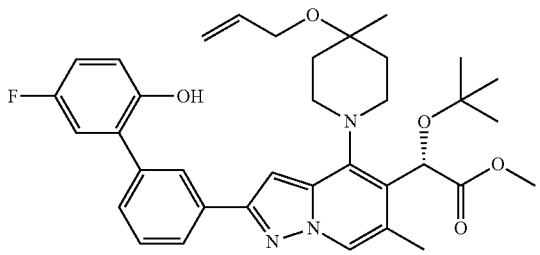 [SMILES: C=CCOC1(C)CCN(c2c([C@H](OC(C)(C)C)C(=O)OC)c(C)cn3nc(-c4cccc(-c5cc(F)ccc5O)c4)cc23)CC1]

(S)-Methyl 2-(4-(4-(allyloxy)-4-methylpiperidin-1-yl)-2-(5'-fluoro-2'-hydroxy-[1,1'-biphenyl]-3-yl)-6-methylpyrazolo[1,5-a]pyridin-5-yl)-2-(tert-butoxy)acetate A solution of ((S)-methyl 2-(4-(4-(allyloxy)-4-methylpiperidin-1-yl)-2-(3-bromophenyl)-6-methylpyrazolo[1,5-a]pyridin-5-yl)-2-(tert-butoxy)acetate (0.203 g, 0.347 mmol), (5-fluoro-2-hydroxyphenyl)boronic acid (0.115 g, 0.715 mmol) and 2.0 M aq. $Na_2CO_3$ (0.55 ml, 1.100 mmol) in DMF (3.47 ml) was sparged with nitrogen for 10 min, treated with Pd(Ph$_3$P)$_4$ (0.030 g, 0.026 mmol), then sparged for 5 min. The reaction was stirred with heating (85° C. oil bath) for 6 hrs, then diluted with water (15 mL) and extracted into Et$_2$O (2×15 mL). The combined extracts were dried (MgSO$_4$), filtered, and concentrated under reduced pressure, and the residue was purified by biotage (12 g SiO$_2$, 0% (3 CV), 0-60% (15 CV), 60% (2 CV), EtOAc in hexanes). Product fractions were pooled and concentrated under reduced pressure, affording the desired product (0.165 g, 0.255 mmol, 73.5% yield) as a viscous oil.

$^1$H NMR (500 MHz, CDCl$_3$) δ 8.12 (s, 1H), 8.05 (t, J=1.5 Hz, 1H), 7.96 (dt, J=7.8, 1.3 Hz, 1H), 7.54 (t, J=7.7 Hz, 1H), 7.46-7.41 (m, 1H), 7.06-6.99 (m, 2H), 6.97-6.90 (m, 2H), 6.46 (s, 1H), 6.09 (ddt, J=17.1, 10.4, 5.1 Hz, 1H), 5.92 (s, 1H), 5.47 (dq, J=17.2, 1.7 Hz, 1H), 5.16 (dd, J=10.4, 1.6 Hz, 1H), 4.00 (dt, J=3.4, 1.5 Hz, 2H), 3.95-3.86 (m, 1H), 3.69 (s, 3H), 3.63-3.55 (m, 1H), 2.94-2.85 (m, 1H), 2.75-2.66 (m, 1H), 2.34 (d, J=0.9 Hz, 3H), 2.02-1.92 (m, 2H), 1.82-1.63 (m, 2H), 1.31 (s, 3H), 1.26 (s, 9H). LCMS (M+H)=617.6.

Intermediate 72

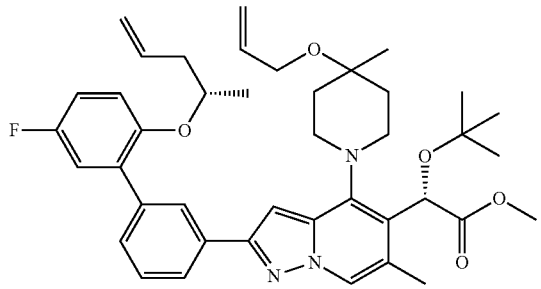 [SMILES: C=CCOC1(C)CCN(c2c([C@H](OC(C)(C)C)C(=O)OC)c(C)cn3nc(-c4cccc(-c5cc(F)ccc5O[C@@H](C)CC=C)c4)cc23)CC1]

(S)-Methyl 2-(4-(4-(allyloxy)-4-methylpiperidin-1-yl)-2-(5'-fluoro-2'-((S)-pent-4-en-2-yloxy)[1,1'-biphenyl]-3-yl)-6-methylpyrazolo[1,5-a]pyridin-5-yl)-2-(tert-butoxy)acetate A solution of (S)-methyl 2-(4-(4-(allyloxy)-4-methylpiperidin-1-yl)-2-(5'-fluoro-2'-hydroxy-[1,1'-biphenyl]-3-yl)-6-methylpyrazolo[1,5-a]pyridin-5-yl)-2-(tert-butoxy)acetate (0.0665 g, 0.108 mmol) in dry THF (1.080 ml) was treated sequentially with (R)-pent-4-en-2-ol (0.028 g, 0.324 mmol), Ph$_3$P (0.085 g, 0.324 mmol) and DEAD (0.051 ml, 0.324 mmol), and the reaction was stirred for 2 hrs. The reaction was diluted with water (10 mL) and extracted into Et$_2$O (10 mL). The organic layer was dried (MgSO$_4$), filtered, and concentrated under reduced pressure and the residue was purified by biotage (24 g SiO$_2$, 0-60% (20 CV), 60% (2 CV), EtOAc in hexanes). Product fractions were pooled and concentrated to afford the desired product (0.055 g, 0.080 mmol, 74.5% yield) as a clear oil. $^1$H NMR (500 MHz, CDCl$_3$) δ 8.15 (s, 1H), 8.06 (t, J=1.6 Hz, 1H), 7.97-7.89 (m, 1H), 7.56 (d, J=7.7 Hz, 1H), 7.50-7.43 (m, 1H), 7.16 (dd, J=9.1, 2.9 Hz, 1H), 7.05-6.92 (m, 3H), 6.52-6.39 (m, 1H), 6.16-5.93 (m, 1H), 5.73 (ddt, J=17.1, 10.2, 7.1 Hz, 1H), 5.53-5.31 (m, 1H), 5.21-5.13 (m, 1H), 5.05-4.94 (m, 2H), 4.09-3.98 (m, 2H), 3.93 (t, J=10.8 Hz, 1H), 3.74-3.67 (m, 3H), 3.60 (t, J=10.9 Hz, 1H), 2.90 (d, J=7.7 Hz, 1H), 2.71 (d, J=10.9 Hz, 1H), 2.41-2.31 (m, 5H), 2.29-2.19 (m, 1H), 2.03-1.92 (m, 2H), 1.77 (td, J=13.1, 4.7 Hz, 1H), 1.69 (td, J=13.1, 4.4 Hz, 1H), 1.30 (s, 3H), 1.26 (s, 9H), 1.16 (d, J=6.1 Hz, 3H). LCMS (M+H)=684.6.

Example 36

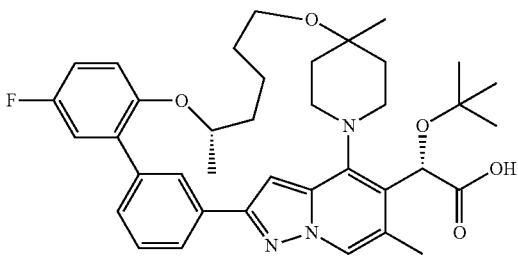 [SMILES: Cc1cn2nc3cc2c(c1[C@H](OC(C)(C)C)C(=O)O)N1CCC(C)(CC1)OCCCC[C@H](C)Oc1ccc(F)cc1-c1cccc-3c1]

(2S)-2-(tert-Butoxy)-2-[(22S)-17-fluoro-4,22,28-trimethyl-21,27-dioxa-1,6,34-triazahexacyclo[26.2.2.1⁶,⁹.1¹⁰,¹⁴.0²,⁷.0¹⁵,²⁰]tetratriaconta-2,4,7,9(34),10(33),11,13,15(20),16,18-decaen-3-yl]acetic acid A solution of (S)-methyl 2-(4-(4-(allyloxy)-4-methylpiperidin-1-yl)-2-(5'-fluoro-2'-((S)-pent-4-en-2-yloxy)-[1,1'-biphenyl]-3-yl)-6-methylpyrazolo[1,5-a]pyridin-5-yl)-2-(tert-butoxy)acetate (0.076 g, 0.111 mmol) in DCE (55 ml) was heated (85° C. oil bath) and once warmed, treated with Hoveyda-Grubbs catalyst, 2nd generation (4.87 mg, 7.78 µmol). The mixture was stirred for 2 hrs, then the reaction was concentrated under reduced pressure. The residue in MeOH (2 mL) was treated with 10 wt % Pd/C (0.012 g, 0.011 mmol), then twice evacuated and backfilled with $H_2$ (balloon). The reaction was stirred for 3 hrs then reaction solids were filtered (0.45 µm syringe tip filter), and the filtrate was concentrated to a viscous oil by rotary evaporator. The crude residue in MeOH (1.5 mL) was treated with 1.0 N NaOH (0.555 mL, 0.555 mmol), and the mixture was heated (85° C. oil bath) for 2 hrs. THF (1.5 mL) was added and the reaction was stirred for 2 hrs, then cooled, diluted with $CH_2Cl_2$ (5 mL) and washed with 1.0 N HCl (5 mL). The organic layer was dried (MgSO4), filtered, and concentrated under reduced pressure. The crude material was purified via preparative LCMS. Fractions containing the desired product were combined and dried via centrifugal evaporation, affording the desired product (0.0166 g, 0.026 mmol, 23.2% yield). ¹H NMR (500 MHz, DMSO-d₆) δ 8.39-8.32 (m, 1H), 8.28-8.12 (m, 1H), 8.05-7.94 (m, 1H), 7.57-7.48 (m, 1H), 7.46-7.38 (m, 1H), 7.24 (d, J=7.6 Hz, 1H), 7.17 (d, J=4.6 Hz, 2H), 7.04-6.88 (m, 1H), 6.30-6.05 (m, 1H), 4.68-4.53 (m, 1H), 3.79 (t, J=12.2 Hz, 1H), 3.13 (br. s., 1H), 2.54 (s, 2H), 2.33-2.25 (m, 3H), 2.03-1.89 (m, 2H), 1.86-1.61 (m, 6H), 1.53 (br. s., 2H), 1.20-1.12 (m, 12H), 1.12-1.08 (m, 3H), 1.07 (d, J=5.8 Hz, 2H). LCMS (M+H)=644.35.

Example 37

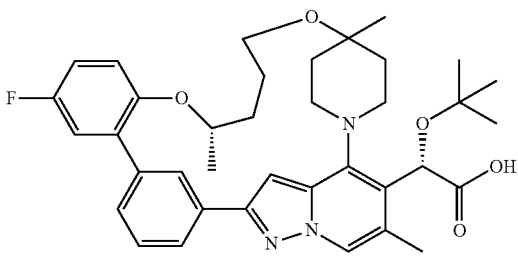 [SMILES: Cc1cn2nc3cc2c(c1[C@H](OC(C)(C)C)C(=O)O)N1CCC(C)(CC1)OCCC[C@H](C)Oc1ccc(F)cc1-c1cccc-3c1]

(2S)-2-(tert-Butoxy)-2-[(22S)-17-fluoro-4,22,27-trimethyl-21,26-dioxa-1,6,33-triazahexacyclo[25.2.2.1⁶,⁹.1¹⁰,¹⁴.0²,⁷.0¹⁵,²⁰]tritriaconta-2,4,7,9(33),10(32),11,13,15(20),16,18-decaen-3-yl]acetic acid This material was isolated as a by-product from the preceding example, affording the methylene shortened product (0.0017 g, 2.214 µmol, 2.0% yield). ¹H NMR (500 MHz, DMSO-d₆) δ 8.42 (s, 1H), 8.32 (br. s., 1H), 7.96-7.78 (m, 1H), 7.60-7.46 (m, 2H), 7.34 (d, J=9.2 Hz, 1H), 7.15 (d, J=5.2 Hz, 2H), 6.93 (s, 1H), 6.16 (br. s., 1H), 4.63 (br. s., 1H), 3.92-3.82 (m, 1H), 3.01 (br. s., 2H), 2.73 (d, J=7.3 Hz, 1H), 2.60-2.53 (m, 1H), 2.37 (d, J=7.6 Hz, 1H), 2.30 (s, 3H), 1.87 (d, J=17.7 Hz, 3H), 1.72-1.50 (m, 4H), 1.24-1.11 (m, 15H). LCMS (M+H)=630.30.

Intermediate 73

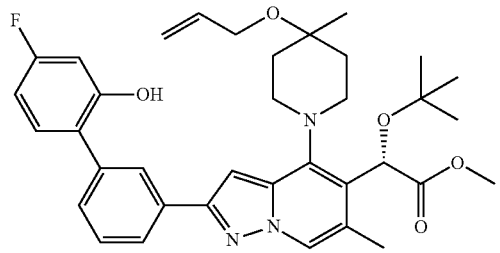 [SMILES: C=CCOC1(C)CCN(c2c([C@H](OC(C)(C)C)C(=O)OC)c(C)cn3nc(-c4cccc(-c5ccc(F)cc5O)c4)cc23)CC1]

(S)-Methyl 2-(4-(4-(allyloxy)-4-methylpiperidin-1-yl)-2-(4'-fluoro-2'-hydroxy-[1,1'-biphenyl]-3-yl)-6-methylpyrazolo[1,5-a]pyridin-5-yl)-2-(tert-butoxy)acetate A solution of ((S)-methyl 2-(4-(4-(allyloxy)-4-methylpiperidin-1-yl)-2-(3-bromophenyl)-6-methylpyrazolo[1,5-a]pyridin-5-yl)-2-(tert-butoxy)acetate (0.203 g, 0.347 mmol), (4-fluoro-2-hydroxyphenyl)boronic acid (0.109 g, 0.685 mmol) and 2.0 M aq. $Na_2CO_3$ (0.55 ml, 1.100 mmol) in DMF (2 mL) was sparged with nitrogen for 10 min, treated with Pd(Ph₃P)₄ (0.028 g, 0.024 mmol), then sparged for 5 min. The reaction was stirred with heating (85° C. oil bath) for 6 hrs, then diluted with water (15 mL) and extracted into $Et_2O$ (2×15 mL). The combined extracts were dried (MgSO₄), filtered, and concentrated under reduced pressure, and the residue was purified by biotage (12 g SiO₂, 0% (3 CV), 0-60% (15 CV), 60% (2 CV), EtOAc in hexanes). Product fractions were pooled and concentrated under reduced pressure, affording the desired product (0.150 g, 0.244 mmol, 70.1% yield) as an off-white glassy solid. ¹H NMR (500 MHz, CDCl₃) δ 8.13 (s, 1H), 8.02-7.95 (m, 2H), 7.56 (t, J=7.6 Hz, 1H), 7.44-7.37 (m, 1H), 7.28-7.25 (m, 1H), 7.02 (s, 1H), 6.78-6.70 (m, 2H), 6.48-6.36 (m, 1H), 6.08 (ddt, J=17.1, 10.4, 5.1 Hz, 1H), 5.75-5.67 (m, 1H), 5.51-5.30 (m, 1H), 5.14 (dd, J=10.4, 1.7 Hz, 1H), 4.09-3.97 (m, 2H), 3.96-3.87 (m, 1H), 3.74-3.67 (m, 3H), 3.63-3.54 (m, 1H), 2.90 (d, J=7.4 Hz, 1H), 2.71 (d, J=11.0 Hz, 1H), 2.35 (d, J=0.9 Hz, 3H), 2.03-1.93 (m, 2H), 1.81-1.64 (m, 2H), 1.31 (s, 2H), 1.26 (s, 9H). LCMS (M+H)=617.7.

Intermediate 74

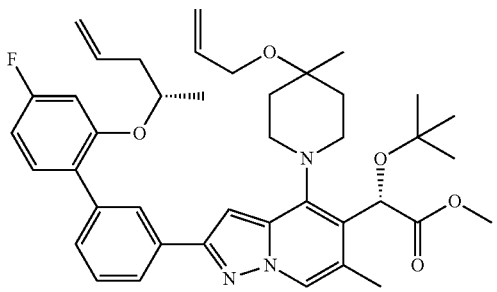 [SMILES: C=CCOC1(C)CCN(c2c([C@H](OC(C)(C)C)C(=O)OC)c(C)cn3nc(-c4cccc(-c5ccc(F)cc5O[C@@H](C)CC=C)c4)cc23)CC1]

(S)-Methyl 2-(4-(4-(allyloxy)-4-methylpiperidin-1-yl)-2-(4'-fluoro-2'-((S)-pent-4-en-2-yloxy)-[1,1'-biphenyl]-3-yl)-6-methylpyrazolo[1,5-a]pyridin-5-yl)-2-(tert-butoxy)acetate: A solution of (S)-methyl 2-(4-(4-(allyloxy)-4-methylpiperidin-1-yl)-2-(4'-fluoro-2'-hydroxy-[1,1'-biphenyl]-3-yl)-6-methylpyrazolo[1,5-a]pyridin-5-yl)-2-(tert-butoxy)acetate (0.0958 g, 0.156 mmol) in dry THF (1.556 ml) was treated sequentially with (R)-pent-4-en-2-ol (0.040 g, 0.467 mmol), Ph$_3$P (0.122 g, 0.467 mmol) and DEAD (0.074 ml, 0.467 mmol), and the reaction was stirred for 2 hrs. The reaction was diluted with water (10 mL) and extracted into Et$_2$O (10 mL). The organic layer was dried (MgSO$_4$), filtered, and concentrated under reduced pressure, and the residue was purified by biotage (12 g SiO$_2$, 0% (3 CV), 0-60% (15 CV), 60% (2 CV), EtOAc in hexanes). Product fractions were pooled and concentrated to afford (0.046 g, 0.067 mmol, 43.2% yield) as a clear oil. $^1$H NMR (500 MHz, CDCl$_3$) δ 8.16 (s, 1H), 8.08-8.01 (m, 1H), 7.91 (d, J=7.7 Hz, 1H), 7.59-7.51 (m, 1H), 7.49-7.43 (m, 1H), 7.39 (dd, J=8.3, 7.0 Hz, 1H), 7.02 (s, 1H), 6.81-6.68 (m, 2H), 6.51-6.39 (m, 1H), 6.15-6.02 (m, 1H), 5.79 (ddt, J=17.1, 10.1, 7.1 Hz, 1H), 5.47 (dd, J=17.1, 1.8 Hz, 1H), 5.15 (dd, J=10.4, 1.6 Hz, 1H), 5.10-5.02 (m, 2H), 4.01 (d, J=5.2 Hz, 1H), 3.94 (t, J=11.3 Hz, 1H), 3.73-3.69 (m, 3H), 3.65-3.57 (m, 1H), 2.92 (d, J=9.6 Hz, 1H), 2.73 (d, J=10.4 Hz, 1H), 2.48-2.40 (m, 1H), 2.37 (d, J=0.8 Hz, 3H), 2.35-2.28 (m, 1H), 2.03-1.95 (m, 2H), 1.78 (td, J=13.2, 4.8 Hz, 1H), 1.70 (td, J=13.0, 4.3 Hz, 1H), 1.32 (s, 2H), 1.28 (s, 9H), 1.27 (s, 1H). LCMS (M+H)=684.4.

Example 38

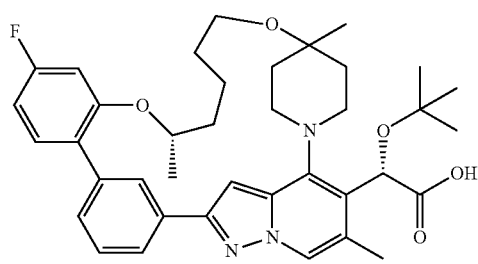 [SMILES: Cc1cn2nc3cc2c(c1[C@H](OC(C)(C)C)C(=O)O)N1CCC(C)(CC1)OCCCC[C@H](C)Oc1cc(F)ccc1-c1cccc-3c1]

(2S)-2-(tert-Butoxy)-2-[(22S)-18-fluoro-4,22,28-trimethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetic acid A solution of (S)-methyl 2-(4-(4-(allyloxy)-4-methylpiperidin-1-yl)-2-(4'-fluoro-2'-((S)-pent-4-en-2-yloxy)-[1,1'-biphenyl]-3-yl)-6-methylpyrazolo[1,5-a]pyridin-5-yl)-2-(tert-butoxy)acetate (0.075 g, 0.110 mmol) in dry DCE (70 mL) was heated (85° C. oil bath) then treated with Hoveyda-Grubbs catalyst, 2nd generation (0.069 g, 0.110 mmol), and stirred for 2 hrs. The reaction was concentrated under reduced pressure, and the residue in MeOH (1.5 mL) was treated with 10 wt % Pd/C (0.012 g, 0.110 mmol), then three times evacuated and back-filled with H$_2$ gas (balloon). The reaction was stirred for 3.5 hrs then filtered (0.45 μm syringe tip filter) and the filtrate was concentrated. The reaction was re-initiated using fresh MeOH (1.5 mL) and 10 wt % Pd/C (0.012 g, 0.110 mmol). The reaction was stirred for 4.5 hrs, then filtered (0.45 μm syringe tip filter). The filtrate was treated with 1.0 N NaOH (0.304 ml, 0.304 mmol), and the mixture was heated (75° C. oil bath) for 5 hrs, then heating was reduced (50° C.) and stirred for 16 hrs. Reaction temperature was raised (75° C.) and stirred for 2 hrs. The reaction was cooled, then diluted with CH$_2$Cl$_2$ (15 mL) and washed with 0.5 M HCl (15 mL), then brine. The organic layer was dried (MgSO$_4$), filtered, and concentrated under reduced pressure, and the residue was purified by preparative LCMS. Fractions containing the desired product were combined and dried via centrifugal evaporation, affording the product (0.0203 g, 0.030 mmol, 49.8% yield). $^1$H NMR (500 MHz, DMSO-d$_6$) δ 8.42-8.33 (m, 1H), 8.22-8.06 (m, 1H), 8.03-7.92 (m, 1H), 7.51 (t, J=7.8 Hz, 1H), 7.44-7.30 (m, 2H), 7.09 (d, J=10.7 Hz, 1H), 7.05-6.90 (m, 1H), 6.84 (t, J=8.1 Hz, 1H), 6.35-6.11 (m, 1H), 4.72 (br. s., 1H), 3.78 (t, J=11.6 Hz, 1H), 3.04 (br. s., 1H), 2.54 (s, 2H), 2.36-2.20 (m, 3H), 2.05-1.87 (m, 2H), 1.87-1.63 (m, 6H), 1.52 (d, J=7.9 Hz, 2H), 1.23-1.03 (m, 15H). Note: piperidine proton signals are partially broadened and do not integrate to their full complement. LCMS (M+H)=644.4.

Intermediate 75

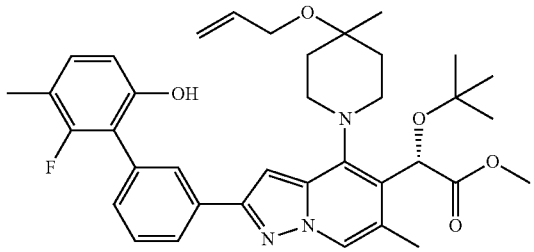

(S)-Methyl 2-(4-(4-(allyloxy)-4-methylpiperidin-1-yl)-2-(2'-fluoro-6'-hydroxy-3'-methyl-[1,1'-biphenyl]-3-yl)-6-methylpyrazolo[1,5-a]pyridin-5-yl)-2-(tert-butoxy)acetate A solution of ((S)-methyl 2-(4-(4-(allyloxy)-4-methylpiperidin-1-yl)-2-(3-bromophenyl)-6-methylpyrazolo[1,5-a]pyridin-5-yl)-2-(tert-butoxy)acetate (0.105 g, 0.180 mmol), (2-fluoro-6-hydroxy-3-methylphenyl)boronic acid (0.052 g, 0.306 mmol) and 2.0 M aq. Na$_2$CO$_3$ (0.269 ml, 0.539 mmol) in DMF (1.796 ml) was sparged with nitrogen for 10 min, treated with Pd(Ph$_3$P)$_4$ (0.015 g, 0.013 mmol), then sparged for 5 min. The reaction was stirred with heating (85° C. oil bath) for 3 hrs, then cooled, diluted with water (15 mL) and extracted into Et$_2$O (2×15 mL). The combined extracts were washed with brine, then dried (MgSO$_4$), filtered, and concentrated under reduced pressure. The residue was purified by biotage (12 g SiO$_2$, 0% (3 CV), 0-60% (15 CV), 60% (2 CV), EtOAc in hexanes), affording the desired product (0.071 g, 0.113 mmol, 62.8% yield) as a clear film. $^1$H NMR (500 MHz, CDCl$_3$) δ 8.13 (s, 1H), 8.00 (dt, J=7.8, 1.3 Hz, 1H), 7.97 (s, 1H), 7.57 (t, J=7.6 Hz, 1H), 7.39 (d, J=7.4 Hz, 1H), 7.06 (t, J=8.4 Hz, 1H), 7.01 (s, 1H), 6.74 (dd, J=8.4, 0.8 Hz, 1H), 6.46 (s, 1H), 6.07 (ddt, J=17.1, 10.4, 5.1 Hz, 1H), 5.52 (s, 1H), 5.45 (dq, J=17.1, 1.6 Hz, 1H), 5.13 (dd, J=10.4, 1.7 Hz, 1H), 4.02-3.96 (m, 2H), 3.95-3.86 (m, 1H), 3.68 (s, 3H), 3.63-3.55 (m, 1H), 2.89 (d, J=8.7 Hz, 1H), 2.70 (d, J=11.0 Hz, 1H), 2.35 (d, J=0.9 Hz, 3H), 2.25 (d, J=1.7 Hz, 3H), 2.01-1.92 (m, 2H), 1.68 (s, 2H), 1.30 (s, 3H), 1.26-1.25 (m, 9H). LCMS (M+H)=630.6.

Intermediate 76

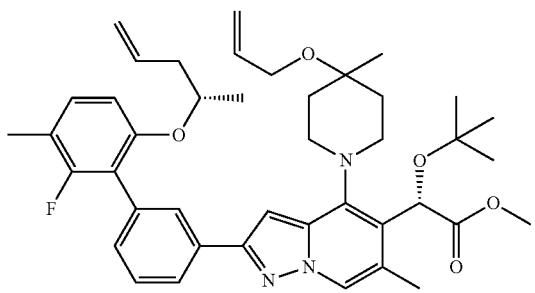

(S)-Methyl 2-(4-(4-(allyloxy)-4-methylpiperidin-1-yl)-2-(2'-fluoro-3'-methyl-6'-((S)-pent-4-en-2-yloxy)-[1,1'-biphenyl]-3-yl)-6-methylpyrazolo[1,5-a]pyridin-5-yl)-2-(tert-butoxy)acetate A solution of (S)-methyl 2-(4-(4-(allyloxy)-4-methylpiperidin-1-yl)-2-(2'-fluoro-6'-hydroxy-3'-methyl-[1,1'-biphenyl]-3-yl)-6-methylpyrazolo[1,5-a]pyridin-5-yl)-2-(tert-butoxy)acetate (0.071 g, 0.113 mmol), (R)-pent-4-en-2-ol (0.029 g, 0.338 mmol) and Ph$_3$P (0.089 g, 0.338 mmol) in dry THF (1.127 ml) was treated with DEAD (0.054 ml, 0.338 mmol), and the mixture was stirred for 16 hrs. The mixture was diluted with water (10 mL) and extracted into Et$_2$O (10 mL), then dried (MgSO$_4$), filtered, and concentrated under reduced pressure. The residue was purified via preparative LCMS. Product fractions were combined and dried via centrifugal evaporation. affording the desired product (0.050 g, 0.072 mmol, 63.8% yield). $^1$H NMR (500 MHz, CDCl$_3$) δ 8.17 (s, 1H), 8.00-7.92 (m, 2H), 7.48 (t, J=7.6 Hz, 1H), 7.41 (d, J=7.6 Hz, 1H), 7.09 (t, J=8.4 Hz, 1H), 7.01 (s, 1H), 6.71 (d, J=8.2 Hz, 1H), 6.46 (s, 1H), 6.06 (ddt, J=17.1, 10.4, 5.1 Hz, 1H), 5.76-5.62 (m, 1H), 5.44 (dq, J=17.1, 1.7 Hz, 1H), 5.11 (dd, J=10.4, 1.6 Hz, 1H), 5.01-4.97 (m, 1H), 4.96 (d, J=1.1 Hz, 1H), 4.28-4.21 (m, 1H), 4.01-3.97 (m, 2H), 3.92 (t, J=11.1 Hz, 1H), 3.72-3.66 (m, 3H), 3.59 (t, J=11.1 Hz, 1H), 2.94-2.66 (m, 2H), 2.36 (d, J=0.9 Hz, 3H), 2.35-2.30 (m, 1H), 2.27 (d, J=1.6 Hz, 3H), 2.24-2.15 (m, 1H), 2.02-1.91 (m, 2H), 1.81-1.63 (m, 2H), 1.30 (s, 3H), 1.26 (s, 9H), 1.15 (d, J=6.1 Hz, 3H). LCMS (M+H)=698.7.

Example 39

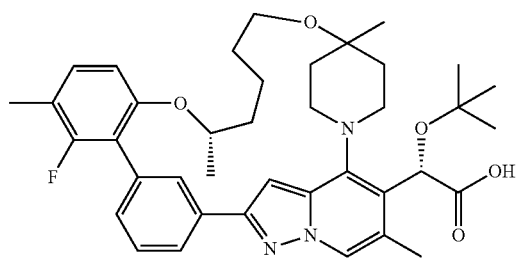 [SMILES: Cc1ccc2c(c1F)-c1cccc(c1)-c1cc3c(c([C@H](OC(C)(C)C)C(=O)O)c(C)cn3n1)N1CCC(C)(CC1)OCCCC[C@H](C)O2]

(2S)-2-(tert-Butoxy)-2-[(22S)-16-fluoro-4,17,22,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetic acid A solution of (S)-methyl 2-(4-(4-(allyloxy)-4-methylpiperidin-1-yl)-2-(2'-fluoro-3'-methyl-6'-((S)-pent-4-en-2-yloxy)-[1,1'-biphenyl]-3-yl)-6-methylpyrazolo[1,5-a]pyridin-5-yl)-2-(tert-butoxy)acetate (0.0502 g, 0.072 mmol) in dry DCE (36.0 ml) was heated (80° C. oil bath) and then treated with Hoveyda-Grubbs catalyst, 2nd generation (3.16 mg, 5.04 μmol). The reaction was stirred for 4 hrs, then cooled and concentrated. The residue in MeOH (2.0 mL) was treated with 10 wt % Pd/C (8 mg, 7.52 μmol), and the flask was three times evacuated and back-filled with hydrogen gas. The reaction was stirred for 3 hrs then filtered (0.45 μm syringe tip filter), concentrated. The residue in THF (2 mL) was treated with 1.0 N NaOH (0.360 mL, 0.360 mmol), and stirred with heating (70° C. oil bath) for 2 hrs, then crude material was purified via preparative LCMS. Product fractions were combined and dried via centrifugal evaporation. affording the desired product (0.0052 g, 0.008 mmol, 11% yield). $^1$H NMR (500 MHz, DMSO-d$_6$) δ 8.40 (s, 1H), 7.98 (d, J=7.6 Hz, 1H), 7.50 (t, J=7.8 Hz, 1H), 7.34 (d, J=6.1 Hz, 1H), 7.22 (t, J=8.5 Hz, 1H), 6.99 (s, 1H), 6.92 (d, J=8.5 Hz, 1H), 6.23 (s, 1H), 4.61 (br. s., 1H), 3.78 (t, J=11.1 Hz, 1H), 2.95 (d, J=8.9 Hz, 1H), 2.54 (d, J=9.5 Hz, 1H), 2.28 (s, 3H), 2.20 (s, 3H), 1.90 (d, J=12.8 Hz, 2H), 1.80-1.40 (m, 8H), 1.16 (s, 12H), 1.07 (d, J=6.1 Hz, 3H). Note: piperidine proton signals are partially broadened and do not integrate to their full complement. LCMS (M+H)=658.6.

Example 40

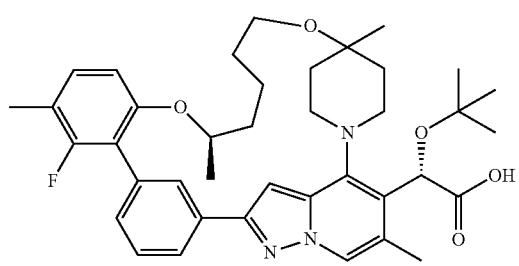 [SMILES: Cc1ccc2c(c1F)-c1cccc(c1)-c1cc3c(c([C@H](OC(C)(C)C)C(=O)O)c(C)cn3n1)N1CCC(C)(CC1)OCCCC[C@@H](C)O2]

(2S)-2-(tert-Butoxy)-2-[(22R)-16-fluoro-4,17,22,28-tetramethyl-21,27-dioxa-1,6,34-triazahexacyclo [26.2.2.1$^{6,9}$.1$^{10,14}$.0$^{2,7}$.0$^{15,20}$]tetratriaconta-2,4,7,9 (34),10(33),11,13,15(20),16,18-decaen-3-yl]acetic acid This material was isolated as a by-product from the preceding example, affording an opposite diasteriomer product (0.0037 g, 5.63 µmol, 7.8% yield). $^1$H NMR (500 MHz, DMSO-d$_6$) δ 8.41 (s, 1H), 7.92 (d, J=8.2 Hz, 1H), 7.33 (d, J=6.7 Hz, 1H), 7.22 (t, J=8.7 Hz, 1H), 6.97-6.83 (m, 2H), 6.33 (s, 1H), 4.58 (br. s., 1H), 3.81-3.70 (m, 1H), 2.77 (br. s., 1H), 2.58 (d, J=8.9 Hz, 1H), 2.31 (s, 3H), 2.20 (s, 3H), 1.83 (br. s., 4H), 1.73-1.55 (m, 5H), 1.49 (br. s., 1H), 1.19 (s, 9H), 1.17 (br. s., 3H), 1.09 (d, J=5.8 Hz, 3H). Note: piperidine proton signals are partially broadened and do not integrate to their full complement. LCMS (M+H)=658.6.

Example 41

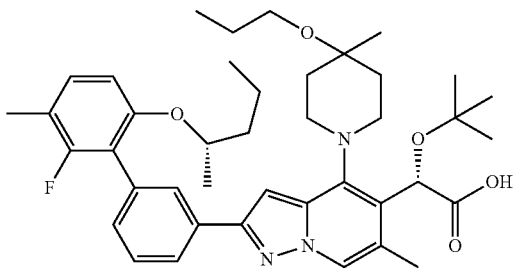 [SMILES: CCCOC1(C)CCN(c2c([C@H](OC(C)(C)C)C(=O)O)c(C)cn3nc(-c4cccc(-c5c(O[C@@H](C)CCC)ccc(C)c5F)c4)cc23)CC1]

(2S)-2-(tert-Butoxy)-2-[2-(3-{2-fluoro-3-methyl-6-[(2S)-pentan-2-yloxy]phenyl}phenyl)-6-methyl-4-(4-methyl-4-propoxypiperidin-1-yl)pyrazolo[1,5-a]pyridin-5-yl]acetic acid This material was isolated as a by-product from the preceding example, affording the non-macrocyclic product (0.0101 g, 0.147 mmol, 20.4% yield). $^1$H NMR (500 MHz, DMSO-d$_6$) δ 8.37 (s, 1H), 7.89 (d, J=7.6 Hz, 1H), 7.81 (br. s., 1H), 7.57-7.47 (m, 1H), 7.33 (d, J=7.6 Hz, 1H), 7.25-7.12 (m, 1H), 6.94 (s, 1H), 6.87 (d, J=8.5 Hz, 1H), 6.24 (s, 1H), 4.42-4.29 (m, 1H), 3.78 (t, J=10.8 Hz, 1H), 2.88 (br. s., 1H), 2.60 (d, J=8.9 Hz, 1H), 2.29 (s, 4H), 2.21 (s, 4H), 1.93-1.21 (m, 11H), 1.17 (s, 12H), 1.10 (d, J=6.1 Hz, 3H), 0.93 (t, J=7.2 Hz, 3H), 0.76-0.70 (m, 3H). LCMS (M+H)=688.8.

Intermediate 77

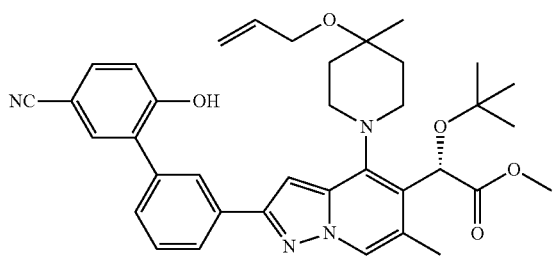 [SMILES: C=CCOC1(C)CCN(c2c([C@H](OC(C)(C)C)C(=O)OC)c(C)cn3nc(-c4cccc(-c5cc(C#N)ccc5O)c4)cc23)CC1]

(S)-Methyl 2-(4-(4-(allyloxy)-4-methylpiperidin-1-yl)-2-(5'-cyano-2'-hydroxy-[1,1'-biphenyl]-3-yl)-6-methylpyrazolo[1,5-a]pyridin-5-yl)-2-(tert-butoxy) acetate A solution of ((S)-methyl 2-(4-(4-(allyloxy)-4-methylpiperidin-1-yl)-2-(3-bromophenyl)-6-methylpyrazolo[1,5-a] pyridin-5-yl)-2-(tert-butoxy)acetate (0.204 g, 0.349 mmol), (5-cyano-2-hydroxyphenyl)boronic acid (0.117 g, 0.689 mmol) and 2.0 M aq. Na$_2$CO$_3$ (0.55 ml, 1.100 mmol) in DMF (2 mL) was sparged with nitrogen for 10 min, treated with Pd(Ph$_3$P)$_4$ (0.029 g, 0.025 mmol), then sparged for 5 min. The reaction was stirred with heating (85° C. oil bath) for 6 hrs then at room temperature for 16 hrs. The reaction was diluted with water (15 mL) and extracted into Et$_2$O (2×15 mL). The combined extracts were dried (MgSO$_4$), filtered, and concentrated under reduced pressure, and the residue was purified by biotage (12 g SiO$_2$, 0% (3 CV), 0-60% (15 CV), 60% (2 CV), EtOAc in hexanes). Product fractions were pooled and concentrated under reduced pressure, affording the desired product (0.153 g, 0.246 mmol, 70.4% yield) as an off-white glassy solid. $^1$H NMR (500 MHz, CDCl$_3$) δ 8.11 (s, 1H), 8.09 (t, J=1.6 Hz, 1H), 8.01-7.97 (m, 1H), 7.62 (d, J=2.2 Hz, 1H), 7.59 (t, J=7.6 Hz, 1H), 7.53 (dd, J=8.4, 2.1 Hz, 1H), 7.43-7.39 (m, 1H), 7.06 (d, J=8.4 Hz, 1H), 7.03 (s, 1H), 6.95 (br. s., 1H), 6.45 (s, 1H), 6.10 (ddt, J=17.1, 10.4, 5.1 Hz, 1H), 5.53-5.43 (m, 1H), 5.17 (dd, J=10.4, 1.7 Hz, 1H), 4.04-3.98 (m, 2H), 3.92 (t, J=10.7 Hz, 1H), 3.72-3.65 (m, 3H), 3.63-3.55 (m, 1H), 2.95-2.85 (m, 1H), 2.75-2.66 (m, 1H), 2.34 (d, J=0.9 Hz, 3H), 2.03-1.93 (m, 2H), 1.77 (td, J=13.2, 4.6 Hz, 1H), 1.69 (td, J=13.1, 4.4 Hz, 1H), 1.31 (s, 3H), 1.26 (s, 9H). LCMS (M+H)= 623.5.

Intermediate 78

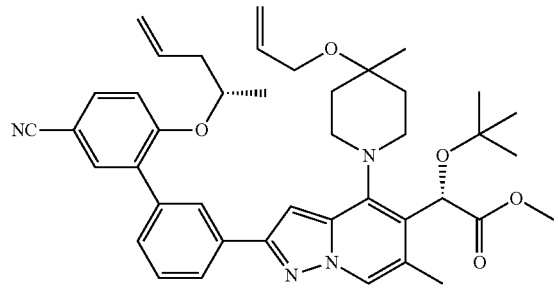 [SMILES: C=CCOC1(C)CCN(c2c([C@H](OC(C)(C)C)C(=O)OC)c(C)cn3nc(-c4cccc(-c5cc(C#N)ccc5O[C@@H](C)CC=C)c4)cc23)CC1]

(S)-Methyl 2-(4-(4-(allyloxy)-4-methylpiperidin-1-yl)-2-(5'-cyano-2'-((S)-pent-4-en-2-yloxy)-[1,1'-biphenyl]-3-yl)-6-methylpyrazolo[1,5-a]pyridin-5-yl)-2-(tert-butoxy)acetate A solution of (S)-methyl 2-(4-(4-(allyloxy)-4-methylpiperidin-1-yl)-2-(5'-cyano-2'-hydroxy-[1,1'-biphenyl]-3-yl)-6-methylpyrazolo[1,5-a]pyridin-5-yl)-2-(tert-butoxy)acetate (0.0954 g, 0.153 mmol) in dry THF (1.532 ml) was treated sequentially with (R)-pent-4-en-2-ol (0.040 g, 0.460 mmol), Ph$_3$P (0.121 g, 0.460 mmol) and DEAD (0.073 ml, 0.460 mmol), and the reaction was stirred for 2 hrs. The reaction was diluted with water (10 mL) and extracted into Et$_2$O (10 mL). The organic layer was dried (MgSO$_4$), filtered, and concentrated under reduced pressure, and the residue was purified by biotage (40 g SiO$_2$, 0-40% (15 CV), 60% (2 CV), EtOAc in hexanes). Product fractions were pooled and concentrated under reduced pressure, affording the product (0.101 g, 0.146 mmol, 95% yield) as a clear oil. LCMS (M+H)=693.6.

Intermediate 79

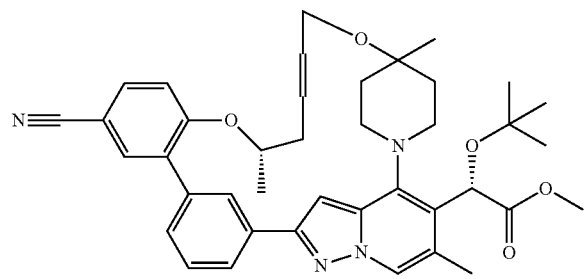 [SMILES: COC(=O)[C@@H](OC(C)(C)C)c1c(C)cn2nc3cc2c1N1CCC(C)(CC1)OCC=CC[C@H](C)Oc1ccc(C#N)cc1-c1cccc-3c1]

Methyl (2S)-2-(tert-butoxy)-2-[(22S)-17-cyano-4,22, 28-trimethyl-21,27-dioxa-1,6,34-triazahexacyclo [26.2.2.1$^{6,9}$.1$^{10,14}$.0$^{2,7}$.0$^{15,20}$]tetratriaconta-2,4,7,9 (34),10(33),11,13,15(20),16,18,24-undecaen-3-yl] acetate A solution of (S)-methyl 2-(4-(4-(allyloxy)-4-methylpiperidin-1-yl)-2-(5'-cyano-2'-((S)-pent-4-en-2-yloxy)-[1,1'-biphenyl]-3-yl)-6-methylpyrazolo[1,5-a]pyridin-5-yl)-2-(tert-butoxy)acetate (0.104 g, 0.151 mmol) in DCE (100 mL) was warmed (85° C. oil bath) then treated with Hoveyda-Grubbs catalyst, 2nd generation (9.4 mg, 0.015 mmol). The reaction was stirred for 2 hrs. The reaction was concentrated, and the residue was purified by biotage (12 g SiO$_2$, 0% (3 CV), 0-60% (15 CV), 60% (2 CV), EtOAc in hexanes). Product fractions were pooled and concentrated under reduced pressure, affording the desired product (0.082 g, 0.124 mmol, 82% yield). LCMS (M+H)=663.35.

Example 42

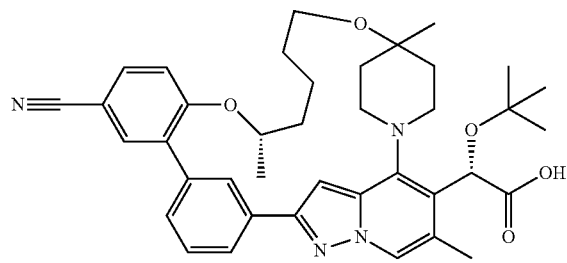 [SMILES: Cc1cn2nc3cc2c(c1[C@H](OC(C)(C)C)C(=O)O)N1CCC(C)(CC1)OCCCC[C@H](C)Oc1ccc(C#N)cc1-c1cccc-3c1]

(2S)-2-(tert-Butoxy)-2-[(22S)-17-cyano-4,22,28-trimethyl-21,27-dioxa-1,6,34-triazahexacyclo [26.2.2.1$^{6,9}$.1$^{10,14}$.0$^{2,7}$.0$^{15,20}$]tetratriaconta-2,4,7,9 (34),10(33),11,13,15(20),16,18-decaen-3-yl]acetic acid A solution of methyl (2S)-2-(tert-butoxy)-2-[(22S)-17-cyano-4,22,28-trimethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34), 10(33),11,13,15(20),16,18,24-undecaen-3-yl]acetate (0.082 g, 0.124 mmol) in MeOH (3 mL) was treated with 10 wt % Pd/C (0.013 g, 0.012 mmol), then three times evacuated and back-filled with H$_2$ gas (balloon). The reaction was stirred for 2 hrs, then filtered (0.45 μm syringe tip filter) and the filtrate was concentrated under reduced pressure. The residue was re-dissolved in MeOH (0.75 mL) and THF (0.75 mL, treated with 5.0 N NaOH (0.083 mL, 0.414 mmol), and the mixture was heated (75° C. oil bath) for 90 min, then cooled and diluted with CH$_2$Cl$_2$ (15 mL). The suspension was washed with 1.0 N HCl (5 mL), then brine, then concentrated. The crude material was purified via preparative LCMS. Fractions containing the desired product were combined and dried via centrifugal evaporation, to afford the desired product (0.0135 g, 0.021 mmol, 17% yield). $^1$H NMR (500 MHz, DMSO-d$_6$) δ 8.39 (s, 1H), 8.19 (s, 1H), 8.07 (d, J=7.6 Hz, 1H), 7.81 (s, 2H), 7.55 (t, J=7.6 Hz, 1H), 7.44 (d, J=7.6 Hz, 1H), 7.37 (d, J=9.2 Hz, 1H), 7.03 (s, 1H), 6.21 (br. s., 1H), 4.83 (br. s., 1H), 3.76 (t, J=11.9 Hz, 1H), 2.98 (d, J=8.2 Hz, 1H), 2.91-2.66 (m, 1H), 2.60-2.52 (m, 1H), 2.28 (s, 3H), 2.03-1.87 (m, 2H), 1.87-1.65 (m, 6H), 1.51 (d, J=10.1 Hz, 2H), 1.18-1.15 (m, 11H), 1.13 (br. s., 3H). LCMS (M+H)=651.7.

It will be evident to one skilled in the art that the present disclosure is not limited to the foregoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:
1. A compound of Formula I or Formula II

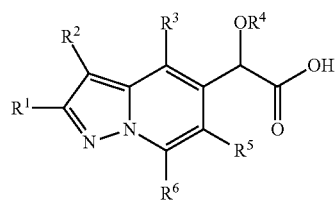

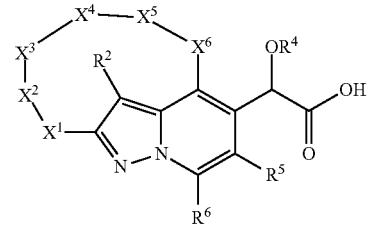

where:
R$^1$ is —CON(R$^7$)(R$^8$);
or R$^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, indolyl, benzofuranyl, benzothiophenyl, benzimidazolyl, or phenyl, and is substituted with 0-3 substituents selected from cyano, halo, alkyl, haloalkyl, alkenyl, alkoxy, alkenoxy, Ar$^1$, (Ar$^1$) alkyl, and (Ar$^1$)O;
R$^2$ is hydrogen or alkyl;
R$^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

or $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

$R^4$ is alkyl or haloalkyl;

$R^5$ is alkyl;

$R^6$ is hydrogen or alkyl;

$R^7$ is $Ar^1$ or $(Ar^1)$alkyl;

$R^8$ is hydrogen or alkyl;

$Ar^1$ is phenyl or pyridinyl and is substituted with 0-3 substituents selected from halo, cyano, alkyl, haloalkyl, alkoxy, haloalkoxy, and alkenyloxy;

$X^1$ is —CONH—;

or $X^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, benzimidazolyl, or phenyl;

$X^2$ is phenyl or benzyl and is substituted with 0-3 substituents selected from cyano, halo, alkyl, haloalkyl, alkoxy, and haloalkoxy;

$X^3$ is O or absent;

$X^4$ is alkylene or alkenylene;

$X^5$ is O or absent; and $X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;

or a pharmaceutically acceptable salt thereof.

2. A compound of claim 1 where:

$R^1$ is —CON($R^7$)($R^8$);

or $R^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, indolyl, benzofuranyl, benzothiophenyl, benzimidazolyl, or phenyl, and is substituted with 0-3 substituents selected from halo, alkyl, haloalkyl, alkenyl, $Ar^1$, $(Ar^1)$alkyl, and $(Ar^1)$O;

$R^2$ is hydrogen or alkyl;

$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

or $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

$R^4$ is alkyl or haloalkyl;

$R^5$ is alkyl;

$R^6$ is hydrogen or alkyl;

$R^7$ is $Ar^1$ or $(Ar^1)$alkyl;

$R^8$ is hydrogen or alkyl;

$Ar^1$ is phenyl or pyridinyl and is substituted with 0-3 substituents selected from halo, cyano, alkyl, haloalkyl, alkoxy, haloalkoxy, and alkenyloxy;

$X^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, benzimidazolyl, or phenyl;

$X^2$ is benzyl wherein the benzyl can be substituted with 0-3 substituents selected from halo, alkyl, haloalkyl, alkoxy, and haloalkoxy;

$X^3$ is O or absent;

$X^4$ is alkylene or alkenylene;

$X^5$ is O or absent; and $X^6$ is azetidinyl, pyrrolidinyl, piperidinyl, piperazinyl, morpholinyl, homopiperidinyl, homopiperazinyl, or homomorpholinyl, and is substituted with 0-3 halo or alkyl substituents;

or a pharmaceutically acceptable salt thereof.

3. A compound of claim 1 according to Formula I.

4. A compound of claim 3 where $R^1$ is —CON($R^7$)($R^8$);

or $R^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, indolyl, benzofuranyl, benzothiophenyl, benzimidazolyl, or phenyl, and is substituted with 0-3 substituents selected from halo, alkyl, haloalkyl, alkenyl, $Ar^1$, $(Ar^1)$alkyl, and $(Ar^1)$O;

$R^2$ is hydrogen;

$R^3$ is azetidinyl, pyrrolidinyl, piperidinyl, piperazinyl, morpholinyl, homopiperidinyl, homopiperazinyl, or homomorpholinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

or $R^3$ is cycloalkyl, cycloalkenyl, chromanyl, oxazinyl, or dihydropyranoquinolinyl, and is substituted with 0-3 substituents selected from halo, alkyl, haloalkyl, hydroxyalkyl, alkoxyalkyl, alkenyl, cycloalkyl, hydroxy, alkoxy, haloalkoxy, alkenyloxy, and phenyl;

$R^4$ is alkyl;

$R^5$ is alkyl;

$R^6$ is hydrogen;

$R^7$ is $(Ar^1)$alkyl;

$R^8$ is hydrogen; and $Ar^1$ is phenyl or pyridinyl and is substituted with 0-3 substituents selected from halo, cyano, alkyl, haloalkyl, alkoxy, haloalkoxy, and alkenyloxy;

or a pharmaceutically acceptable salt thereof.

5. A compound of claim 3 where $R^1$ is —CON($R^7$)($R^8$).

6. A compound of claim 3 where $R^1$ is pyrrolyl, furanyl, thienyl, pyrazolyl, isoxazolyl, isothiazolyl, imidazolyl, oxazolyl, thiazolyl, triazolyl, oxadiazolyl, thiadiazolyl, indolyl, benzofuranyl, benzothiophenyl, benzimidazolyl, or phenyl, and is substituted with 0-3 substituents selected from halo, alkyl, haloalkyl, alkenyl, $Ar^1$, $(Ar^1)$alkyl, and $(Ar^1)$O.

7. A compound of claim 3 where $R^3$ piperidinyl substituted with 0-3 halo or alkyl substituents.

8. A compound of claim 1 according to Formula II.

9. A compound of claim 8 where $X^2$ is benzyl substituted with 0-3 substituents selected from cyano, halo, alkyl, haloalkyl, alkoxy, and haloalkoxy.

10. A compound of claim 8 where $X^6$ is piperidinyl substituted with 0-3 halo or alkyl substituents.

11. A compound of claim 1 selected from the group consisting of (2S)-2-(tert-Butoxy)-2-(2-((4-fluoro-3-methylbenzyl)carbamoyl)-4-(8-fluoro-5-methylchroman-6-yl)-6-methylpyrazolo[1,5-a]pyridin-5-yl)acetic acid;

(2S)-2-(tert-Butoxy)-2-(4-(2,3-dihydropyrano[4,3,2-de]quinolin-7-yl)-2-((4-fluoro-3-methylbenzyl)carbamoyl)-6-methylpyrazolo[1,5-a]pyridin-5-yl)acetic acid;

(S)-2-(tert-Butoxy)-2-(4-(4,4-dimethylpiperidin-1-yl)-2-((4-fluoro-3-methylbenzyl)carbamoyl)-6-methylpyrazolo[1,5-a]pyridin-5-yl)acetic acid;

(S)-2-(tert-Butoxy)-2-(4-(4,4-dimethylpiperidin-1-yl)-2-(5-(4-fluorobenzyl)thiazol-2-yl)-6-methylpyrazolo[1,5-a]pyridin-5-yl)acetic acid;

(S)-2-(tert-Butoxy)-2-(4-(4,4-dimethylpiperidin-1-yl)-2-(5-(4-fluorobenzyl)oxazol-2-yl)-6-methylpyrazolo[1,5-a]pyridin-5-yl)acetic acid;

(2S)-2-(tert-Butoxy)-2-(4-(5-chloro-3,4-dihydro-2H-benzo[b][1,4]oxazin-6-yl)-2-((4-fluoro-3-methylbenzyl)carbamoyl)-6-methylpyrazolo[1,5-a]pyridin-5-yl)acetic acid;

(2S)-2-(tert-Butoxy)-2-(4-(8-fluoro-5-methylchroman-6-yl)-2-(5-(4-fluorobenzyl)thiazol-2-yl)-6-methylpyrazolo[1,5-a]pyridin-5-yl)acetic acid;

(2S)-2-(tert-Butoxy)-2-(4-(8-fluoro-5-methylchroman-6-yl)-2-(5-(4-fluorobenzyl)oxazol-2-yl)-6-methylpyrazolo[1,5-a]pyridin-5-yl)acetic acid;

(2S)-2-(tert-Butoxy)-2-(4-(2,3-dihydropyrano[4,3,2-de]quinolin-7-yl)-2-(5-(4-fluorobenzyl)thiazol-2-yl)-6-methylpyrazolo[1,5-a]pyridin-5-yl)acetic acid;

(2S)-2-(tert-Butoxy)-2-(4-(2,3-dihydropyrano[4,3,2-de]quinolin-7-yl)-2-(5-(4-fluorobenzyl)oxazol-2-yl)-6-methylpyrazolo[1,5-a]pyridin-5-yl)acetic acid;

(2S)-2-(tert-Butoxy)-2-(4-(5-chloro-3,4-dihydro-2H-benzo[b][1,4]oxazin-6-yl)-2-(5-(4-fluorobenzyl)thiazol-2-yl)-6-methylpyrazolo[1,5-a]pyridin-5-yl)acetic acid;

(2S)-2-(tert-Butoxy)-2-(4-(5-chloro-3,4-dihydro-2H-benzo[b][1,4]oxazin-6-yl)-2-(5-(4-fluorobenzyl)oxazol-2-yl)-6-methylpyrazolo[1,5-a]pyridin-5-yl)acetic acid;

(2S)-2-(tert-Butoxy)-2-(4-(8-fluoro-5-methylchroman-6-yl)-6-methyl-2-(2'-methyl-[1,1'-biphenyl]-3-yl)pyrazolo[1,5-a]pyridin-5-yl)acetic acid;

(2S)-2-(tert-Butoxy)-2-(4-(8-fluoro-5-methylchroman-6-yl)-6-methyl-2-(3-(pyridin-3-yl)phenyl)pyrazolo[1,5-a]pyridin-5-yl)acetic acid;

(2S)-2-(tert-Butoxy)-2-(4-(2,3-dihydropyrano[4,3,2-de]quinolin-7-yl)-6-methyl-2-(2'-methyl-[1,1'-biphenyl]-3-yl)pyrazolo[1,5-a]pyridin-5-yl)acetic acid;

(2S)-2-(tert-Butoxy)-2-(4-(2,3-dihydropyrano[4,3,2-de]quinolin-7-yl)-6-methyl-2-(3-(pyridin-3-yl)phenyl)pyrazolo[1,5-a]pyridin-5-yl)acetic acid;

(2S)-2-(tert-Butoxy)-2-(4-(5-chloro-3,4-dihydro-2H-benzo[b][1,4]oxazin-6-yl)-6-methyl-2-(2'-methyl-[1,1'-biphenyl]-3-yl)pyrazolo[1,5-a]pyridin-5-yl)acetic acid;

(2S)-2-(tert-Butoxy)-2-(4-(5-chloro-3,4-dihydro-2H-benzo[b][1,4]oxazin-6-yl)-6-methyl-2-(3-(pyridin-3-yl)phenyl)pyrazolo[1,5-a]pyridin-5-yl)acetic acid;

(S)-2-(tert-Butoxy)-2-(4-(4,4-dimethylpiperidin-1-yl)-6-methyl-2-(2'-methyl-[1,1'-biphenyl]-3-yl)pyrazolo[1,5-a]pyridin-5-yl)acetic acid;

(S)-2-(tert-Butoxy)-2-(4-(4,4-dimethylpiperidin-1-yl)-6-methyl-2-(3-(pyridin-3-yl)phenyl)pyrazolo[1,5-a]pyridin-5-yl)acetic acid;

(2S)-2-(tert-Butoxy)-2-(4-(8-fluoro-5-methylchroman-6-yl)-2-(4-(4-fluorobenzyl)-1H-pyrazol-1-yl)-6-methylpyrazolo[1,5-a]pyridin-5-yl)acetic acid;

(2S)-2-(tert-Butoxy)-2-(4-(2,3-dihydropyrano[4,3,2-de]quinolin-7-yl)-2-(4-(4-fluorobenzyl)-1H-pyrazol-1-yl)-6-methylpyrazolo[1,5-a]pyridin-5-yl)acetic acid;

(2S)-2-(tert-Butoxy)-2-(4-(5-chloro-3,4-dihydro-2H-benzo[b][1,4]oxazin-6-yl)-2-(4-(4-fluorobenzyl)-1H-pyrazol-1-yl)-6-methylpyrazolo[1,5-a]pyridin-5-yl)acetic acid;

(S)-2-(tert-Butoxy)-2-(4-(4,4-dimethylpiperidin-1-yl)-2-(4-(4-fluorobenzyl)-1H-pyrazol-1-yl)-6-methylpyrazolo[1,5-a]pyridin-5-yl)acetic acid;

(2S)-2-(tert-Butoxy)-2-(10-(8-fluoro-5-methylchroman-6-yl)-8-methylpyrido[1,2-b]indazol-9-yl)acetic acid;

(2S)-2-(tert-Butoxy)-2-[(21E)-16-fluoro-4,25-dimethyl-10-oxo-19-oxa-1,6,11,30-tetraazapentacyclo[23.2.2.1$^{6,9}$.0$^{2,7}$.0$^{13,18}$]triaconta-2,4,7,9(30),13(18),14,16,21-octaen-3-yl]acetic acid;

(2S)-2-(tert-Butoxy)-2-[(23E)-4,27-dimethyl-21,26-dioxa-32-thia-1,6,11,33-tetraazahexacyclo[25.2.2.1$^{6,9}$.1$^{10,13}$.0$^{2,7}$.0$^{15,20}$]tritriaconta-2,4,7,9(33),10,12,15(20),16,18,23-decaen-3-yl]acetic acid;

(2S)-2-(tert-Butoxy)-2-[(22S)-4,17,22,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetic acid;

(2S)-2-(tert-Butoxy)-2-[(22S)-4,17,22,29-tetramethyl-21,28-dioxa-1,6,35-triazahexacyclo[27.2.2.1$^{6,9}$.1$^{10,14}$.0$^{2,7}$.0$^{15,20}$]pentatriaconta-2,4,7,9(35),10(34),11,13,15(20),16,18-decaen-3-yl]acetic acid;

(2S)-2-(tert-Butoxy)-2-[(22R)-4,17,22,29-tetramethyl-21,28-dioxa-1,6,35-triazahexacyclo[27.2.2.1$^{6,9}$.1$^{10,14}$.0$^{2,7}$.0$^{15,20}$]pentatriaconta-2,4,7,9 (35),10 (34),11,13,15(20),16,18-decaen-3-yl]acetic acid;

(2S)-2-(tert-Butoxy)-2-[(23S)-4,17,23,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetic acid;

(2S)-2-(tert-Butoxy)-2-[(23R)-4,17,23,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9 (34),10 (33),11,13,15 (20),16,18-decaen-3-yl]acetic acid;

(2S)-2-(tert-Butoxy)-2-[(22S)-16-fluoro-4,22,28-trimethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetic acid;

(2S)-2-(tert-Butoxy)-2-[(22S)-17-fluoro-4,22,28-trimethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetic acid;

(2S)-2-(tert-Butoxy)-2-[(22S)-17-fluoro-4,22,27-trimethyl-21,26-dioxa-1,6,33-triazahexacyclo[25.2.2.1$^{6,9}$.1$^{10,14}$.0$^{2,7}$.0$^{15,20}$]tritriaconta-2,4,7,9(33),10 (32),11,13,15(20),16,18-decaen-3-yl]acetic acid;

(2S)-2-(tert-Butoxy)-2-[(22S)-18-fluoro-4,22,28-trimethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetic acid;

(2S)-2-(tert-Butoxy)-2-[(22S)-16-fluoro-4,17,22,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9 (34),10 (33),11,13,15(20),16,18-decaen-3-yl]acetic acid;

(2S)-2-(tert-Butoxy)-2-[(22R)-16-fluoro-4,17,22,28-tetramethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetic acid;

(2S)-2-(tert-Butoxy)-2-[2-(3-{2-fluoro-3-methyl-6-[(2S)-pentan-2-yloxy]phenyl}phenyl)-6-methyl-4-(4-methyl-4-propoxypiperidin-1-yl)pyrazolo[1,5-a]pyridin-5-yl]acetic acid;

(2S)-2-(tert-Butoxy)-2-[(22S)-17-cyano-4,22,28-trimethyl-21,27-dioxa-1,6,34-triazahexacyclo[26.2.2.1$^{6,9}$.1$^{10,14}$.0$^{2,7}$.0$^{15,20}$]tetratriaconta-2,4,7,9(34),10(33),11,13,15(20),16,18-decaen-3-yl]acetic acid; and (S)-2-(4-(4-(Allyloxy)-4-methylpiperidin-1-yl)-2-(3-bromophenyl)-6-methylpyrazolo[1,5-a]pyridin-5-yl)-2-(tert-butoxy)acetic acid.

or a pharmaceutically acceptable salt thereof.

12. A composition useful for treating HIV infection comprising a therapeutic amount of a compound of claim 1 and a pharmaceutically acceptable carrier.

13. The composition of claim 12 further comprising a therapeutically effective amount at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors, and a pharmaceutically acceptable carrier.

14. A method for treating HIV infection comprising administering a therapeutically effective amount of a compound of claim 1, or a pharmaceutically acceptable salt thereof, to a patient in need thereof.

15. The method of claim 14 further comprising administering a therapeutically effective amount of at least one other agent used for treatment of AIDS or HIV infection selected from the group consisting of nucleoside HIV reverse transcriptase inhibitors, non-nucleoside HIV reverse transcriptase inhibitors, HIV protease inhibitors, HIV fusion inhibitors, HIV attachment inhibitors, CCR5 inhibitors, CXCR4 inhibitors, HIV budding or maturation inhibitors, and HIV integrase inhibitors.

* * * * *